US011041019B2

(12) United States Patent
Hays et al.

(10) Patent No.: US 11,041,019 B2
(45) Date of Patent: Jun. 22, 2021

(54) ANTI HUMAN ANNEXIN A1 ANTIBODY

(71) Applicant: MEDANNEX LTD., Edinburgh (GB)

(72) Inventors: Henry Charles Wilson Hays, Edinburgh (GB); Christopher Barry Wood, Edinburgh (GB); Tina Caroline Flatau, Edinburgh (GB)

(73) Assignee: MEDANNEX LTD., Edinburgh (GB)

( * ) Notice: Subject to any disclaimer, the term of this patent is extended or adjusted under 35 U.S.C. 154(b) by 0 days.

(21) Appl. No.: 16/484,286

(22) PCT Filed: Feb. 8, 2018

(86) PCT No.: PCT/EP2018/053232

§ 371 (c)(1),
(2) Date: Aug. 7, 2019

(87) PCT Pub. No.: WO2018/146230

PCT Pub. Date: Aug. 16, 2018

(65) Prior Publication Data

US 2020/0031911 A1 Jan. 30, 2020

(30) Foreign Application Priority Data

Feb. 8, 2017 (GB) ..................................... 1702091

(51) Int. Cl.

| | |
|---|---|
| ***A61K 39/395*** | (2006.01) |
| ***A61K 39/00*** | (2006.01) |
| ***C07K 16/00*** | (2006.01) |
| ***C07K 16/18*** | (2006.01) |
| ***A61K 51/08*** | (2006.01) |

(52) U.S. Cl.

CPC .......... *C07K 16/18* (2013.01); *A61K 39/3955* (2013.01); *A61K 51/087* (2013.01); *C07K 2317/24* (2013.01); *C07K 2317/56* (2013.01); *C07K 2317/565* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,051,364 | A | 9/1991 | Isacke et al. | |
| 5,162,311 | A | 11/1992 | Herrling et al. | |
| 5,565,338 | A | 10/1996 | Ishizaka | |
| 5,567,440 | A | 10/1996 | Hubbell et al. | |
| 9,127,051 | B2 * | 9/2015 | D'Acquisto | A61P 21/00 |
| 10,752,677 | B2 * | 8/2020 | D'Acquisto | A61P 25/22 |
| 2005/0113297 | A1 | 5/2005 | Francois et al. | |
| 2006/0024315 | A1 | 2/2006 | Schnitzer et al. | |
| 2015/0004164 | A1 * | 1/2015 | D'Acquisto | A61P 25/22 424/135.1 |
| 2015/0086553 | A1 | 3/2015 | Han et al. | |

FOREIGN PATENT DOCUMENTS

| | | |
|---|---|---|
| EP | 2 551 347 | 1/2013 |
| WO | 03/057715 | 7/2003 |
| WO | 2005/027965 | 3/2005 |
| WO | 2005/117848 | 12/2005 |
| WO | 2010/064012 | 6/2010 |
| WO | 2013/088110 | 6/2013 |
| WO | 2013/088111 | 6/2013 |

OTHER PUBLICATIONS

Cai et al., "Preparation and identification of monoclonal antibody against annexin I", Tumor, Nov. 2006, pp. 979-983, vol. 26, No. 11, with English translations of the abstract and figure legends.

International Search Report and Written Opinion of the International Searching Authority, dated May 9, 2018 in corresponding International Patent Application No. PCT/EP2018/053232.

D'Acquisto et al., "Annexin-A1: a pivotal regulator of the innate and adaptive immune systems", British Journal of Pharmacology, 155: 152-169 (2008).

Paschalidis et al., "Modulation of experimental autoimmune encephalomyelitis by endogenous Annexin A1", Journal of Neuroinflammation, 6(33): 1-12 (2009).

Alonso et al., "Animal models of obsessive-compulsive disorder: utility and limitations", Neuropsychiatric Disease and Treatment, 2015, vol. 11, pp. 1939-1955.

Brown et al., "Tolerance of single, but not multiple, amino acid replacement in antibody VH CDR 2: a means of minimizing B cell wastage from somatic hypermutation?" Journal of Immunology, 1996, vol. 159, No. 9, pp. 3285-3291.

(Continued)

*Primary Examiner* — Maher M Haddad

(74) *Attorney, Agent, or Firm* — Wenderoth, Lind & Ponack, L.L.P.

(57) ABSTRACT

The present invention relates to an isolated specific binding molecule which binds human Anx-A1 and comprises the complementarity-determining regions (CDRs) VLCDR1, VLCDR2, VLCDR3, VHCDR1, VHCDR2 and VHCDR3, wherein each of said CDRs has an amino acid sequence as follows:

Figure 1:
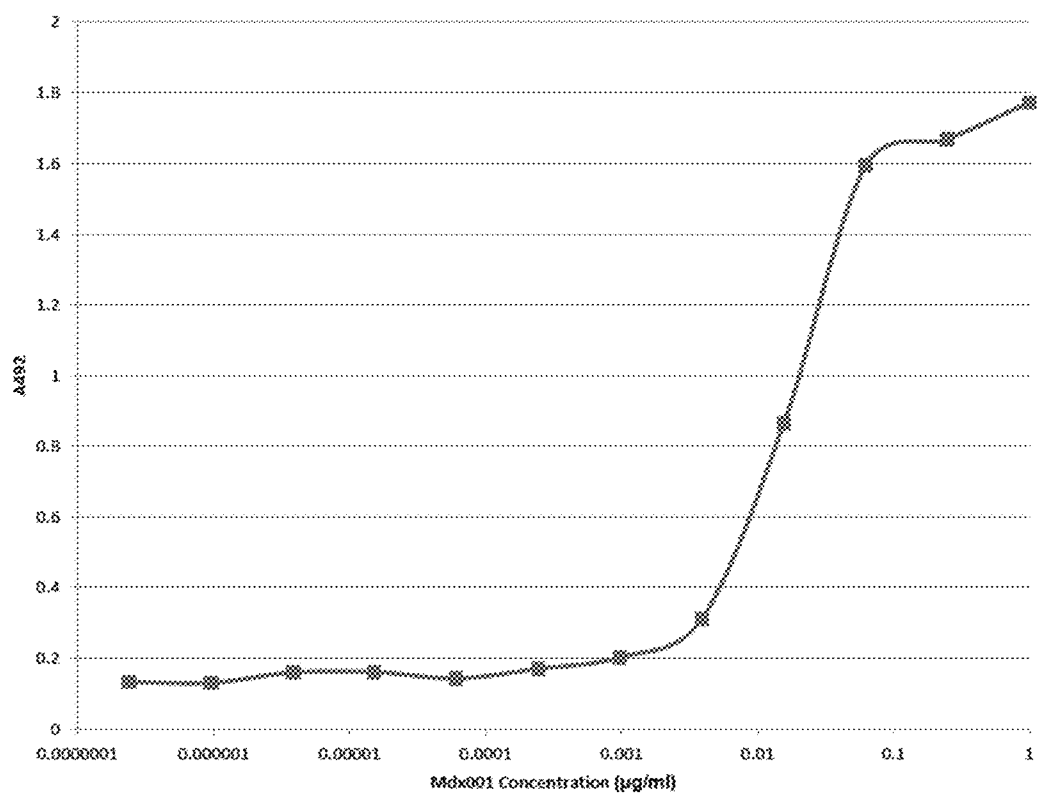

VLCDR1 has the sequence set forth in SEQ ID NO: 1, 36 or 37;

VLCDR2 has the sequence set forth in SEQ ID NO: 2;

VLCDR3 has the sequence set forth in SEQ ID NO: 3;

VHCDR1 has the sequence set forth in SEQ ID NO: 4;

VHCDR2 has the sequence set forth in SEQ ID NO: 5; and

VHCDR3 has the sequence set forth in SEQ ID NO: 6; or, for each sequence, an amino acid sequence with at least 85% sequence identity thereto.

The specific binding molecule disclosed is therapeutically useful and in particular may be used in therapy for T-cell mediated diseases, including autoimmune diseases such as rheumatoid arthritis and systemic lupus erythematosus, obsessive compulsive disorder (OCD), and OCD-related diseases, such as anxiety disorders.

18 Claims, 14 Drawing Sheets

Specification includes a Sequence Listing.

(56) References Cited

OTHER PUBLICATIONS

D'Acquisto et al., "Annexin A1: a novel target of the immunosuppressive effects of Glucocorticoids in autoimmune diseases", FASEB Journal, 2006, vol. 20, No. 5, A1376.

D'Acquisto et al., "Annexin-1 modulates T-cell activation and differentiation", Blood, 2007, vol. 109, No. 3, pp. 1095-1102.

D'Acquisto et al., "Impaired T cell activation and increased Th2 lineage commitment in Annexin-1-deficient T cells", Eur. J. Immunol., 2007, vol. 37, pp. 3131-3142.

Falini et al., "Simple diagnostic assay for hairy cell leukaemia by immunocytochemical detection of annexin A1 (ANXA1)", The Lancet, 2004, vol. 363, pp. 1869-1871.

Flower et al., "Lipocortin-1: cellular mechanisms and clinical relevance", Trends in Pharmacological Sciences, 1994, vol. 15, No. 3, pp. 71-76.

Gao et al., "Reduced Fear Memory and Anxiety-like Behavior in Mice Lacking Formylpeptide Receptor 1", Behavior Genetics, 2011, vol. 41, No. 5, pp. 724-733.

Huitinga et al., "Effect of annexin-1 on experimental autoimmune encephalomyelitis (EAE) in the rat", Clinical Experimental Immunology, 1998, vol. 111, No. 1, pp. 198-204.

Iaccarino et al., "Anti-annexins autoantibodies: Their role as biomarkers of autoimmune diseases", Autoimmunity Reviews, 2011, vol. 10, No. 9, pp. 553-558.

Oliani et al., "Neutrophil Interaction with Inflamed Postcapillary Venule Endothelium Alters Annexin 1 Expression", American Journal of Pathology, 2001, vol. 158, No. 2, pp. 603-615.

Owens et al., "The genetic engineering of monoclonal antibodies" Journal of Immunological Methods, 1994, vol. 168, No. 2, pp. 149-165.

Pepinsky et al., "Monoclonal antibodies to lipocortin-1 as probes for biological function", FEBS, 1990, vol. 261, No. 2, pp. 247-252.

Perretti et al., "Acute inflammatory response in the mouse: exacerbation by immunoneutralization of lipocortin 1", 1996, British Journal of Pharmacology, vol. 117, No. 6, pp. 1145-1154.

Rudikoff et al., "Single amino acid substitution altering antigen-binding specificty", PNAS, 1982, vol. 79, No. 6, pp. 1979-1983.

United Kingdom Search Report dated Nov. 29, 2017 in corresponding United Kingdom Application No. 1702091.8.

van Eden et al., "Immune Regulation in Adjuvant-Induced Arthritis", Arthritis & Rheumatism, 2003, vol. 48, No. 7, pp. 1788-1796.

Vajdos et al., "Comprehensive Functional Maps of the Antigen-binding Site of an Anti-ErbB2 Antibody Obtained with Shotgun Scanning Mutagenesis", Journal of Molecular Biology, 2002, vol. 320, pp. 415-428.

Wang et al., "Assessing the validity of current mouse genetic models of obsessive-compulsive disorder", Behavioural Pharmacology, 2009, vol. 20, No. 2, pp. 119-133.

Yang et al., "Antiinflammatory Effect of Lipocortin 1 in Experimental Arthritis", Inflammation, 1997, vol. 21, No. 6, pp. 583-596.

Yang et al., "Inhibitory Effect of Annexin I on Synovial Inflammation in Rat Adjuvant Arthritis", Arthritis & Rheumatism, 1999, vol. 42, No. 7, pp. 1538-1544.

Yang et al., "Modulation of Inflammation and Response to Dexamethasone by Annexin 1 in Antigen-Induced Arthritis", Arthritis & Rheumatism, 2004, vol. 50, No. 3, pp. 976-984.

Communication pursuant to Article 94(3) EPC dated Feb. 15, 2021 in European Patent Application No. 18 707 635.1.

Karsten Winkler et al., "Changing the Antigen Binding Specificity by Single Point Mutations of an Anti-p24 (HIV-1) Antibody", The Journal of Immunology, Oct. 2000; vol. 165, No. 8, pp. 4505-4514.

Jennifer A. Maynard et al., "Protection against anthrax toxin by recombinant antibody fragments correlates with antigen affinity", Nature Biotechnology, Jul. 2002, vol. 20, No. 6, pp. 597-601.

Rodrigo Barderas et al., "Affinity maturation of antibodies assisted by in silico modeling", Proceedings of the National Academy of Sciences, Jul. 2008, vol. 105, No. 26, pp. 9029-9034.

* cited by examiner

Figure 3

MDX-L1H4

Native

>Light Chain
DVVMTQSPLSLPVTLGQPASISCRSSQSLENSNGKTYLNWFQQRPGQSPRRLIYG
VSNRFSGVPDRFSGSGSGTDFTLKISRVEAEDVGVYFCLQVTHVPYTFGQGTKLEIK >Heavy Chain
QVQLVQSGAEVKKPGSSVKVSCKASGYTFTNYWIGWVRQAPGQGLEWVGDIYP
GGDYTNYNEKFKGRVTITADKSTSTAYMELSSLRSEDTAVYYCARWGLGYYFDYW
GQGTMVTVSS

Variant 1

>Light Chain
DVVMTQSPLSLPVTLGQPASISCRSSQSLENSNAKTYLNWFQQRPGQSPRRLIYG
VSNRFSGVPDRFSGSGSGTDFTLKISRVEAEDVGVYFCLQVTHVPYTFGQGTKLEIK >Heavy Chain
QVQLVQSGAEVKKPGSSVKVSCKASGYTFTNYWIGWVRQAPGQGLEWVGDIYP
GGDYTNYNEKFKGRVTITADKSTSTAYMELSSLRSEDTAVYYCARWGLGYYFDYW
GQGTMVTVSS

Variant 2

>Light Chain
DVVMTQSPLSLPVTLGQPASISCRSSQSLENTNGKTYLNWFQQRPGQSPRRLIYG
VSNRFSGVPDRFSGSGSGTDFTLKISRVEAEDVGVYFCLQVTHVPYTFGQGTKLEIK >Heavy Chain
QVQLVQSGAEVKKPGSSVKVSCKASGYTFTNYWIGWVRQAPGQGLEWVGDIYP
GGDYTNYNEKFKGRVTITADKSTSTAYMELSSLRSEDTAVYYCARWGLGYYFDYW
GQGTMVTVSS

Variant 3 (Poorly Functional)

>Light Chain
DVVMTQSPLSLPVTLGQPASISCRSSQSLENSDGKTYLNWFQQRPGQSPRRLIYG
VSNRFSGVPDRFSGSGSGTDFTLKISRVEAEDVGVYFCLQVTHVPYTFGQGTKLEIK >Heavy Chain
QVQLVQSGAEVKKPGSSVKVSCKASGYTFTNYWIGWVRQAPGQGLEWVGDIYP
GGDYTNYNEKFKGRVTITADKSTSTAYMELSSLRSEDTAVYYCARWGLGYYFDYW
GQGTMVTVSS

Figure 3 (Cont.)

MDX-L2H2

Native

>Light Chain
DIVMTQTPLSLSVTPGQPASISCRSSQSLENSNGKTYLNWYLQKPGQSPQLLIYGV
SNRFSGVPDRFSGSGSGTDFTLKISRVEAEDVGVYYCLQVTHVPYTFGQGTKVEIK >Heav Chain
QVQLVQSGPEVKKPGESLKISCKGSGYTFTNYWIGWVRQAPGKGLEWMGDIYP
GGDYTNYNEKFKGQVTISADKSISTAYLQWSSLKASDTAIYYCARWGLGYYFDYW
GRGTLVTVSS

Variant 1

>Light Chain
DIVMTQTPLSLSVTPGQPASISCRSSQSLENSNAKTYLNWYLQKPGQSPQLLIYGV
SNRFSGVPDRFSGSGSGTDFTLKISRVEAEDVGVYYCLQVTHVPYTFGQGTKVEIK >Heavy Chain
QVQLVQSGPEVKKPGESLKISCKGSGYTFTNYWIGWVRQAPGKGLEWMGDIYP
GGDYTNYNEKFKGQVTISADKSISTAYLQWSSLKASDTAIYYCARWGLGYYFDYW
GRGTLVTVSS

Variant 2

>Light Chain
DIVMTQTPLSLSVTPGQPASISCRSSQSLENTNGKTYLNWYLQKPGQSPQLLIYGV
SNRFSGVPDRFSGSGSGTDFTLKISRVEAEDVGVYYCLQVTHVPYTFGQGTKVEIK >Heavy Chain
QVQLVQSGPEVKKPGESLKISCKGSGYTFTNYWIGWVRQAPGKGLEWMGDIYP
GGDYTNYNEKFRGQVTISADKSISTAYLQWSSLKASDTAIYYCARWGLGYYFDYW
GRGTLVTVSS

Variant 3 (Poorly Functional)

>Light Chain
DIVMTQTPLSLSVTPGQPASISCRSSQSLENSQGKTYLNWYLQKPGQSPQLLIYGV
SNRFSGVPDRFSGSGSGTDFTLKISRVEAEDVGVYFCLQVTHVPYTFGQGTKVEIK >Heavy Chain
QVQLVQSGPEVKKPGESLKISCKGSGYTFTNYWIGWVRQAPGKGLEWMGDIYP
GGDYTNYNEKFRGQVTISADKSISTAYLQWSSLKASDTAIYYCARWGLGYYFDYW
GRGTLVTVSS

A

B

ANTI HUMAN ANNEXIN A1 ANTIBODY

The present invention relates to specific binding molecules, particularly monoclonal antibodies and fragments thereof, which bind human annexin A1 (Anx-A1), and their uses in the treatment of certain diseases. The invention also extends to nucleic acid molecules and suchlike which encode the specific binding molecules of the invention and preparations and compositions which comprise the specific binding molecules.

Anx-A1 has in recent years been shown by a number of research groups to play a homeostatic role in various cell types of both the innate and adaptive immune systems. For instance, Anx-A1 has been shown to exert homeostatic control over cells of the innate immune system such as neutrophils and macrophages, and also to play a role in T-cells by modulating the strength of T-cell receptor (TCR) signalling (D'Acquisto et al., Blood 109: 1095-1102, 2007).

High levels of Anx-A1 lower the threshold for T-cell activation and promote differentiation of CD4+ T-cells into $T_h1$ and $T_h17$ cells. In contrast, the T-cells of Anx-A1-deficient mice have been found to display impaired activation and increased differentiation into $T_h2$ cells (D'Acquisto et al., Eur. J. Immunol. 37: 3131-3142, 2007). These findings have led to the development of treatments for a number of diseases, particularly T-cell mediated diseases, based on the targeting of Anx-A1 using specific binding molecules, such as antibodies (see e.g. WO 2010/064012, WO 2011/154705 and WO 2013/088111). By targeting Anx-A1 in this manner, levels of T-cell activity are reduced which alleviates the symptoms of diseases characterised by excess T-cell activity, in particular autoimmune diseases.

Four human Anx-A1 transcription variants are known: ANXA1-002, ANXA1-003, ANXA1-004 and ANXA1-006, which are obtained by alternative splicing of the Anx-A1 gene. ANXA1-002 and ANXA1-003 encode full-length versions of Anx-A1; due to alternative splicing the ANXA1-002 and ANXA1-003 mRNA transcripts are of different lengths, but the same protein is encoded by each (SEQ ID NOs: 10 and 11). The proteins encoded by ANXA1-004 (SEQ ID NO: 12) and ANXA1-006 (SEQ ID NO: 13) correspond to fragments of full-length Anx-A1.

The inventors of the present invention have identified a monoclonal antibody which binds to human Anx-A1 with high affinity, and is thus able to specifically inhibit T-cell activation. Advantageously, the antibody is able to inhibit T-cell activation without causing any adverse cytotoxic effects. The antibody may be used in the treatment of a number of conditions, including T-cell mediated diseases such as autoimmune diseases and graft-versus-host disease, obsessive compulsive disorder (OCD) and OCD-related diseases.

As is known to the skilled person, antibodies are proteins which comprise four polypeptide chains: two heavy chains and two light chains. Typically, the heavy chains are identical to each other and the light chains are identical to each other. The light chains are shorter (and thus lighter) than the heavy chains. The heavy chains comprise four or five domains: at the N-terminus a variable ($V_H$) domain is located, followed by three or four constant domains (from N-terminus to C-terminus $C_H1$, $C_H2$, $C_H3$ and, where present, $C_H4$, respectively). The light chains comprise two domains: at the N-terminus a variable ($V_L$) domain is located and at the C-terminus a constant ($C_L$) domain is located. In the heavy chain an unstructured hinge region is located between the $C_H1$ and $C_H2$ domains. The two heavy chains of an antibody are joined by disulphide bonds formed between cysteine residues present in the hinge region, and each heavy chain is joined to one light chain by a disulphide bond between cysteine residues present in the $C_H1$ and $C_L$ domains, respectively.

In mammals two types of light chain are produced, known as lambda (λ) and kappa (κ). For kappa light chains, the variable and constant domains can be referred to as $V_\kappa$ and $C_\kappa$ domains, respectively. Whether a light chain is a λ or κ light chain is determined by its constant region: the constant regions of λ and κ light chains differ, but are the same in all light chains of the same type in any given species.

The constant regions of the heavy chains are the same in all antibodies of any given isotype in a species, but differ between isotypes (examples of antibody isotypes are classes IgG, IgE, IgM, IgA and IgD; there are also a number of antibody sub-types, e.g. there are four sub-types of IgG antibodies: IgG1, IgG2, IgG3 and IgG4). The specificity of an antibody is determined by the sequence of its variable region. The sequence of variable regions varies between antibodies of the same type in any individual. In particular, both the light and heavy chains of an antibody comprise three hypervariable complementarity-determining regions (CDRs). In a pair of a light chain and a heavy chain, the CDRs of the two chains form the antigen-binding site. The CDR sequences determine the specificity of an antibody.

The three CDRs of a heavy chain are known as VHCDR1, VHCDR2 and VHCDR3, from N-terminus to C-terminus, and the three CDRs of a light chain are known as VLCDR1, VLCDR2 and VLCDR3, from N-terminus to C-terminus.

In WO 2011/154705, a monoclonal antibody was disclosed which was claimed to bind Anx-A1 with high affinity. The antibody was produced from a murine hybridoma (i.e. a hybridoma generated from a murine B-cell) using murine cells from a mouse genetically immunised with human Anx-A1 isoform ANXA1-003. The antibody was known as VJ-4B6. VJ-4B6 is an antibody of isotype IgG2b. The antibody is produced by the hybridoma deposited with the European Collection of Cell Cultures (ECACC) under accession number 10060301. VJ-4B6 was defined as having the following CDR sequences: VHCDR1-GYTFTNYWIG (SEQ ID NO: 4; VHCDR2-DIYPGGDYTNYNEKFKG (SEQ ID NO: 5); VHCDR3-WGLGYYFDY (SEQ ID NO: 14); VLCDR1-KASENVVTYVS (SEQ ID NO: 7); VLCDR2-GASNRYT (SEQ ID NO: 8); and VLCDR3-GQGYSYPYT (SEQ ID NO: 9).

The inventors of the present invention synthesised a humanised version of the disclosed VJ-4B6 antibody intended for use in medicine. The humanised VJ-4B6 antibody failed to bind human Anx-A1 in vitro. The present inventors re-examined the antibodies produced by the hybridoma and identified, as a minor component, a second light chain produced by the hybridoma. Neither the sequence of this light chain, nor its presence in Anx-A1 binding antibodies was identified when the hybridoma was first characterised.

The second light chain has CDRs with the following sequences: VLCDR1-RSSQSLENSNGKTYLN (SEQ ID NO: 1); VLCDR2-GVSNRFS (SEQ ID NO: 2); and VLCDR3-LQVTHVPYT (SEQ ID NO: 3). The complete sequence of this second light chain is set forth in SEQ ID NO: 15.

Additionally, while ECACC 10060301 was confirmed to produce only a single heavy chain, re-analysis of the heavy chain showed that VHCDR3 in fact has the sequence ARWGLGYYFDY (SEQ ID NO: 6). The complete sequence of the heavy chain produced by hybridoma ECACC 10060301 is set forth in SEQ ID NO: 16.

A murine antibody was synthesised in which the light chain had the sequence of SEQ ID NO: 15 (i.e. VLCDR1-3 had the sequences of SEQ ID NOs: 1-3, respectively) and the heavy chain had the sequence of SEQ ID NO: 16 (i.e. VHCDR1-3 had the sequences of SEQ ID NOs: 4-6, respectively). This murine antibody, also of isotype IgG2b, was named Mdx001, and was found to bind human Anx-A1 with high affinity (see the Examples provided herein). The antibody has a previously unknown sequence and various utilities in medicine. The antibody has a particularly high affinity of binding to human Anx-A1, rendering it particularly useful in medicine and superior to antibodies or other specific binding molecules which bind Anx-A1 which have previously been disclosed.

Humanised versions of the Mdx001 antibody have been generated. In particular two humanised versions of the antibody have been generated, to provide MDX-L1H4 and MDX-L2H2. The sequences of these variable regions are provided in SEQ ID NOs 32 and 33 (light and heavy chain variable regions of MDX-L1H4) and SEQ ID NOs 34 and 35 (light and heavy chain variable regions of MDX-L2H2). In these sequences the CDRs are as set forth in the above sequences for Mdx001.

Modification of the VLCDR1 sequence of the humanised versions of Mdx001 was found to yield enhanced antibodies. Substitution of the glycine residue at position 11 of SEQ ID NO: 1 (which as detailed above is the sequence of the Mdx001 VLCDR1) enhances antibody stability and function. Without being bound by theory it is believed that this is achieved by removing a site for post-translational modification of the CDR. Specifically, it is believed that substitution of this glycine residue removes a deamidation site from the protein. The VLCDR1 sequence set forth in SEQ ID NO: 1 comprises the sequence motif Ser-Asn-Gly. This sequence motif is associated with deamidation of the Asn residue, which leads to conversion of the asparagine residue to aspartic acid or isoaspartic acid, which can affect antibody stability and target binding. Substitution of any one of the residues within the Ser-Asn-Gly motif is believed to remove the deamidation site.

Surprisingly, the inventors have identified antibodies in which the glycine residue at position 11 (which is the glycine residue located within the above-described deamidation site) is substituted for alanine and which display enhanced binding to their target (Anx-A1) relative the native, Mdx001 antibody. The VLCDR1 comprising the substitution of glycine at position 11 for alanine has the amino acid sequence RSSQSLENSNAKTYLN (the residue in bold is the alanine introduced by the aforementioned substitution). This amino acid sequence is set forth in SEQ ID NO: 36 and is referred to as VLCDR1 variant 1. Further, humanised antibodies comprising a VLCDR1 modified at position 9, by substitution of serine for threonine, were also found to display enhanced binding of Anx-A1 relative to Mdx001. The VLCDR1 comprising the substitution of serine at position 9 for threonine has the amino acid sequence RSSQSLENTNGKTYLN (the residue in bold is the threonine introduced by the aforementioned substitution). This amino acid sequence is set forth in SEQ ID NO: 37 and is referred to as VLCDR1 variant 2.

A modified version of the humanised antibody MDX-L1H4 which has VLCDR1 variant 1 is referred to as MDX-L1M2H4; correspondingly a modified version of the humanised antibody MDX-L2H2 which has VLCDR1 variant 1 is referred to as MDX-L2M2H2. A modified version of the humanised antibody MDX-L1H4 which has VLCDR1 variant 2 is referred to as MDX-L1M3H4; correspondingly a modified version of the humanised antibody MDX-L2H2 which has VLCDR1 variant 2 is referred to as MDX-L2M3H2.

Thus, in a first embodiment, the invention provides an isolated specific binding molecule which binds human Anx-A1, the specific binding molecule comprising the CDRs VLCDR1, VLCDR2, VLCDR3, VHCDR1, VHCDR2 and VHCDR3, wherein each of said CDRs has an amino acid sequence as follows:

VLCDR1 has the sequence set forth in SEQ ID NO: 1 (RSSQSLENSNGKTYLN) or SEQ ID NO: 36 (RSSQSLENSNAKTYLN) or SEQ ID NO:37 (RSSQSLENTNGKTYLN);

VLCDR2 has the sequence set forth in SEQ ID NO: 2 (GVSNRFS);

VLCDR3 has the sequence set forth in SEQ ID NO: 3 (LQVTHVPYT);

VHCDR1 has the sequence set forth in SEQ ID NO: 4 (GYTFTNYWIG);

VHCDR2 has the sequence set forth in SEQ ID NO: 5 (DIYPGGDYTNYNEKFKG); and

VHCDR3 has the sequence set forth in SEQ ID NO: 6 (ARWGLGYYFDY); or, for each sequence, an amino acid sequence with at least 85% sequence identity thereto. Preferably said sequence identity is at least 90% or 95%.

In another embodiment, the invention provides a preparation containing the specific binding molecule of the invention, wherein at least 90% of the specific binding molecules in the preparation that bind to human Anx-A1 bind with a $K_d$ of less than 20 nM, preferably less than 15 nM or 10 nM.

In another embodiment, the invention provides a nucleic acid molecule comprising a nucleotide sequence encoding a specific binding molecule of the invention. A construct comprising a nucleic acid molecule of the invention is also provided, as is a vector comprising a nucleic acid molecule or construct of the invention. The invention also provides a host cell comprising a nucleic acid molecule, construct or vector of the invention.

In another embodiment, the invention provides a method of preparing a specific binding molecule of the invention, comprising:

i) introducing into a host cell a nucleic acid molecule, a construct or a vector of the invention;

ii) expressing the nucleic acid molecule such that the specific binding molecule is produced; and iii) collecting the specific binding molecule, preferably by purification.

Also provided by the invention is a pharmaceutical composition comprising a specific binding molecule of the invention and one or more pharmaceutically acceptable diluents, carriers or excipients. A specific binding molecule obtainable by this method of the invention is also provided.

Another embodiment of the invention is a specific binding molecule of the invention for use in therapy. The invention also provides a preparation or pharmaceutical composition of the invention for use in therapy. In certain embodiments, the specific binding molecule, preparation or pharmaceutical composition of the invention for use in therapy is for use in the treatment of a T-cell mediated disease, obsessive compulsive disorder (OCD) or an OCD-related disease.

Similarly, the invention also provides the use of a specific binding molecule or preparation of the invention in the manufacture of a medicament for use in the treatment of T-cell mediated disease, OCD or an OCD-related disease.

The invention also provides a method of treatment for a T-cell mediated disease, OCD or an OCD-related disease, comprising administering to a subject in need thereof a specific binding molecule, preparation or composition of the invention.

As mentioned above, the invention provides an isolated specific binding molecule which binds human Anx-A1. A "specific binding molecule" is a molecule which binds specifically to a particular molecular partner, in this case human Anx-A1. A molecule which binds specifically to human Anx-A1 is a molecule which binds to human Anx-A1 with a greater affinity than that with which it binds to other molecules (e.g. with an affinity as described in the Examples), or at least most other molecules. Thus, for example, if a specific binding molecule which binds human Anx-A1 were contacted with a lysate of human cells, the specific binding molecule would bind primarily to Anx-A1. In particular, the specific binding molecule binds to a sequence or configuration present on said human Anx-A1, preferably a unique sequence or configuration not present on other molecules. When the specific binding molecule is an antibody the sequence or configuration is the epitope to which the specific binding molecule binds. A specific binding molecule does not necessarily bind only to human Anx-A1: the specific binding molecule may cross-react with certain other undefined target molecules, or may display a level of non-specific binding when contacted with a mixture of a large number of molecules (such as a cell lysate or suchlike). Regardless, a specific binding molecule of the invention shows specificity for Anx-A1. The skilled person will easily be able to identify whether a specific binding molecule shows specificity for Anx-A1 using standard techniques in the art, e.g. ELISA, Western-blot, surface plasmon resonance (SPR), etc.

As referred to herein, a molecule which "binds to human Anx-1" shows specificity, as described hereinbefore, for a human Anx-1 molecule. As indicated above, there are four human isoforms of human Anx-A1. The specific binding molecule of the invention binds to full-length AnxA1 (i.e. Anx-A1 encoded by the ANXA1-002 or ANXA1-003 transcript), the sequence of which is set forth in SEQ ID NO: 11 (and SEQ ID NO: 10). Full-length Anx-A1 (as encoded by the ANXA1-002 and ANXA1-003 transcripts) is a 346 amino acid protein. The antibody Mdx-001 was raised against the full-length Anx-A1 protein, as encoded by the ANXA1-002 and ANXA1-003 transcripts. Thus the specific binding molecule binds to full-length human Anx-A1. The specific binding molecule may also bind to particular fragments, parts or variants of full-length Anx-A1, as encoded by the ANXA1-002 or ANXA1-003 transcript, such as the fragments encoded by the ANXA1-004 and ANXA1-006 transcripts or fragments of full-length Anx-A1 containing the epitope to which the antibody described herein binds.

The specific binding molecule may be synthesised by any method known in the art. In particular, the specific binding molecule may be synthesised using a protein expression system, such as a cellular expression system using prokaryotic (e.g. bacterial) cells or eukaryotic (e.g. yeast, fungus, insect or mammalian) cells. Cells which may be used in the production of the specific binding molecule are discussed further below. An alternative protein expression system is a cell-free, in vitro expression system, in which a nucleotide sequence encoding the specific binding molecule is transcribed into mRNA, and the mRNA translated into a protein, in vitro. Cell-free expression system kits are widely available, and can be purchased from e.g. ThermoFisher Scientific (USA). Alternatively, specific binding molecules may be chemically synthesised in a non-biological system. Liquid-phase synthesis or solid-phase synthesis may be used to generate polypeptides which may form or be comprised within the specific binding molecule of the invention. The skilled person can readily produce specific binding molecules using appropriate methodology common in the art. In particular, the specific binding molecule may be recombinantly expressed in mammalian cells, such as CHO cells.

As indicated, the specific binding molecule of the invention is "isolated". (In an alternative embodiment the specific binding molecule is not isolated.) "Isolated", as used herein, means that the specific binding molecule is the primary component (i.e. majority component) of any solution or suchlike in which it is provided. In particular, if the specific binding molecule is initially produced in a mixture or mixed solution, isolation of the specific binding molecule means that it has been separated or purified therefrom. Thus, for instance, if the specific binding molecule is a polypeptide, and said polypeptide is produced using a protein expression system as discussed above, the specific binding molecule is isolated such that it is the most abundant polypeptide in the solution or composition in which it is present, preferably constituting the majority of polypeptides in the solution or composition, and is enriched relative to other polypeptides and biomolecules present in the native production medium. In particular, the specific binding molecule of the invention is isolated such that it is the predominant (majority) specific binding molecule in the solution or composition. In a preferred feature, the specific binding molecule is present in the solution or composition at a purity of at least 60, 70, 80, 90, 95 or 99% w/w when assessed relative to the presence of other components, particularly other polypeptide components, in the solution or composition.

If the specific binding molecule is a protein, e.g. produced in a protein expression system, a solution of the specific binding molecule may be analysed by quantitative proteomics to identify whether the specific binding molecule of the invention is predominant and thus isolated. For instance, 2D gel electrophoresis and/or mass spectrometry may be used. Such isolated molecules may be present in preparations or compositions as described hereinafter.

The specific binding molecule of the present invention may be isolated using any technique known in the art. For instance, if the specific binding molecule is a polypeptide, it may be produced with an affinity tag such as a polyhistidine tag, a strep tag, a FLAG tag, and HA tag or suchlike, to enable isolation of the molecule by affinity chromatography using an appropriate binding partner, e.g. a molecule carrying a polyhistidine tag may be purified using $Ni^{2+}$ ions. In embodiments in which the specific binding molecule is an antibody, the specific binding molecule may be isolated using affinity chromatography using one or more antibody-binding proteins, such as Protein G, Protein A, Protein NG or Protein L. Alternatively, the specific binding molecule may be isolated by e.g. size-exclusion chromatography or ion-exchange chromatography. A specific binding molecule produced by chemical synthesis (i.e. by a non-biological method), by contrast, is likely to be produced in an isolated form. Thus, no specific purification or isolation step is required for a specific binding molecule of the invention to be considered isolated, if it is synthesised in a manner which produces an isolated molecule.

The specific binding molecule of the invention comprises 6 CDR sequences, VLCDR1, VLCDR2, VLCDR3, VHCDR1, VHCDR2 and VHCDR3, wherein each of said CDRs has an amino acid sequence as follows:

VLCDR1 has the sequence set forth in SEQ ID NO: 1, 36 or 37;

VLCDR2 has the sequence set forth in SEQ ID NO: 2;

VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6; or, for each sequence, an amino acid sequence with at least 85%, 90% or 95% sequence identity thereto.

By "or, for each sequence, an amino acid sequence with at least 85%, 90% or 95% sequence identity thereto" is meant that each of the said CDRs may have the amino acid sequence specified in the relevant SEQ ID NO, or an amino acid sequence with at least 85%, 90% or 95% sequence identity thereto. Thus VLCDR1 has the sequence set forth in SEQ ID NO: 1, 36 or 37, or an amino acid sequence with at least 85%, 90% or 95% sequence identity to SEQ ID NO: 1, 36 or 37; VLCDR2 has the sequence set forth in SEQ ID NO: 2, or an amino acid sequence with at least 85%, 90% or 95% sequence identity to SEQ ID NO: 2; VLCDR3 has the sequence set forth in SEQ ID NO: 3, or an amino acid sequence with at least 85%, 90% or 95% sequence identity to SEQ ID NO: 3; VHCDR1 has the sequence set forth in SEQ ID NO: 4, or an amino acid sequence with at least 85%, 90% or 95% sequence identity to SEQ ID NO: 4; VHCDR2 has the sequence set forth in SEQ ID NO: 5, or an amino acid sequence with at least 85%, 90% or 95% sequence identity to SEQ ID NO: 5; and VHCDR3 has the sequence set forth in SEQ ID NO: 6, or an amino acid sequence with at least 85%, 90% or 95% sequence identity to SEQ ID NO: 6.

In a preferred embodiment of the invention, VLCDR1 has (by which is meant herein consists of) the sequence set forth in SEQ ID NO: 1, 36 or 37, VLCDR2 has the sequence set forth in SEQ ID NO: 2, VLCDR3 has the sequence set forth in SEQ ID NO: 3, VHCDR1 has the sequence set forth in SEQ ID NO: 4, VHCDR2 has the sequence set forth in SEQ ID NO: 5; and VHCDR3 has the sequence set forth in SEQ ID NO: 6. The sequences used in the binding molecule may comprise the sequences described herein.

As indicated, the specific binding molecule of the invention comprises 6 CDRs consisting of polypeptide sequences. As used herein, "protein" and "polypeptide" are interchangeable, and each refer to a sequence of 2 or more amino acids joined by one or more peptide bonds. Thus, the specific binding molecule may be a polypeptide. Alternatively, the specific binding molecule may comprise one or more polypeptides which comprise the CDR sequences. Preferably, the specific binding molecule of the invention is an antibody or an antibody fragment.

In a particular embodiment of the invention, the combined sequence of the said CDR sequences has at least 85%, 90% or 95% (e.g. at least 97 or 98%) sequence identity to the combined sequence of the amino acid sequences set forth in SEQ ID NOs: 1-6 or SEQ ID NOs: 36 and 2-6 or SEQ ID NOs: 37 and 2-6. By the "combined sequence of the CDR sequences" (or the combined sequences of the CDRs) is meant the sequence formed when the sequences are assembled end-to-end (even if in the molecule of interest they would appear with intervening sequences). In other words, the combined sequence of the CDR sequences is the amino acid sequence obtained when the CDR sequences are joined together in the order listed above (i.e. VLCDR1-VLCDR2-VLCDR3-VHCDR1-VHCDR2-VHCDR3), thus the combined sequence has at its N-terminus the N-terminal amino acid of VLCDR1; the C-terminus of VLCDR1 is joined directly to the N-terminus of VLCDR2; the C-terminus of VLCDR2 is joined directly to the N-terminus of VLCDR3; the C-terminus of VLCDR3 is joined directly to the N-terminus of VHCDR1; the C-terminus of VHCDR2 is joined directly to the N-terminus of VHCDR3; and the C-terminal amino acid of VHCDR3 forms the C-terminus of the combined sequence. By "joined directly" herein is meant that the N-terminal amino acid of a particular CDR sequence is placed immediately next to the C-terminal amino acid of the preceding CDR sequence, with no intervening amino acids (for the purposes of sequence identity assessment).

The combined sequence of the amino acid sequences set forth in SEQ ID NOs: 1-6 is formed by the process described in the paragraph above, i.e. the combined sequence has at its N-terminus the N-terminal amino acid of SEQ ID NO: 1; the C-terminal amino acid of SEQ ID NO: 1 is joined directly to the N-terminal amino acid sequence of SEQ ID NO: 2; the C-terminal amino acid of SEQ ID NO: 2 is joined directly to the N-terminal amino acid of SEQ ID NO: 3; the C-terminal amino acid of SEQ ID NO: 3 is joined directly to the N-terminal amino acid of SEQ ID NO: 4; the C-terminal amino acid of SEQ ID NO: 4 is joined directly to the N-terminal amino acid of SEQ ID NO: 5; the C-terminal amino acid of SEQ ID NO: 5 is joined directly to the N-terminal amino acid of SEQ ID NO: 6; and the C-terminal amino acid of SEQ ID NO: 6 forms the C-terminus of the combined sequence. The combined sequence of the amino acid sequences set forth in SEQ ID NOs: 1-6 is itself set forth in SEQ ID NO: 17. The combined sequence of the amino acid sequences set forth in SEQ ID NOs: 36 (or 37) and 2-6 is formed by the equivalent process, except SEQ ID NO: 1 is replaced with SEQ ID NO: 36 (or 37). The combined sequence of the amino acid sequences set forth in SEQ ID NOs: 36 and 2-6 (and 37 and 2-6) is set forth in SEQ ID NO: 38 (or 39).

In embodiments of the invention where the CDRs of the specific binding molecule have less than 100% sequence identity to the amino acid sequences of SEQ ID NOs: 1 (or 36 or 37) and 2-6, the CDR sequences may be altered by substitution, addition or deletion of an appropriate number of amino acids in the sequences of SEQ ID NOs: 1 (or 36 or 37) and 2-6. In another embodiment of the invention, each of the CDR sequences may be modified by the substitution, addition or deletion of up to 2 amino acids relative to SEQ ID NOs: 1 (or 36 or 37) and 2-6, with the proviso that the resultant CDR sequences have at least 85% or 90% sequence identity to SEQ ID NOs: 1 (or 36 or 37) and 2-6, as set out above. By "substitution, addition or deletion" is included combinations of substitutions, additions and deletions. Thus, in particular, VLCDR1 may have the sequence of SEQ ID NO: 1 (or 36 or 37) with 1 or 2 amino acid substitutions, additions or deletions; VLCDR2 may have the sequence of SEQ ID NO: 2 with 1 amino acid substitution, addition or deletion; VLCDR3 may have the sequence of SEQ ID NO: 3 with 1 amino acid substitution, addition or deletion; VHCDR1 may have the sequence of SEQ ID NO: 4 with 1 amino acid substitution, addition or deletion; VHCDR2 may have the sequence of SEQ ID NO: 5 with 1 or 2 amino acid substitutions, additions or deletions; and VHCDR3 may have the sequence of SEQ ID NO: 6 with 1 amino acid substitution, addition or deletion. Preferably said 1 or 2 amino acid substitutions of SEQ ID NO:1, 36 or 37 is/are at position 9 and/or 11 in that sequence.

When a CDR sequence is modified by substitution of a particular amino acid residue, the substitution may be a conservative amino acid substitution. The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus a conservative amino acid substitution may be considered to be a substitution in which a particular amino acid residue is substituted for a different amino acid in the same family. However, a substitution of a CDR residue may equally be a non-conservative substitution, in which one amino acid is substituted for another with a side-chain belonging to a different family.

Amino acid substitutions or additions in the scope of the invention may be made using a proteinogenic amino acid encoded by the genetic code, a proteinogenic amino acid not encoded by the genetic code, or a non-proteinogenic amino acid. Preferably any amino acid substitution or addition is made using a proteinogenic amino acid. The amino acids making up the sequence of the CDRs may include amino acids which do not occur naturally, but which are modifications of amino acids which occur naturally. Providing these non-naturally occurring amino acids do not alter the sequence and do not affect specificity, they may be used to generate CDRs described herein without reducing sequence identity, i.e. are considered to provide an amino acid of the CDR. For example derivatives of the amino acids such as methylated amino acids may be used. In one aspect, the specific binding molecule of the invention is not a natural molecule, i.e. is not a molecule found in nature.

Modifications to the amino acid sequences of the CDRs set out in SEQ ID NOs: 1-6, 36 and 37 may be made using any suitable technique, such as site-directed mutagenesis of the encoding DNA sequence or solid state synthesis.

Specific binding molecules of the invention comprise the above-described CDRs. Additionally, such molecules may contain linker moieties or framework sequences to allow appropriate presentation of the CDRs. Additional sequences may also be present which may conveniently confer additional properties, e.g. peptide sequences which allow isolation or identification of the molecules containing the CDRs such as those described hereinbefore. In such cases a fusion protein may be generated.

As stated above, CDRs of the specific binding molecule of the invention have at least 85% sequence identity to SEQ ID NOs: 1 (or 36 or 37) and 2-6, as set out above. Sequence identity may be assessed by any convenient method. However, for determining the degree of sequence identity between sequences, computer programmes that make pairwise or multiple alignments of sequences are useful, for instance EMBOSS Needle or EMBOSS stretcher (both Rice, P. et al., *Trends Genet.,* 16, (6) pp 276-277, 2000) may be used for pairwise sequence alignments while Clustal Omega (Sievers F et al., *Mol. Syst. Biol.* 7:539, 2011) or MUSCLE (Edgar, R. C., *Nucleic Acids Res.* 32(5):1792-1797, 2004) may be used for multiple sequence alignments, though any other appropriate programme may be used. Whether the alignment is pairwise or multiple, it must be performed globally (i.e. across the entirety of the reference sequence) rather than locally.

Sequence alignments and % identity calculations may be determined using for instance standard Clustal Omega parameters: matrix Gonnet, gap opening penalty 6, gap extension penalty 1. Alternatively the standard EMBOSS Needle parameters may be used: matrix BLOSUM62, gap opening penalty 10, gap extension penalty 0.5. Any other suitable parameters may alternatively be used.

For the purposes of this application, where there is dispute between sequence identity values obtained by different methods, the value obtained by global pairwise alignment using EMBOSS Needle with default parameters shall be considered valid.

As stated above, the specific binding molecule of the invention is preferably an antibody or an antibody fragment. An "antibody" is an immunoglobulin having the features described hereinbefore. Also contemplated by the invention are variants of naturally occurring antibodies which retain the CDRs but are presented in a different framework, as discussed hereinafter and which function in the same way, i.e. retain specificity for the antigen. Thus antibodies include functional equivalents or homologues in which naturally occurring domains have been replaced in part or in full with natural or non-natural equivalents or homologues which function in the same way.

When the specific binding molecule of the invention is an antibody, it is preferably a monoclonal antibody. By "monoclonal antibody" is meant an antibody preparation consisting of a single antibody species, i.e. all antibodies in the preparation have the same amino acid sequences, including the same CDRs, and thus bind the same epitope on their target antigen (by "target antigen" is meant the antigen containing the epitope bound by a particular antibody, i.e. the target antigen of an anti-Anx-A1 antibody is Anx-A1) with the same effect. In other words, the antibody of the invention is preferably not part of a polyclonal mix of antibodies.

In an antibody, as described above, the CDR sequences are located in the variable domains of the heavy and light chains. The CDR sequences sit within a polypeptide framework, which positions the CDRs appropriately for antigen binding. Thus the remainder of the variable domains (i.e. the parts of the variable domain sequences which do not form a part of any one of the CDRs) constitute framework regions. The N-terminus of a mature variable domain forms framework region 1 (FR1); the polypeptide sequence between CDR1 and CDR2 forms FR2; the polypeptide sequence between CDR2 and CDR3 forms FR3; and the polypeptide sequence linking CDR3 to the constant domain forms FR4. In an antibody of the invention the variable region framework regions may have any appropriate amino acid sequence such that the antibody binds to human Anx-A1 via its CDRs. The constant regions may be the constant regions of any mammalian (preferably human) antibody isotype.

In certain embodiments of the invention the specific binding molecule may be multi-specific, e.g. a bi-specific monoclonal antibody. A multi-specific binding molecule contains regions or domains (antigen-binding regions) which bind to at least two different molecular binding partners, e.g. bind to two or more different antigens or epitopes. In the case of a bi-specific antibody, the antibody comprises two heavy and light chains, in the formation as described above, except that the variable domains of the two heavy chains and the two light chains, respectively, are different, and thus form two different antigen-binding regions. In a multi-specific (e.g. bi-specific) binding molecule, e.g. monoclonal antibody, of the invention, one of the antigen-binding regions has the CDR sequences of a specific binding molecule of the invention as defined herein, and thus binds Anx-A1. The other antigen-binding region(s) of the multi-specific binding molecule of the invention are different to the antigen-binding regions formed by CDRs of the invention, e.g. have CDRs with sequences different to those defined herein for the specific binding molecule of the invention. The additional (e.g. second) antigen-binding region(s) of the specific binding molecule, e.g. in the bi-specific antibody, may also bind Anx-A1, but at a different epitope to the first antigen-binding region which binds to Anx-A1 (which has the CDRs of the specific binding molecule of the invention). Alternatively, the additional (e.g. second) antigen-binding region(s) may bind additional (e.g. a second), different antigen(s) which is(are) not Anx-A1. In an alternative embodiment, the two or more antigen-binding regions in the specific binding molecule, e.g. in an antibody, may each bind to the same antigen, i.e. provide a multivalent (e.g. bivalent) molecule.

The specific binding molecule may be an antibody fragment or synthetic construct capable of binding human Anx-A1. Antibody fragments are discussed in Rodrigo et al., Antibodies, Vol. 4(3), p. 259-277, 2015. Antibody fragments of the invention are preferably monoclonal (i.e. they are not part of a polyclonal mix of antibody fragments). Antibody fragments include, for example, Fab, $F(ab')_2$, Fab' and Fv fragments. Fab fragments are discussed in Roitt et al, Immunology second edition (1989), Churchill Livingstone, London. A Fab fragment consists of the antigen-binding domain of an antibody, i.e. an individual antibody may be seen to contain two Fab fragments, each consisting of a light chain and its conjoined N-terminal section of the heavy chain. Thus a Fab fragment contains an entire light chain and the $V_H$ and $C_H1$ domains of the heavy chain to which it is bound. Fab fragments may be obtained by digesting an antibody with papain.

$F(ab')_2$ fragments consist of the two Fab fragments of an antibody, plus the hinge regions of the heavy domains, including the disulphide bonds linking the two heavy chains together. In other words, a $F(ab')_2$ fragment can be seen as two covalently joined Fab fragments. $F(ab')_2$ fragments may be obtained by digesting an antibody with pepsin. Reduction of $F(ab')_2$ fragments yields two Fab' fragments, which can be seen as Fab fragments containing an additional sulfhydryl group which can be useful for conjugation of the fragment to other molecules.

Fv fragments consist of just the variable domains of the light and heavy chains. These are not covalently linked and are held together only weakly by non-covalent interactions. Fv fragments can be modified to produce a synthetic construct known as a single chain Fv (scFv) molecule. Such a modification is typically performed recombinantly, by engineering the antibody gene to produce a fusion protein in which a single polypeptide comprises both the $V_H$ and $V_L$ domains. scFv fragments generally include a peptide linker covalently joining the $V_H$ and $V_L$ regions, which contributes to the stability of the molecule. The linker may comprise from 1 to 20 amino acids, such as for example 1, 2, 3 or 4 amino acids, 5, 10 or 15 amino acids, or other intermediate numbers in the range 1 to 20 as convenient. The peptide linker may be formed from any generally convenient amino acid residues, such as glycine and/or serine. One example of a suitable linker is $Gly_4Ser$. Multimers of such linkers may be used, such as for example a dimer, a trimer, a tetramer or a pentamer, e.g. $(Gly_4Ser)_2$, $(Gly_4Ser)_3$, $(Gly_4Ser)_4$ or $(Gly_4Ser)_5$. However, it is not essential that a linker be present, and the $V_L$ domain may be linked to the $V_H$ domain by a peptide bond. An scFv is herein defined as an antibody fragment.

The specific binding molecule may be an analogue of an scFv. For example, the scFv may be linked to other specific binding molecules (for example other scFvs, Fab antibody fragments and chimeric IgG antibodies (e.g. with human frameworks)). The scFv may be linked to other scFvs so as to form a multimer which is a multi-specific binding protein, for example a dimer, a trimer or a tetramer. Bi-specific scFvs are sometimes referred to as diabodies, tri-specific scFvs as triabodies and tetra-specific scFvs as tetrabodies. In other embodiments the scFv of the invention may be bound to other, identical scFv molecules, thus forming a multimer which is mono-specific but multi-valent, e.g. a bivalent dimer or a trivalent trimer may be formed.

Synthetic constructs that can be used include CDR peptides. These are synthetic peptides comprising antigen-binding determinants. Peptide mimetics can also be used. These molecules are usually conformationally-restricted organic rings that mimic the structure of a CDR loop and that include antigen-interactive side chains.

As mentioned above, the CDR sequences of SEQ ID NOs: 1-6, upon which CDR sequences of the specific binding molecule of the invention are based, were initially identified in the murine antibody Mdx001. As mentioned, the Mdx001 light chain has the sequence of SEQ ID NO: 15 and the Mdx001 heavy chain has the sequence of SEQ ID NO: 16 (in both cases including the signal sequence, which correspond to the first 20 amino acids of SEQ ID NO: 15 and the first 19 amino acids of SEQ ID NO: 16, respectively). The light and heavy chain variable domains of Mdx001 have the sequences set forth in SEQ ID NOs: 18 and 19, respectively. In certain embodiments of the invention, the specific binding molecule may be an antibody comprising light and heavy chains comprising or having (consisting of) the sequences of SEQ ID NOs: 15 and 16, respectively, which may include or exclude the signal sequences, e.g. the specific binding molecule of the invention may be the Mdx001 antibody, or sequences with at least 70% (preferably at least 80, 90, 95, 96, 97, 98 or 99%) identity thereto (but satisfying the 85% sequence identity requirement for the CDRs). In other embodiments of the invention, the specific binding molecule may be an antibody fragment obtained from an antibody comprising light and heavy chains comprising or having the sequences of SEQ ID NOs: 15 and 16, respectively, which may include or exclude the signal sequence, e.g. it may be a Fab comprising the antigen-binding regions of such an antibody or an scFv comprising the variable regions of the light and heavy chains of such an antibody, e.g. comprising light chain variable domains and heavy chain variable domains comprising or having the sequences of SEQ ID NOs: 18 and 19, respectively, or sequences with at least 70% (preferably at least 80, 90, 95, 96, 97, 98 or 99%) identity thereto (but satisfying the 85% sequence identity requirement for the CDRs). Antibodies or antibody fragments with such sequences contain murine sequences. Preferably, however, the antibody or antibody fragment of the invention is modified to render it more suitable for therapeutic use in humans.

The antibody or antibody fragment of the invention may be a human/mouse chimeric antibody, or preferably may be humanised. This is particularly the case for monoclonal antibodies and antibody fragments. Humanised or chimeric antibodies or antibody fragments are desirable when the molecule is to be used as a human therapeutic. Therapeutic treatment of humans with murine antibodies can be ineffective for a number of reasons, e.g. a short in vivo half-life of the antibody; weak effector functions mediated by the mouse heavy chain constant region, due to low recognition of the murine heavy chain constant region by Fc receptors on human immune effector cells; patient sensitisation to the antibody, and generation of a human anti-mouse antibody (HAMA) response; and neutralisation of the mouse antibody by HAMA leading to loss of therapeutic efficacy.

A chimeric antibody is an antibody with variable regions derived from one species and constant regions derived from another. Thus an antibody or antibody fragment of the invention may be a chimeric antibody or chimeric antibody fragment, comprising murine variable domains and human constant domains. The murine light chain variable domain may be the Mdx001 light chain variable domain, which has the sequence set forth in SEQ ID NO: 18. Alternatively, the murine light chain variable domain may be a sequence with at least 70% (preferably at least 80, 90, 95, 96, 97, 98 or 99%) sequence identity to SEQ ID NO: 18, in which the CDR sequences VLCDR1-3 have at least 85% sequence identity to SEQ ID NOs: 1-3 respectively. The murine heavy chain variable domain may be the Mdx001 heavy chain variable domain, which has the sequence set forth in SEQ ID NO: 19. Alternatively, the murine heavy chain variable domain may be a sequence with at least 70% (preferably at least 80, 90, 95, 96, 97, 98 or 99%) sequence identity to SEQ ID NO: 19, in which the CDR sequences VHCDR1-3 have at least 85% sequence identity to SEQ ID NOs: 4-6 respectively.

As detailed above, the isotype of an antibody is defined by the sequence of its heavy chain constant regions. The chimeric antibody of the invention may have the constant regions of any human antibody isotype, and any sub-class within each isotype. For instance, the chimeric antibody may have the Fc regions of an IgA, IgD, IgE, IgG or IgM antibody (i.e. the chimeric antibody may comprise the constant domains of heavy chains $\alpha$, $\delta$, $\varepsilon$, $\gamma$, or $\mu$, respectively), though preferably the antibody of the invention is of the IgG isotype. Thus the chimeric antibody of the invention may be of any isotype. The light chain of the chimeric antibody may be either a $\kappa$ or $\lambda$ light chain, i.e. it may comprise the constant region of a human $\lambda$ light chain or a human $\kappa$ light chain. A chimeric antibody fragment is, correspondingly, an antibody fragment comprising constant domains (e.g. an Fab, Fab' or $F(ab')_2$ fragment). The constant domains of a chimeric antibody fragment of the invention may be as described above for a chimeric monoclonal antibody.

Chimeric antibodies may be generated using any suitable technique, e.g. recombinant DNA technology in which the DNA sequence of the murine variable domain is fused to the DNA sequence of the human constant domain(s) so as to encode a chimeric antibody. A chimeric antibody fragment may be obtained either by using recombinant DNA technology to produce a DNA sequence encoding such a polypeptide, or by processing a chimeric antibody of the invention to produce the desired fragments, as described above. Chimeric antibodies can be expected to overcome the problems of a short in vivo half-life and weak effector functions associated with using a murine antibody in human therapy, and may reduce the probability of patient sensitisation and HAMA occurring. However, patient sensitisation and HAMA may still occur when a chimeric antibody is administered to a human patient, due to the presence of murine sequences in the variable domains.

Preferably the antibody or antibody fragment of the invention is therefore fully humanised. A humanised antibody is an antibody derived from another species, e.g. a mouse, in which not only are the constant domains of the antibody chains replaced with human constant domains, but the amino acid sequences of the variable regions are modified, in particular to replace the foreign (e.g. murine) framework sequences with human framework sequences, such that, preferably, the only non-human sequences in the antibody are the CDR sequences. A humanised antibody can overcome all the problems associated with therapeutic use of a non-human antibody in a human, including avoiding or minimising the probability of patient sensitisation and HAMA occurring.

Antibody humanisation is generally performed by a process known as CDR grafting, though any other technique in the art may be used. Antibody grafting is well described in Williams, D. G. et al., Antibody Engineering Vol. 1, edited by R. Kontermann and S. Dübel, Chapter 21, pp. 319-339. In this process, a chimeric antibody as described above is first generated. Subsequent humanisation of the foreign, e.g. murine, variable domains involves intercalating the murine CDRs from each immunoglobulin chain within the FRs of the most appropriate human variable region. This is done by aligning the murine variable domains with databases of known human variable domains (e.g. IMGT or Kabat). Appropriate human framework regions are identified from the best aligned variable domains, e.g. domains with high sequence identity between the human and murine framework regions, domains containing CDRs of the same length, domains having the most similar structures (based on homology modelling), etc. The murine CDR sequences are then grafted into the lead human framework sequences at the appropriate locations using recombinant DNA technology, and the humanised antibodies then produced and tested for binding to the target antigen. The process of antibody humanisation is known and understood by the skilled individual, who can perform the technique without further instruction. Antibody humanisation services are also offered by a number of commercial companies, e.g. GenScript (USA/China) or MRC Technology (UK). Humanised antibody fragments can be easily obtained from humanised antibodies, as described above.

Thus the antibody or antibody fragment of the invention may be derived from any species, e.g. it may be a murine antibody or antibody fragment. It is preferred, however, that the antibody or antibody fragment is a chimeric antibody or antibody fragment, i.e. that only the variable domains of the antibody or antibody fragment are non-human, and the constant domains are all human. Optimally, the antibody or antibody fragment of the invention is a humanised antibody or antibody fragment.

Humanised versions of Mdx001 have been developed by the inventors, namely MDX-L1H4 and MDX-L2H2, as described hereinbefore. Preferred variants are also provided in which the VLCDR1 has a sequence as set forth in SEQ ID NO: 36 (variant 1) or 37 (variant 2). As detailed above, the antibody of the invention may comprise a VLCDR1 with the amino acid sequence set forth in SEQ ID NO: 36 or 37 (or an amino acid sequence with at least 85% sequence identity thereto), and such an antibody has enhanced stability, and may bind Anx-A1 with a higher affinity, than an equivalent antibody comprising a VLCDR1 of SEQ ID NO: 1. Thus an antibody comprising one of these modified VLCDR1 sequences has improved functionality relative to an equivalent antibody comprising a VLCDR1 of SEQ ID NO: 1. These humanised antibodies have been named MDX-L1M2H4, MDX-L1M3H4, MDX-L2M2H2 and MDX-L2M3H2, as described above. MDX-L1H4 and MDX-L2H2 are of the IgG isotype, specifically sub-class IgG1. Since they are humanised, they can be administered to a human patient more safely and with fewer side effects than can Mdx001.

As detailed above, the CDRs of an antibody determine its binding specificity, i.e. the target(s) to which it binds and the affinity with which it binds its target(s). Alteration of an antibody's CDR sequences may damage or abrogate binding of an antibody to its target. Unexpectedly, humanised versions of Mdx001 which comprise a VLCDR1 with the sequence of SEQ ID NO: 36 or 37 have improved affinity for Anx-A1, relative to Mdx001. As demonstrated in the Examples below, MDX-L1M2H4 and MDX-L2M2H2, respectively, have improved $K_D$ values for Anx-A1 binding relative to Mdx001 (indeed MDX-L1M2H4 has a $K_D$ value for Anx-A1 less than half that of Mdx001), meaning that they bind Anx-A1 with higher affinity than does Mdx001 (indeed MDX-L1M2H4 binds Anx-A1 with more than double the affinity of Mdx001). This improvement in target affinity corresponds to an improvement in therapeutic potential for the variants of MDX-L1H4 and MDX-L2H2 relative to Mdx001.

Thus in a particular embodiment, the invention provides a humanised antibody or fragment thereof comprising a VLCDR1 having the amino acid sequence set forth in SEQ ID NO: 36 or 37, and VLCDRs2-3 and VHCDRs1-3 having the amino acid sequences set forth in SEQ ID NOs: 2-6, respectively.

MDX-L1H4 comprises a humanised light chain with the amino acid sequence set forth in SEQ ID NO: 40 and a humanised heavy chain with the amino acid sequence set forth in SEQ ID NO: 41. MDX-L2H2 comprises a humanised light chain with the amino acid sequence set forth in SEQ ID NO: 42 and a humanised heavy chain with the amino acid sequence set forth in SEQ ID NO: 43. As is known to the skilled person, antibody chains are produced in nature with signal sequences. Antibody signal sequences are amino acid sequences located at the N-termini of the light and heavy chains, N-terminal to the variable regions. The signal sequences direct the antibody chains for export from the cell in which they are produced. The amino acid sequences of SEQ ID NOs: 40-43 each comprise a signal sequence. The signal sequence of the light chain of both MDX-L1H4 and MDX-L2H2 is set forth in SEQ ID NO: 52, which corresponds to the first 20 amino acids of SEQ ID NO: 40 and SEQ ID NO: 42; the signal sequence of the heavy chain of both MDX-L1H4 and MDX-L2H2 is set forth in SEQ ID NO: 53, which corresponds to the first 19 amino acids of SEQ ID NO: 41 and SEQ ID NO: 43.

The light chain of MDX-L1M2H4 has the amino acid sequence set forth in SEQ ID NO: 44, and the light chain of MDX-L1M3H4 has the amino acid sequence set forth in SEQ ID NO: 46. The heavy chain of MDX-L1M2H4 and MDX-L1M3H4 is unaltered relative to MDX-L1H4, i.e. MDX-L1M2H4 and MDX-L1M3H4 both comprise a heavy chain with the amino acid sequence set forth in SEQ ID NO: 41. The variable region of the light chain of MDX-L1M2H4 has the amino acid sequence set forth in SEQ ID NO: 48, and the variable region of MDX-L1M3H4 has the amino acid sequence set forth in SEQ ID NO: 49.

The light chain of MDX-L2M2H2 has the amino acid sequence set forth in SEQ ID NO: 45, and the light chain of MDX-L2M3H2 has the amino acid sequence set forth in SEQ ID NO: 47. The heavy chain of MDX-L2M2H2 and MDX-L2M3H2 is unaltered relative to MDX-L2H2, i.e. MDX-L2M2H2 and MDX-L2M3H2 both comprise a heavy chain with the amino acid sequence set forth in SEQ ID NO: 43. The variable region of the light chain of MDX-L2M2H2 has the amino acid sequence set forth in SEQ ID NO: 50, and the variable region of MDX-L2M3H2 has the amino acid sequence set forth in SEQ ID NO: 51.

As is also known to the skilled individual, the signal sequence is cleaved from an antibody chain upon export of the protein from the cell in which it is synthesised. Cleavage of the signal sequence can be referred to as maturation of an antibody chain; functional, circulating antibodies which have been exported from the cells in which they were made comprise mature heavy and light chains lacking signal sequences. The mature MDX-L1H4 light chain has the amino acid sequence set forth in SEQ ID NO: 75, the mature MDX-L1M2H4 light chain has the amino acid sequence set forth in SEQ ID NO: 54, the mature MDX-L1M3H4 light chain has the amino acid sequence set forth in SEQ ID NO: 76 and the mature MDX-L1H4 heavy chain has the amino acid sequence set forth in SEQ ID NO: 55 (which is the same in all variants and the parent MDX-L1H4 sequence).

The mature MDX-L2H2 light chain has the amino acid sequence set forth in SEQ ID NO: 77, the mature MDX-L2M2H2 light chain has the amino acid sequence set forth in SEQ ID NO: 78, the mature MDX-L2M3H2 light chain has the amino acid sequence set forth in SEQ ID NO: 79 and the mature MDX-L2H2 heavy chain has the amino acid sequence set forth in SEQ ID NO: 80 (which is the same in all variants and the parent MDX-L2H2 sequence).

In a particular embodiment of the invention, the specific binding molecule comprises:

(i) a light chain variable region comprising or consisting of the amino acid sequence set forth in SEQ ID NO: 32, 34 or 48-51, or a variant thereof having at least 70% (preferably at least 80, 90, 95, 96, 97, 98 or 99%) sequence identity thereto, and in which the CDR sequences VLCDR1-3 have at least 85% sequence identity to SEQ ID NOs: 1, 36 or 37 and 2-3 respectively; and (ii) a heavy chain variable region comprising or consisting of the amino acid sequence set forth in SEQ ID NO: 33 or 35, or a variant thereof having at least 70% (preferably at least 80, 90, 95, 96, 97, 98 or 99%) sequence identity thereto and in which the CDR sequences VHCDR1-3 have at least 85% sequence identity to SEQ ID NOs: 4-6 respectively. Such a specific binding molecule may be an antibody (in particular a monoclonal antibody), or may for example be an antibody fragment as discussed above, for instance a Fab, $F(ab)_2$, Fab', Fv or scFv.

The specific binding molecule may be a humanised monoclonal antibody comprising the light and heavy chains of MDX-L1H4 or MDX-L2H2 or variants thereof. In the antibody, the light and heavy chains may include or exclude the signal sequences. The specific binding molecule may thus comprise:

(i) a light chain comprising or consisting of the amino acid sequence set forth in SEQ ID NO: 40, 42, 44-47, 54 or 75-79, or an amino acid sequence having at least 70% (preferably at least 80, 90, 95, 96, 97, 98 or 99%) sequence identity thereto and in which the CDR sequences VLCDR1-3 have at least 85% sequence identity to SEQ ID NOs: 1, 36 or 37 and 2-3 respectively; and (ii) a heavy chain comprising or consisting of the amino acid sequence set forth in SEQ ID NO: 41, 43, 55 or 80, or an amino acid sequence having at least 70% (preferably at least 80, 90, 95, 96, 97, 98 or 99%) sequence identity to thereto and in which the CDR sequences VHCDR1-3 have at least 85% sequence identity to SEQ ID NOs: 4-6 respectively.

In a preferred embodiment the specific binding molecule comprises:

(i) a light chain comprising or consisting of the amino acid sequence set forth in SEQ ID NO: 40, 44, 46, 54, 75 or 76, or an amino acid sequence having at least 70% (preferably at least 80, 90, 95, 96, 97, 98 or 99%) sequence identity thereto and in which the CDR sequences VLCDR1-3 have at least 85% sequence identity to SEQ ID NOs: 1, 36 or 37 and 2-3 respectively; and (ii) a heavy chain comprising or consisting of the amino acid sequence set forth in SEQ ID NO: 41 or 55, or an amino acid sequence having at least 70% (preferably at least 80, 90, 95, 96, 97, 98 or 99%) sequence identity to thereto and in which the CDR sequences VHCDR1-3 have at least 85% sequence identity to SEQ ID NOs: 4-6 respectively.

In another preferred embodiment, the specific binding molecule comprises:

(i) a light chain comprising or consisting of the amino acid sequence set forth in SEQ ID NO: 42, 45, 47 or 77-79, or an amino acid sequence having at least 70% (preferably at least 80, 90, 95, 96, 97, 98 or 99%) sequence identity thereto and in which the CDR sequences VLCDR1-3 have at least 85% sequence identity to SEQ ID NOs: 1, 36 or 37 and 2-3 respectively; and (ii) a heavy chain comprising or consisting of the amino acid sequence set forth in SEQ ID NO: 43 or 80, or an amino acid sequence having at least 70% (preferably at least 80, 90, 95, 96, 97, 98 or 99%) sequence identity to thereto and in which the CDR sequences VHCDR1-3 have at least 85% sequence identity to SEQ ID NOs: 4-6 respectively.

In another preferred embodiment, the specific binding molecule comprises:

(i) a light chain comprising or consisting of the amino acid sequence set forth in SEQ ID NO: 54, 75 or 76, or an amino acid sequence having at least 70% (preferably at least 80, 90, 95, 96, 97, 98 or 99%) sequence identity thereto and in which the CDR sequences VLCDR1-3 have at least 85% sequence identity to SEQ ID NOs: 1, 36 or 37 and 2-3 respectively; and (ii) a heavy chain comprising or consisting of the amino acid sequence set forth in SEQ ID NO: 55, or an amino acid sequence having at least 70% (preferably at least 80, 90, 95, 96, 97, 98 or 99%) sequence identity to thereto and in which the CDR sequences VHCDR1-3 have at least 85% sequence identity to SEQ ID NOs: 4-6 respectively.

In another preferred embodiment, the specific binding molecule comprises:

(i) a light chain comprising or consisting of the amino acid sequence set forth in SEQ ID NO: 77-79, or an amino acid sequence having at least 70% (preferably at least 80, 90, 95, 96, 97, 98 or 99%) sequence identity thereto and in which the CDR sequences VLCDR1-3 have at least 85% sequence identity to SEQ ID NOs: 1, 36 or 37 and 2-3 respectively; and (ii) a heavy chain comprising or consisting of the amino acid sequence set forth in SEQ ID NO: 80, or an amino acid sequence having at least 70% (preferably at least 80, 90, 95, 96, 97, 98 or 99%) sequence identity to thereto and in which the CDR sequences VHCDR1-3 have at least 85% sequence identity to SEQ ID NOs: 4-6 respectively.

In a particular embodiment, the specific binding molecule is an antibody comprising a light chain comprising or consisting of the amino acid sequence set forth in SEQ ID NO: 40 and a heavy chain comprising or consisting of the amino acid sequence set forth in SEQ ID NO: 41.

In another embodiment, the specific binding molecule is an antibody comprising a light chain comprising or consisting of the amino acid sequence set forth in SEQ ID NO: 42 and a heavy chain comprising or consisting of the amino acid sequence set forth in SEQ ID NO: 43.

In another embodiment, the specific binding molecule is an antibody comprising a light chain comprising or consisting of the amino acid sequence set forth in SEQ ID NO: 44 and a heavy chain comprising or consisting of the amino acid sequence set forth in SEQ ID NO: 41.

In another embodiment, the specific binding molecule is an antibody comprising a light chain comprising or consisting of the amino acid sequence set forth in SEQ ID NO: 45 and a heavy chain comprising or consisting of the amino acid sequence set forth in SEQ ID NO: 43.

In another embodiment, the specific binding molecule is an antibody comprising a light chain comprising or consisting of the amino acid sequence set forth in SEQ ID NO: 46 and a heavy chain comprising or consisting of the amino acid sequence set forth in SEQ ID NO: 41.

In another embodiment, the specific binding molecule is an antibody comprising a light chain comprising or consisting of the amino acid sequence set forth in SEQ ID NO: 47 and a heavy chain comprising or consisting of the amino acid sequence set forth in SEQ ID NO: 43.

In another embodiment, the specific binding molecule is an antibody comprising a light chain comprising or consisting of the amino acid sequence set forth in SEQ ID NO: 54 and a heavy chain comprising or consisting of the amino acid sequence set forth in SEQ ID NO: 55.

In another embodiment, the specific binding molecule is an antibody comprising a light chain comprising or consisting of the amino acid sequence set forth in SEQ ID NO: 75 and a heavy chain comprising or consisting of the amino acid sequence set forth in SEQ ID NO: 55.

In another embodiment, the specific binding molecule is an antibody comprising a light chain comprising or consisting of the amino acid sequence set forth in SEQ ID NO: 76 and a heavy chain comprising or consisting of the amino acid sequence set forth in SEQ ID NO: 55.

In another embodiment, the specific binding molecule is an antibody comprising a light chain comprising or consisting of the amino acid sequence set forth in SEQ ID NO: 77 and a heavy chain comprising or consisting of the amino acid sequence set forth in SEQ ID NO: 80.

In another embodiment, the specific binding molecule is an antibody comprising a light chain comprising or consisting of the amino acid sequence set forth in SEQ ID NO: 78 and a heavy chain comprising or consisting of the amino acid sequence set forth in SEQ ID NO: 80.

In another embodiment, the specific binding molecule is an antibody comprising a light chain comprising or consisting of the amino acid sequence set forth in SEQ ID NO: 79 and a heavy chain comprising or consisting of the amino acid sequence set forth in SEQ ID NO: 80.

The specific binding molecule of the invention preferably binds Anx-A1 with a high affinity. As is known to the skilled person, the affinity of a binding molecule for its ligand (or binding partner), such as the affinity of an antibody for its target antigen, can be quantitatively defined by the dissociation constant ($K_d$) for a complex of the binding molecule and ligand. The $K_d$ value of a specific binding molecule, e.g. an antibody, corresponds to the ratio of the binding molecule dissociation rate (i.e. how quickly it dissociates from its ligand) to the binding molecule association rate (i.e. how quickly it binds its ligand). A lower $K_d$ value corresponds to a higher binding affinity of the binding molecule for its ligand. Preferably, the specific binding molecule of the present invention binds Anx-A1 with a $K_d$ of less than 20 nM, preferably less than 15 nM or 10 nM. By Anx-A1 herein is meant any of the human isoforms of Anx-A1. In particular, it may refer to the isoform ANXA1-003.

It is preferred that any specific binding molecule of the invention binds Anx-A1 with a $K_d$ of less than 20 nM, preferably less than 15 nM or 10 nM. This is particularly the case if the specific binding molecule of the invention is an antibody. However, if the specific binding molecule of the invention is an antibody fragment, e.g. an scFv, in some embodiments it may bind Anx-A1 with a slightly lower affinity than this, i.e. its $K_d$ of Anx-A1 binding may be higher than 10 nM, 15 nM or 20 nM, e.g. less than 40 nM, but preferably less than 20 nM.

The $K_d$ of the binding of the specific binding molecule to Anx-A1 is preferably measured under binding conditions identified as optimal for the antibody Mdx001, by which is meant conditions under which $Ca^{2+}$ ions are present at a concentration of at least 1 mM, and optionally HEPES is present at a concentration of from 10-20 mM, and the pH is between 7 and 8, preferably of a physiological level between 7.2 and 7.5 inclusive. NaCl may be present, e.g. at a concentration of from 100-250 mM, and a low concentration of a detergent, e.g. polysorbate 20, may also be present. Such a low concentration may be e.g. from 0.01 to 0.5% v/v. Conveniently methods as described in the Examples may be used. Alternatively, any other conditions identified as promoting the binding of the specific binding molecule of the invention to human Anx-A1 may be used.

A number of methods by which the $K_d$ of an interaction between a specific binding molecule and its ligand may be calculated are well-known in the art. Known techniques include SPR (e.g. Biacore) and polarization-modulated oblique-incidence reflectivity difference (OI-RD).

A specific binding molecule with high affinity for its ligand is advantageous in the present invention, as, generally, less of a specific binding molecule with high affinity for its ligand is required to achieve a particular effect than of a specific binding molecule with lower affinity for the same ligand. For instance, if the specific binding molecule is for therapeutic use, it can be expected that a lower dosage would be required of a specific binding molecule with high affinity for its ligand than of a specific binding molecule with lower affinity for the same ligand. This may be advantageous for the patient, who might require fewer or smaller doses of the specific binding molecule, e.g. antibody, and would also be more economical, as less of the specific binding molecule would be required for the therapy.

The invention also provides a preparation comprising the specific binding molecule described above. At least 90% of the specific binding molecules in the preparation that bind to human Anx-A1 bind with a $K_d$ of less than 20 nM, preferably less than 15 nM or 10 nM. Techniques by which $K_d$ of the binding molecule may be measured, and conditions under which the $K_d$ may be measured, are described above. In an alternative embodiment a preparation is provided comprising the specific binding molecule of the invention in which at least 90% of the specific binding molecules in the preparation that bind to human Anx-A1 have the CDRs as described hereinbefore, and preferably contain two copies of the CDRs in each molecule (e.g. in an antibody). In a yet further embodiment a preparation is provided comprising the specific binding molecule of the invention in which the specific binding molecule is an antibody or fragment thereof and at least 90% of the antibodies or fragments in said preparation are said antibodies or fragments of the invention (i.e. contain the CDRs as described hereinbefore, preferably contain two copies of the CDRs described hereinbefore). Further preferred preparations according to the invention comprise antibody fragments, monoclonal antibodies or their fragments, chimeric antibodies or their fragments, or humanized antibodies or their fragments, of the invention.

The term "preparation" as used herein means a product (e.g. a solution or composition) containing at least the isolated specific binding molecule of the invention. The preparation should be made up in a form in which the specific binding molecule may be stably stored, i.e. a form in which the specific binding molecule does not degrade or become denatured, or lose its structure or activity. Suitable conditions in which an antibody may be stored are well known to the skilled person. The preparation of the invention may be a liquid preparation (i.e. a solution), such as an aqueous preparation (i.e. a solution made up in water) or a preparation made up in solvent, such as one or more organic solvents, or primarily in a solvent. Such a solvent may be polar or non-polar. Alternatively, the preparation may be a powder, such a lyophilised powder, or may be in any other suitable form for the storage of a specific binding molecule. These options apply also to compositions of the invention.

At least 90% of the specific binding molecules in the preparation that bind to human Anx-A1 bind with a $K_d$ of less than 20 nM, preferably less than 15 nM or 10 nM. Preferably at least 95%, 96%, 97%, 98% or 99% of the specific binding molecules in the preparation that bind to human Anx-A1 bind with a $K_d$ of less than 20 nM, 15 nM or 10 nM. In this embodiment the specific binding molecule has the definition described hereinbefore but is not necessarily a specific binding molecule of the invention, i.e. all specific binding molecules which bind human Anx-A1 are assessed to determine if at least 90% have the required $K_d$. Preferably the specific binding molecules to be assessed are antibodies or their fragments. By human Anx-A1 is meant any of the human isoforms of Anx-A1. In particular, it may refer to the isoform ANXA1-003. The skilled person is able to calculate the $K_d$ of the binding of a specific binding molecule to its ligand. Conditions under which the $K_d$ of specific binding molecules of the invention may be calculated, and methods by which this may be achieved, are mentioned above. By 90% is meant 90% of the number of specific binding molecules which bind Anx-A1 (i.e. 9 out of 10 specific binding molecules which Anx-A1), not 90% w/w. As noted, at least 90% of the specific binding molecules which bind Anx-A1 bind with a $K_d$ of less than 20 nM, preferably less than 15 nM or 10 nM. This does not preclude that the preparation contains any concentration of specific binding molecules which bind other antigens. This thus provides a preparation in which the molecules which bind to human Anx-A1 are largely uniform, i.e. have similar functionality.

The preparation (and composition) of the invention may contain additives, which may be advantageous for storage of a specific binding molecule such as an antibody or antibody fragment. For instance, if the preparation is a liquid, the preparation may advantageously comprise a high concentration of a cryoprotective agent, such as glycerol or ethylene glycol, e.g. at least 20%, at least 25%, at least 30%, at least 40% or at least 50% glycerol or ethylene glycol. A cryoprotective agent prevents the preparation from freezing at low temperature, protecting the specific binding molecule from ice damage during storage. Concentrated sucrose (e.g. at least 250 mM, at least 500 mM, at least 750 mM or at least 1M sucrose) may advantageously be comprised within a liquid preparation. Liquid preparations may also comprise one or more antioxidants, e.g. 3-mercaptoethanol or dithiothreitol, one or more metal chelating agents, e.g. ethylenediaminetetraacetic acid (EDTA), and one or more carrier proteins, particularly bovine serum albumin (BSA). The liquid preparation may preferably comprise up to 1% BSA, e.g. 0.1-0.5% BSA. The preparation of the invention may be at a pH of 5-8, e.g. 6-8, 7-8 or 7-7.5. The pH may be maintained by addition of a buffer to the preparation, e.g. Tris (i.e. tris(hydroxymethyl)aminomethane), HEPES or MOPS. For instance, the preparation may contain 5-50 mM HEPES, e.g. 10-20 mM HEPES. Lyophilised preparations (or compositions) of the invention may contain one or more stabilisers, such as a polyol, e.g. glycerol or sorbitol, and/or a sugar, e.g. sucrose, trehalose or mannitol. The preparation may also contain additional components as described for compositions described hereinafter.

The invention also provides a nucleic acid molecule which comprises a nucleotide sequence encoding a specific binding molecule of the invention. Thus the invention provides a nucleic acid molecule comprising nucleotide sequences which encode CDR sequences as defined above, i.e. the nucleic acid molecule of the invention comprises a nucleotide sequence which comprises the following:

a nucleotide sequence VLCDR1 which encodes the amino acid sequence set forth in SEQ ID NO: 1, 36 or 37 or an amino sequence with at least 85%, 90% or 95% sequence identity thereto;

a nucleotide sequence VLCDR2 which encodes the amino acid sequence set forth in SEQ ID NO: 2 or an amino sequence with at least 85%, 90% or 95% sequence identity thereto;

a nucleotide sequence VLCDR3 which encodes the amino acid sequence set forth in SEQ ID NO: 3 or an amino sequence with at least 85%, 90% or 95% sequence identity thereto;

a nucleotide sequence VHCDR1 which encodes the amino acid sequence set forth in SEQ ID NO: 4 or an amino sequence with at least 85%, 90% or 95% sequence identity thereto;

a nucleotide sequence VHCDR2 which encodes the amino acid sequence set forth in SEQ ID NO: 5 or an amino sequence with at least 85%, 90% or 95% sequence identity thereto; and a nucleotide sequence VHCDR3 which encodes the amino acid sequence set forth in SEQ ID NO: 6 or an amino sequence with at least 85%, 90% or 95% sequence identity thereto.

The nucleotide sequence VLCDR1 may have the nucleotide sequence set forth in SEQ ID NO: 20, 85 or 86 (which each encode SEQ ID NO: 1), a nucleotide sequence degenerate with SEQ ID NO: 20, 85 or 86 or a nucleotide sequence with at least 85%, 90% or 95% sequence identity to SEQ ID NO: 20, 85 or 86. SEQ ID NO: 20 is the VLCDR1 DNA sequence of Mdx001, SEQ ID NO: 85 is the VLCDR1 DNA sequence of MDX-L1H4 and SEQ ID NO: 86 is the VLCDR1 DNA sequence of MDX-L2H2.

Alternatively the nucleotide sequence VLCDR1 may have the nucleotide sequence set forth in SEQ ID NO: 65 or SEQ ID NO: 66 (which each encode SEQ ID NO: 36), a nucleotide sequence degenerate with SEQ ID NO: 65 or 66 or a nucleotide sequence with at least 85%, 90% or 95% sequence identity to SEQ ID NO: 65 or 66. SEQ ID NO: 65 is the VLCDR1 DNA sequence of MDX-L1M2H4 and SEQ ID NO: 66 is the VLCDR1 DNA sequence of MDX-L2M2H2.

Alternatively the nucleotide sequence VLCDR1 may have the nucleotide sequence set forth in SEQ ID NO: 87 or 88 (which each encode SEQ ID NO: 37), a nucleotide sequence degenerate with SEQ ID NO: 87 or 88 or a nucleotide sequence with at least 85%, 90% or 95% sequence identity to SEQ ID NO: 87 or 88. SEQ ID NO: 87 is the VLCDR1 DNA sequence of MDX-L1M3H4 and SEQ ID NO: 88 is the VLCDR1 DNA sequence of MDX-L2M3H2.

The nucleotide sequence VLCDR2 may have the nucleotide sequence set forth in SEQ ID NO: 21 or 67, a nucleotide sequence degenerate with SEQ ID NO: 21 or 67 or a nucleotide sequence with at least 85%, 90% or 95% sequence identity to SEQ ID NO: 21 or 67. SEQ ID NO: 21 is the VLCDR2 DNA sequence of Mdx001; SEQ ID NO: 67 is the VLCDR2 DNA sequence of MDX-L1H4 and MDX-L2H2 (including the variants of MDX-L1H4 and MDX-L2H2 MDX-L1M2H4, MDX-L1M3H4, MDX-L2M2H2 and MDX-L2M3H2).

The nucleotide sequence VLCDR3 may have the nucleotide sequence set forth in SEQ ID NO: 22, 68 or 69, a nucleotide sequence degenerate with SEQ ID NO: 22, 68 or 69 or a nucleotide sequence with at least 85, 90% or 95% sequence identity to SEQ ID NO: 22, 68 or 69. SEQ ID NO: 22 is the VLCDR3 DNA sequence of Mdx001; SEQ ID NO: 68 is the VLCDR3 DNA sequence of MDX-L1H4 (including its variants MDX-L1M2H4 and MDX-L1M3H4); SEQ ID NO: 69 is the VLCDR3 DNA sequence of MDX-L2H2 (including its variants MDX-L2M2H2 and MDX-L2M3H2).

The nucleotide sequence VHCDR1 may have the nucleotide sequence set forth in SEQ ID NO: 23, 70 or 71, a nucleotide sequence degenerate with SEQ ID NO: 23, 70 or 71 or a nucleotide sequence with at least 85%, 90% or 95% sequence identity to SEQ ID NO: 23, 70 or 71. SEQ ID NO: 23 is the VHCDR1 DNA sequence of Mdx001; SEQ ID NO: 70 is the VHCDR1 DNA sequence of MDX-L1H4 (including its variants MDX-L1M2H4 and MDX-L1M3H4); SEQ ID NO: 71 is the VHCDR1 DNA sequence of MDX-L2H2 (including its variants MDX-L2M2H2 and MDX-L2M3H2).

The nucleotide sequence VHCDR2 may have the nucleotide sequence set forth in SEQ ID NO: 24 or 72, a nucleotide sequence degenerate with SEQ ID NO: 24 or 72 or a nucleotide sequence with at least 85, 90% or 95% sequence identity to SEQ ID NO: 24 or 72. SEQ ID NO: 24 is the VHCDR2 DNA sequence of Mdx001; SEQ ID NO: 72 is the VHCDR2 DNA sequence of MDX-L1H4 and MDX-L2H2 (including their variants MDX-L1M2H4, MDX-L1M3H4, MDX-L2M2H2 and MDX-L2M3H2).

The nucleotide sequence VHCDR3 may have the nucleotide sequence set forth in SEQ ID NO: 25, 73 or 74, a nucleotide sequence degenerate with SEQ ID NO: 25, 73 or 74 or a nucleotide sequence with at least 85%, 90% or 95% sequence identity to SEQ ID NO: 25, 73 or 74. SEQ ID NO: 25 is the VHCDR3 DNA sequence of Mdx001; SEQ ID NO: 73 is the VHCDR3 DNA sequence of MDX-L1H4 (including its variants MDX-L1M2H4 and MDX-L1M3H4); SEQ ID NO: 74 is the VHCDR3 DNA sequence of MDX-L2H2 (including its variants MDX-L2M2H2 and MDX-L2M3H2). (In preferred aspects in relation to preferred nucleotide sequences, the nucleotide sequences may have at least 96, 97, 98 or 99% sequence identity to SEQ ID NOs: 20-25 or 65-74.)

It will be appreciated by those of ordinary skill in the art that, as a result of the degeneracy of the genetic code, there are many nucleotide sequences that may encode any given amino acid sequences, such as a CDR as described herein. By degenerate nucleotide sequences is meant two (or more) nucleotide sequences which encode the same protein (or protein sequence), specifically in the open reading frame of the reference nucleotide sequence which begins at position 1 (i.e. in which codon 1 of the encoding sequence corresponds to positions 1-3 of the reference nucleotide sequence). Thus, for example, a nucleotide sequence degenerate with SEQ ID NO. 20 is a nucleotide sequence which is different to SEQ ID NO. 20 but which, due to the degeneracy of the genetic code, encodes the same protein sequence as SEQ ID NO. 20, i.e. the CDR amino acid sequence of SEQ ID NO. 1.

The sequences for each CDR are provided in the nucleic acid molecule of the invention. These sequences are preferably provided with appropriate linker sequences between them, which when expressed provide the appropriate framework for presentation of the CDRs such that they bind the target epitope. The CDRs for the heavy and light chains may be presented such that, on expression, they are expressed on different polypeptides. In some embodiments of the invention the CDRs for the heavy and light chains may be provided on separate nucleic acid molecules. Such a pair of molecules form a further aspect of the invention. Constructs, vectors and host cells described hereinafter may incorporate or comprise a single nucleic acid molecule comprising all CDRs or two separate nucleic acid molecules comprising, separately, the CDRs for the heavy and light chains.

The nucleotide sequence encoding the specific binding molecule of the invention may preferably encode an antibody or a fragment thereof. Such an antibody or fragment thereof comprises the variable domains of the heavy and light chains of said antibody or antibody fragment. In this embodiment, the nucleotide sequence preferably encodes the sequences of the variable domains of the Mdx001 (or MDX-L1H4 or MDX-L2H2 or their variants) antibody, i.e. the nucleic acid molecule of the invention preferably comprises a nucleotide sequence encoding a light chain variable domain with the sequence of SEQ ID NO: 18 (or 32, 34, 48, 49, 50 or 51), or an amino acid sequence with at least 70%, 80%, 90% or 95% sequence identity thereto, and a heavy chain variable domain with the sequence of SEQ ID NO: 19 (or 33 or 35), or an amino acid sequence with at least 70%, 80%, 90% or 95% sequence identity thereto.

The nucleic acid molecule of the invention may be an isolated nucleic acid molecule and may further include DNA or RNA or chemical derivatives of DNA or RNA. The term "nucleic acid molecule" specifically includes single and double stranded forms of DNA and RNA.

Methods for preparing a nucleic acid molecule encoding a specific binding molecule of the invention are well known in the art, e.g. conventional polymerase chain reaction (PCR) cloning techniques can be used to construct the nucleic acid molecule of the invention. The nucleotide sequence encoding the specific binding molecule of the invention may be codon-optimised for expression in cells of a particular type or origin, e.g. the sequence may be hamster-optimised for expression in CHO cells.

In particular embodiments of the invention the nucleic acid molecule of the invention thus comprises nucleotide sequences which encode the variable domains of the light and heavy chains of Mdx001. In particular, the nucleotide sequences may be codon-optimised for expression in hamster cells, specifically CHO cells. In this embodiment, the nucleotide sequence of the light chain variable domain may be SEQ ID NO: 28 and the nucleotide sequence of the heavy chain variable domain may be SEQ ID NO: 29 or sequences with at least 70%, 80%, 90% or 95% sequence identity thereto. In an alternative embodiment the complete light chain and complete heavy chain nucleotide sequences may be codon-optimised, for example the light chain and heavy chain may have or comprise the nucleotide sequences set forth in SEQ ID NO: 30 and SEQ ID NO: 31, respectively, which may include or exclude the sequences encoding the signal sequences, or sequences with at least 70%, 80%, 90% or 95% sequence identity thereto.

In another preferred embodiment of the invention, the nucleotide sequence encoding the specific binding molecule of the invention encodes an antibody or fragment thereof comprising the light and heavy chains of MDX-L1H4, MDX-L2H2 or their variants MDX-L1M2H4, MDX-L1M3H4, MDX-L2M2H2 or MDX-L2M3H2, or the variable regions or CDRs thereof. The light chain of MDX-L1H4 is encoded by the nucleotide sequence set forth in SEQ ID NO: 81, the light chain of MDX-L1M2H4 is encoded by the nucleotide sequence set forth in SEQ ID NO: 57, and the light chain of MDX-L1M3H4 is encoded by the nucleotide sequence set forth in SEQ ID NO: 89; the heavy chain of MDX-L1H4 (including its variants MDX-L1M2H4 and MDX-L1M3H4) is encoded by the nucleotide sequence set forth in SEQ ID NO: 58. The variable region of the MDX-L1H4 light chain is encoded by the nucleotide sequence set forth in SEQ ID NO: 82, the variable region of the MDX-L1M2H4 light chain is encoded by the nucleotide sequence set forth in SEQ ID NO: 59, and the variable region of the MDX-L1M3H4 light chain is encoded by the nucleotide sequence set forth in SEQ ID NO: 90; the variable region of the MDX-L1H4 heavy chain is encoded by the nucleotide sequence set forth in SEQ ID NO: 60.

The light chain of MDX-L2H2 is encoded by the nucleotide sequence set forth in SEQ ID NO: 83, the light chain of MDX-L2M2H2 is encoded by the nucleotide sequence set forth in SEQ ID NO: 61, and the light chain of MDX-L2M3H2 is encoded by the nucleotide sequence set forth in SEQ ID NO: 91; the heavy chain of MDX-L2H2 (including its variants MDX-L2M2H2 and MDX-L2M3H2) is encoded by the nucleotide sequence set forth in SEQ ID NO: 62. The variable region of the MDX-L2H2 light chain is encoded by the nucleotide sequence set forth in SEQ ID NO: 84, the variable region of the MDX-L2M2H2 light chain is encoded by the nucleotide sequence set forth in SEQ ID NO: 63, and the variable region of the MDX-L2M3H2 light chain is encoded by the nucleotide sequence set forth in SEQ ID NO: 92; the variable region of the MDX-L2H2 heavy chain is encoded by the nucleotide sequence set forth in SEQ ID NO: 64.

Thus the nucleic acid molecule of the invention may comprise a nucleotide sequence encoding the light chain variable region of MDX-L1H4 or MDX-L2H2 or their variants MDX-L1M2H4, MDX-L1M3H4, MDX-L2M2H2 or MDX-L2M3H2, or a variant thereof, and a nucleotide sequence encoding the heavy chain variable region of MDX-L1H4 or MDX-L2H2, or a variant thereof. The nucleotide sequence encoding the light chain variable region of MDX-L1H4 or MDX-L2H2 or their variants MDX-L1M2H4, MDX-L1M3H4, MDX-L2M2H2 or MDX-L2M3H2 (or a variant thereof) may comprise or consist of the nucleotide sequence set forth in SEQ ID NO: 59, 63, 82, 84, 90 or 92, a nucleotide sequence which is degenerate with SEQ ID NO: 59, 63, 82, 84, 90 or 92 or a nucleotide sequence having at least 70%, 80%, 90% or 95% sequence identity to SEQ ID NO: 59, 63, 82, 84, 90 or 92. The nucleotide sequence encoding the heavy chain variable region of MDX-L1H4 or MDX-L2H2 (or variant thereof) may comprise or consist of the nucleotide sequence set forth in SEQ ID NO: 60 or 64, a nucleotide sequence which is degenerate with SEQ ID NO: 60 or 64 or a nucleotide sequence having at least 70%, 80%, 90% or 95% sequence identity to SEQ ID NO: 60 or 64.

Alternatively, the nucleic acid molecule of the invention may comprise a nucleotide sequence encoding the light chain of MDX-L1H4 or MDX-L2H2, or their variants MDX-L1M2H4, MDX-L1M3H4, MDX-L2M2H2 or MDX-L2M3H2, or a variant thereof, and a nucleotide sequence encoding the heavy chain of MDX-L1H4 or MDX-L2H2, or a variant thereof. The nucleotide sequence encoding the light chain of MDX-L1H4 or MDX-L2H2, or their variant MDX-L1M2H4, MDX-L1M3H4, MDX-L2M2H2 or MDX-L2M3H2 (or variant thereof) may comprise or consist of the nucleotide sequence set forth in SEQ ID NO: 57, 61, 81, 83, 89 or 91, a nucleotide sequence which is degenerate with SEQ ID NO: 57, 61, 81, 83, 89 or 91 or a nucleotide sequence having at least 70%, 80%, 90% or 95% sequence identity to SEQ ID NO: 57, 61, 81, 83, 89 or 91. The nucleotide sequence encoding the heavy chain of MDX-L1H4 or MDX-L2H2 (or variant thereof) may comprise or consist of the nucleotide sequence set forth in SEQ ID NO: 58 or 62, a nucleotide sequence which is degenerate with SEQ ID NO: 58 or 62 or a nucleotide sequence having at least 70%, 80%, 90% or 95% sequence identity to SEQ ID NO: 58 or 62.

In a further alternative, the nucleic acid molecule of the invention may comprise a nucleotide sequence encoding a specific binding molecule which binds human Anx-A1 and has the CDR sequences of MDX-L1H4, MDX-L2H2 or their variants MDX-L1M2H4, MDX-L1M3H4, MDX-L2M2H2 or MDX-L2M3H2, or a variant thereof (as described hereinbefore). Preferably, the nucleic acid molecule comprises the nucleotide sequences set forth in SEQ ID NO: 20, 65, 66 or 85-88 for (i.e. which encode) VLCDR1, SEQ ID NO: 21 or 67 for VLCDR2, SEQ ID NO: 22, 68 or 69 for VLCDR3, SEQ ID NO: 23, 70 or 71 for VHCDR1, SEQ ID NO: 24 or 72 for VHCDR2 and SEQ ID NO: 25, 73 or 74 for VHCDR3, or a nucleotide sequence which is degenerate to SEQ ID NOs: 20, 65, 66, 85-88, 21, 67, 22, 68, 69, 23, 70, 71, 24, 72, 25, 73 or 74, respectively, or a nucleotide sequence having at least 85%, 90% or 95% sequence identity to SEQ ID NO: 20, 65, 66, 85-88, 21, 67, 22, 68, 69, 23, 70, 71, 24, 72, 25, 73 or 74, respectively. Preferably in the above embodiment of the invention the nucleotide sequences are those of Mdx001, MDX-L1H4, MDX-L1M2H4, MDX-L1M3H4, MDX-L2H2, MDX-L2M2H2 or MDX-L2M3H2 (and their degenerate and sequence identity related sequence), e.g. SEQ ID NOs: 65, 67, 68, 70, 72 and 73 for MDX-L1M2H4.

The invention further provides a construct comprising the nucleic acid molecule of the invention. The construct is conveniently a recombinant construct comprising the nucleic acid molecule of the invention. In the construct, the nucleic acid molecule of the invention may be flanked by restriction sites (i.e. nucleotide sequences recognised by one or more restriction enzymes) to enable easy cloning of the nucleic acid molecule of the invention. In the construct of the invention the nucleotide sequence encoding the specific binding molecule of the invention may conveniently be operably linked within said construct to an expression control sequence, which may be heterologous to the nucleic acid molecule, i.e. non-native. Such an expression control sequence is typically a promoter, though the nucleotide sequence encoding the specific binding molecule may alternatively or additionally be operably linked to other expression control sequences such as a terminator sequence, an operator sequence, an enhancer sequence or suchlike. Accordingly, the construct may comprise a native or non-native promoter.

The term "operably linked" refers to the association of two or more nucleic acid molecules on a single nucleic acid fragment so that the function of one is affected by the other. For example, a promoter is operably linked to a coding sequence when it is capable of affecting the expression of that coding sequence (i.e. the coding sequence is under the transcriptional control of the promoter). Coding sequences may be operably linked to regulatory sequences in sense or antisense orientation.

The term "expression control sequence" refers to nucleotide sequences located upstream (5' non-coding sequences), within, or downstream (3' non-coding sequences) of a coding sequence, and which influence transcription, RNA processing or stability, or translation of the associated coding sequence. Expression control sequences may include promoters, operators, enhancers, translation leader sequences, a TATA box, a B recognition element and suchlike. As used herein, the term "promoter" refers to a nucleotide sequence capable of controlling the expression of a coding sequence or RNA. Suitable examples are provided hereinafter. In general, a coding sequence is located 3' to a promoter sequence. Promoters may be derived in their entirety from a native gene, or be composed of different elements derived from different promoters found in nature, or even comprise synthetic nucleotide segments. It is further recognised that since in most cases the exact boundaries of regulatory sequences have not been completely defined, nucleic acid fragments of different lengths may have identical regulatory activity.

Methods for preparing a construct of the invention are well known in the art, e.g. conventional polymerase chain reaction (PCR) cloning techniques can be used to construct the nucleic acid molecule of the invention which may be inserted into suitable constructs (e.g. containing an expression control sequence) using known methods.

The invention further provides a vector comprising a nucleic acid molecule or construct of the invention. The term "vector" as used herein refers to a vehicle into which the nucleic acid molecule or construct of the invention may be introduced (e.g. be covalently inserted) from which the specific binding molecule or mRNA encoding it may be expressed and/or the nucleic acid molecule/construct of the invention may be cloned. The vector may accordingly be a cloning vector or an expression vector.

The nucleic acid molecule or construct of the invention may be inserted into a vector using any suitable methods known in the art, for example, without limitation, the vector and nucleic acid molecule may be digested using appropriate restriction enzymes and then may be ligated with the nucleic acid molecule having matching sticky ends, or as appropriate the digested nucleic acid molecule may be ligated into the digested vector using blunt-ended cloning.

The vector may be a bacterial or prokaryotic vector, or it may be a eukaryotic vector, particularly a mammalian vector. The nucleic acid molecule or construct of the invention may be produced in or introduced into a general purpose cloning vector, particularly a bacterial cloning vector, e.g. an *Escherichia coli* cloning vector. Examples of such vectors include pUC19, pBR322, pBluescript vectors (Stratagene Inc.) and pCR TOPO® from Invitrogen Inc., e.g. pCR2.1-TOPO.

The nucleic acid molecule or construct of the invention may be sub-cloned into an expression vector for expression of the specific binding molecule of the invention, particularly a mammalian expression vector. Expression vectors can contain a variety of expression control sequences. In addition to control sequences that govern transcription and translation, vectors may contain additional nucleic acid sequences that serve other functions, including for example vector replication, selectable markers etc.

The expression vector should have the necessary 5' upstream and 3' downstream regulatory elements such as promoter sequences, e.g. the cytomegalovirus (CMV), PGK or EF1a promoter, particularly the human CMV (HCMV) promoter, ribosome recognition and binding TATA box, a Kozak sequence at the translation start site, and the 3' UTR AATAAA transcription termination sequence for efficient gene transcription and translation in its respective host cell. Other promoters include the constitutive simian virus 40 (SV40) early promoter, the mouse mammary tumour virus (MMTV) promoter, the HIV LTR promoter, the MoMuLV promoter, the avian leukaemia virus promoter, the EBV immediate early promoter, and the Rous sarcoma virus promoter. Human gene promoters may also be used, including, but not limited to the actin promoter, the myosin promoter, the haemoglobin promoter, and the creatine kinase promoter. In certain embodiments inducible promoters may be used. These provide a molecular switch capable of turning expression of the nucleic acid molecule on or off. Examples of inducible promoters include, but are not limited to, a metallothionine promoter, a glucocorticoid promoter, a progesterone promoter, or a tetracycline promoter.

Further, the expression vector may contain 5' and 3' untranslated regulatory sequences that may function as enhancer sequences, and/or terminator sequences that can facilitate or enhance efficient transcription of the nucleic acid molecule.

Examples of vectors are plasmids, autonomously replicating sequences, and transposable elements. Additional exemplary vectors include, without limitation, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g. herpes simplex virus), poxvirus, baculovirus, papillomavirus, and papovavirus (e.g. SV40).

Particularly preferred expression vectors are those disclosed in Kettleborough et al. (Protein Eng, Vol. 4(7): 773-783, 1991), which were specifically designed to express chimeric or reshaped human light and heavy chains in mammalian cells. These vectors contain the human cytomegalovirus (HCMV) enhancer and promoter for transcription, an appropriate human light or heavy chain constant region, a gene such as neomycin resistance (neo) for selection of transformed cells, and the SV40 origin of replication for DNA replication in host cells.

The method further provides a host cell comprising a nucleic acid molecule, construct or vector of the invention. The host cell may be a prokaryotic (e.g. bacterial) or eukaryotic (e.g. mammalian) cell. A prokaryotic cell may in particular be used as a cloning host for the nucleic acid molecule, construct or vector of the invention. Suitable prokaryotic cells for use as cloning hosts include without limitation, eubacteria, such as Gram-negative or Gram-positive organisms, for example, Enterobacteriaceae such as *Escherichia*, in particular *E. coli*, and Bacilli such as *B. subtilis*. The cloning host may alternatively be a eukaryotic cell such as a fungal cell, e.g. *Pichia pastoris*, or a yeast cell, or even a higher eukaryotic cell such as a mammalian cell.

The host cell of the invention may alternatively be a production host, i.e. a cell used to express and produce the specific binding molecule of the invention. The production host cell may be a prokaryotic cell, as defined above, but is preferably a eukaryotic cell. The production host may be a fungal cell, such as *Pichia pastoris* or a yeast cell, but is preferably a mammalian cell, particularly a rodent cell, a human cell or a cell of an alternative primate.

Particular examples of cells which may constitute a production host according to the invention include Cos cells, such as COS-7 cells, HEK293 cells, CHO cells, though any suitable cell type or line may be used.

The nucleic acid molecule, construct or vector of the invention may be integrated into the host cell chromosome or may be maintained extra-chromosomally. The nucleic acid molecule, construct or vector may be introduced into a host cell by any method known in the art. Such methods include, in particular, for prokaryotic cells transformation, transduction and conjugation. Transformation refers to the genetic alteration of a competent bacterium by direct uptake of DNA. Transduction refers to infection of a bacterium using a bacteriophage in order to introduce DNA of interest. Conjugation refers to the direct transfer of genetic material between bacterial cells in direct contact.

For eukaryotic cells, nucleic acid molecules, constructs and vectors may be introduced by transfection or transduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into viral particles or virions prior to contact with a cell. The skilled person is well aware of appropriate methods for introducing such genetic material into a host cell.

The invention also provides a method of preparing a specific binding molecule as defined herein comprising:

i) introducing into a host cell a nucleic acid molecule, construct or vector of the invention;

ii) expressing the nucleic acid molecule such that the specific binding molecule is produced; and iii) collecting the specific binding molecule, preferably by purification.

The host cell used in the method is as described above with reference to a host cell provided by the invention. Methods of introducing a nucleic acid molecule, construct or vector of the invention into a host cell are as described above. Advantageously, the nucleic acid molecule, construct or vector of the invention comprises a selectable marker such that host cells into which it has been introduced may be selected. Examples of selectable markers include antibiotic resistance genes, such as an ampicillin resistance gene (e.g. β-lactamase), a kanamycin resistance gene or a chloramphenicol resistance gene (e.g. chloramphenicol acetyl transferase). Selectable markers particularly suitable for use in mammalian host cells include hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

Cells into which a nucleic acid molecule, construct or vector have been introduced may then be easily selected as appropriate, e.g. by exposure to the compound to which the selectable marker confers resistance. In a particular embodiment of the invention CHO cells lacking the DHFR genes are transfected or transduced with a vector of the invention carrying a DHFR gene, restoring DHFR function in the cells. Transfected cells are then selected by culture in medium lacking thymidine, which DHFR is required to synthesise.

By "expression" of the nucleic acid molecule of the invention is meant that the gene, i.e. the nucleotide sequence, within the nucleic acid molecule, which encodes the specific binding molecule of the invention, is transcribed and translated so as to produce the specific binding molecule of the invention. Expression of the nucleic acid molecule, to produce the specific binding molecule of the invention, may be constitutive or inducible, depending on the promoter used to drive expression of the gene. It is straightforward for the skilled person to express a gene in a host cell, though it may be necessary for expression conditions to be optimised. This is well within the ability of the skilled person.

The specific binding molecule produced by the production host is finally collected. "Collection" of the specific binding molecule produced by this method simply means that it is separated from the production host cells. Collection does not necessarily entail isolation of the specific binding molecule, though preferably the specific binding molecule is isolated by purification. The specific binding molecule may be produced, such that it is secreted from the host cells, e.g. the specific binding molecule may be produced with a signal sequence. If the specific binding molecule is secreted by the host cells it can, at its most simple, be collected simply by isolating the culture supernatant by e.g. centrifugation of the culture. The specific binding molecule would thus be collected as it would be separated from the production host cells. Antibody heavy and light chains are natively encoded with N-terminal signal sequences, and are thus secreted from cells which produce them. Preferably, the specific binding molecule of the invention is produced such that it is secreted from the host cells, e.g. it may be produced with a signal sequence (and thus the nucleic acid molecule of the invention may encode a specific binding molecule with a signal sequence). Upon translocation of the polypeptide chains across the relevant membrane (the cell surface membrane in bacteria, the ER membrane in eukaryotes), the signal sequence is cleaved, yielding a mature polypeptide sequence. Specific binding molecules with and without signal sequences fall under the scope of this invention.

If the specific binding molecule of the invention is not produced such that it is secreted from the host cells, the specific binding molecule may be collected by harvesting and lysing the host cells producing the molecule. The individual skilled in the art can readily perform this task. Host cells may be harvested by centrifugation, and lysed by e.g. sonication, French Press, chemical lysis using a protein extraction reagent (e.g. BugBuster®, EMD Millipore (USA)), or a mammalian cell lysis kit as produced by e.g. AbCam (UK) or Sigma-Aldrich (USA)).

The specific binding molecule of the invention is preferably then purified. Methods for purification of specific binding molecules are described earlier. Purification is preferably achieved such that the specific binding molecule is at least 50% (e.g. 60, 70, 80, 90, 95%) pure, when assessed on a w/w basis relative to other components present in the solution or composition (excluding the solvent).

A specific binding molecule obtainable by the above method falls under the scope of this invention (i.e. which has the characteristics of a molecule obtained when such a method is used, even if that specific method is not used). The invention also extends to specific binding molecules which are obtained by using that method. Such a specific binding molecule has the characteristics of the specific binding molecule provided by the invention which is described above. A specific binding molecule obtainable by the above method is a polypeptide, preferably an antibody or a fragment of an antibody.

The invention further provides a pharmaceutical composition comprising a specific binding molecule or a preparation as disclosed herein, and one or more pharmaceutically acceptable diluents, carriers or excipients. The compositions of the invention may be formulated in any convenient manner according to techniques and procedures known in the pharmaceutical art. The specific binding molecule may be presented in the form of a pharmaceutically acceptable salt and in such cases the compositions are prepared accordingly. "Pharmaceutically acceptable" as used herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule, purpose of treatment, age of patient, mode of administration etc.

The pharmaceutical composition may be prepared for administration to a subject by any suitable means. Such administration may be e.g. oral, rectal, nasal, topical, vaginal or parenteral. Oral administration as used herein includes buccal and sublingual administration. Topical administration as used herein includes transdermal administration. Parenteral administration as defined herein includes subcutaneous, intramuscular, intravenous, intraperitoneal and intradermal administration.

Pharmaceutical compositions as disclosed herein include liquid solutions or syrups, solid compositions such as powders, granules, tablets or capsules, creams, ointments and any other style of composition commonly used in the art. Suitable pharmaceutically acceptable diluents, carriers and excipients for use in such compositions are well known in the art.

For instance, suitable excipients include lactose, maize starch or derivatives thereof, stearic acid or salts thereof, vegetable oils, waxes, fats and polyols. Suitable carriers or diluents include carboxymethylcellulose (CMC), methylcellulose, hydroxypropylmethylcellulose (HPMC), dextrose, trehalose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents and emulsifiers such as polysorbates. Stabilising agents, wetting agents, emulsifiers, sweeteners etc. may also be used.

Liquid pharmaceutical compositions, whether they be solutions, suspensions or other like form, may include one or more of the following: sterile diluents such as water for injection, saline solution, preferably physiological, Ringer's solution, isotonic sodium chloride, fixed oils such as synthetic mono- or diglycerides which may serve as a solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as EDTA; buffers such as acetates, citrates or phosphates and agents for the adjustment of tonicity such as sodium chloride or dextrose. A parenteral preparation can be enclosed in ampoules, disposable syringes or multiple dose vials made of glass or plastic. An injectable pharmaceutical composition is preferably sterile.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials. Conveniently a specific binding molecule of the invention may be provided to a subject in a daily, weekly or monthly dose, or a dose in an intermediate frequency, e.g. a dose may be provided every 2, 3, 4, 5 or 6 days, every 2, 3, 4, 5 or 6 weeks, every 2, 3, 4, 5 or 6 months, annually or biannually. The dose may be provided in the amount of from 10 ng/kg to 100 mg/kg, e.g. 1 μg/kg to 10 mg/kg body weight, for example from 10 μg/kg to 1 mg/kg. The skilled clinician will be able to calculate an appropriate dose for a patient based on all relevant factors, e.g. age, height, weight, the condition to be treated and its severity.

The pharmaceutical composition of the invention may further comprise at least one second therapeutically active agent, i.e. the composition may comprise both the specific binding molecule of the invention and another therapeutic agent. The second therapeutically active agent may be e.g. a drug molecule, a second specific binding molecule (i.e. a specific binding molecule which binds a ligand which is not human Anx-A1) or suchlike. The second therapeutically active agent may be a second agent for treatment of the condition during the treatment of which the specific binding molecule of the invention is administered to a subject, i.e. the specific binding molecule of the invention and the second therapeutic agent in the composition are both intended to treat the same illness or condition.

The second therapeutic agent may, in particular, be an anti-inflammatory or immunomodulatory drug or molecule. The immunomodulatory drug is in particular an immunosuppressant. Such drugs include steroids, such as glucocorticoids e.g. prednisone, prednisolone, methylprednisolone, cortisone, hydrocortisone, betamethasone, dexamethasone or triamcinolone; non-steroidal anti-inflammatory drugs (NSAIDs) e.g. aspirin, ibuprofen, celecoxib or naproxen; or anti-inflammatory peptides such as immune selective anti-inflammatory derivatives (ImSAIDs).

Also provided is a specific binding molecule, preparation or pharmaceutical composition as defined herein for use in therapy. By therapy is meant the treatment of a subject. By "therapy" as used herein is meant the treatment of any medical condition. Such treatment may be prophylactic (i.e. preventative), curative (or treatment intended to be curative), or palliative (i.e. treatment designed merely to limit, relieve or improve the symptoms of a condition). A subject, as defined herein, refers to any mammal, e.g. a farm animal such as a cow, horse, sheep, pig or goat, a pet animal such as a rabbit, cat or dog, or a primate such as a monkey, chimpanzee, gorilla or human. Most preferably the subject is a human.

The invention further provides a specific binding molecule, preparation or pharmaceutical composition as defined herein for use in the treatment of a T-cell-mediated disease, obsessive compulsive disorder (OCD) or an OCD-related disease. Antibodies specific for Anx-A1 have been found to be useful in treating OCD (WO2013/088111, incorporated herein by reference) and T-cell-mediated disease (WO2010/064012 and WO2011/154705, both incorporated herein by reference) and thus the specific binding molecules described herein which are similarly specific for Annexin-A1 may be used for these purposes.

Similarly, the invention provides a method of treatment for a T-cell-mediated disease, OCD or an OCD-related disease, comprising administering to a subject in need thereof a specific binding molecule, a preparation or a pharmaceutical composition as defined herein. Alternatively expressed, the invention also provides the use of a specific binding molecule or a preparation as defined herein in the manufacture of a medicament for use in the treatment of T-cell-mediated disease, OCD or an OCD-related disease in a subject.

Preferably, the specific binding molecule, preparation or pharmaceutical composition of the invention is administered to the subject in need thereof in a therapeutically effective amount. By "therapeutically effective amount" is meant an amount sufficient to show benefit to the condition of the subject. Whether an amount is sufficient to show benefit to the condition of the subject may be determined by the subject him/herself or a physician/veterinarian.

"T-cell-mediated disease" as used herein means any disease or condition in which T-cells play a role in pathogenesis or the development of the disease or condition. T-cell mediated diseases are typically caused by aberrant T-cell activation, and may thus be treated by blocking the activity of Anx-A1, as is achieved by using a specific binding molecule, preparation or pharmaceutical composition of the invention.

T-cell-mediated diseases include in particular, though are not limited to, autoimmune diseases, graft-versus-host disease, graft rejection, atherosclerosis, miscarriage and HIV/AIDS. Particular autoimmune diseases which may be treated according to the present invention include rheumatoid arthritis, multiple sclerosis, systemic lupus erythematosus, Addison's disease, Grave's disease, scleroderma, polymyositosis, diabetes, autoimmune uveoretinitis, ulcerative colitis, pemphigus vulgaris, inflammatory bowel disease, autoimmune thyroiditis, uveitis, Behçet's disease, Sjögren's syndrome and psoriasis.

T-cell-mediated diseases which may be treated according to the invention include miscarriage. An uncontrolled $T_h1$ T-cell response is known to be implicated in some miscarriages, whereas increasing the $T_h2$ T-cell response favours pregnancy. Thus miscarriage may be prevented by prophylactic treatment of pregnant women with the specific binding molecule of the invention, which by binding Anx-A1 dampens the $T_h1$ response and enhances the $T_h2$ response.

T-cell-mediated diseases which may be treated according to the invention also include atherosclerosis. Inflammation plays a key role in coronary artery disease and other manifestations of atherosclerosis. Immune cells dominate early atherosclerotic lesions, and effector molecules produced by the immune cells accelerate progression of the lesions. Thus the dampening of immune cell responses, as achieved by administration of the specific binding molecule of the invention to a subject, may relieve or delay atherosclerosis.

T-cell mediated diseases which the present invention is particularly useful in treating include rheumatoid arthritis (RA), multiple sclerosis (MS) and systemic lupus erythmatosus (SLE).

As noted above, specific binding molecules which bind Anx-A1 have also been found to be effective in the treatment of OCD and OCD-related diseases (WO 2013/088111). The specific binding molecule of the invention may thus be used to treat such conditions.

Diseases related to OCD which may be treated using the present invention include trichotillomania, dermatillomania, Tourette's syndrome, Asperger's syndrome, anorexia, bulimia, depression, panic disorder, panic attacks, bipolar disorder, hypochondriasis, post-traumatic stress disorder, social anxiety disorder, schizophrenia, attention deficit hyperactivity disorder or body dysmorphic disorder. In a preferred embodiment, the disease related to OCD treated using the present invention is an anxiety disorder. Anxiety disorders include generalised anxiety disorder, social anxiety disorder, panic disorder, panic attacks and post-traumatic stress disorder, each of which may be treated using the present invention.

All documents cited in the present application are hereby wholly incorporated herein by reference.

The invention may be further understood by reference to the non-limiting examples below.

Sequence Definitions

| SEQ ID NO: | Description | Type | Source |
|---|---|---|---|
| 1 | Mdx001 VLCDR1 | Protein | *Mus musculus* |
| 2 | Mdx001 VLCDR2 | Protein | *Mus musculus* |
| 3 | Mdx001 VLCDR3 | Protein | *Mus musculus* |
| 4 | Mdx001 VHCDR1 | Protein | *Mus musculus* |
| 5 | Mdx001 VHCDR2 | Protein | *Mus musculus* |
| 6 | Mdx001 VHCDR3 | Protein | *Mus musculus* |
| 7 | VJ-4B6 VLCDR1 | Protein | *Mus musculus* |
| 8 | VJ-4B6 VLCDR2 | Protein | *Mus musculus* |
| 9 | VJ-4B6 VLCDR3 | Protein | *Mus musculus* |
| 10 & 11 | Full-length human Anx-A1, as encoded by the ANXA1-002 and ANXA1-003 Transcripts | Protein | *Homo sapiens* |
| 12 | Human Anx-A1 fragment (encoded by the ANXA1-004 transcript) | Protein | *Homo sapiens* |
| 13 | Human Anx-A1 fragment (encoded by the ANXA1-006 transcript) | Protein | *Homo sapiens* |
| 14 | VJ-4B6 VHCDR3 | Protein | *Mus musculus* |
| 15 | Mdx001 light chain | Protein | *Mus musculus* |
| 16 | Mdx001 heavy chain | Protein | *Mus musculus* |
| 17 | Mdx001 CDRs Combined | Protein | Artificial Sequence |
| 18 | Mdx001 light chain variable region | Protein | *Mus musculus* |
| 19 | Mdx001 heavy chain variable region | Protein | *Mus musculus* |
| 20 | Mdx001 VLCDR1 (codon-optimised) | DNA | Artificial Sequence |
| 21 | Mdx001 VLCDR2 (codon-optimised) | DNA | Artificial Sequence |
| 22 | Mdx001 VLCDR3 (codon-optimised) | DNA | Artificial Sequence |
| 23 | Mdx001 VHCDR1 (codon-optimised) | DNA | Artificial Sequence |
| 24 | Mdx001 VHCDR2 (codon-optimised) | DNA | Artificial Sequence |
| 25 | Mdx001 VHCDR3 (codon-optimised) | DNA | Artificial Sequence |
| 26 | Mdx001 light chain variable region | DNA | *Mus musculus* |
| 27 | Mdx001 heavy chain variable region | DNA | *Mus musculus* |
| 28 | Mdx001 light chain variable region (codon-optimised) | DNA | Artificial Sequence |
| 29 | Mdx001 heavy chain variable region (codon-optimised) | DNA | Artificial Sequence |
| 30 | Mdx001 light chain (codon-optimised) | DNA | Artificial Sequence |
| 31 | Mdx001 heavy chain (codon-optimised) | DNA | Artificial Sequence |
| 32 | MDX-L1H4 light chain variable region | Protein | Artificial Sequence |
| 33 | MDX-L1H4 heavy chain variable region | Protein | Artificial Sequence |
| 34 | MDX-L2H2 light chain variable region | Protein | Artificial Sequence |
| 35 | MDX-L2H2 heavy chain variable region | Protein | Artificial Sequence |
| 36 | MDX-L1M2H4/MDX-L2M2H2 VLCDR1 | Protein | Artificial Sequence |
| 37 | MDX-L1M3H4/MDX-L2M3H2 VLCDR1 | Protein | Artificial Sequence |
| 38 | MDX-L1M2H4/MDX-L2M2H2 CDRs combined | Protein | Artificial Sequence |
| 39 | MDX-L1M3H4/MDX-L2M3H2 CDRs combined | Protein | Artificial Sequence |
| 40 | MDX-L1H4 light chain | Protein | Artificial Sequence |
| 41 | MDX-L1H4 heavy chain | Protein | Artificial Sequence |
| 42 | MDX-L2H2 light chain | Protein | Artificial Sequence |
| 43 | MDX-L2H2 heavy chain | Protein | Artificial Sequence |
| 44 | MDX-L1M2H4 light chain | Protein | Artificial Sequence |
| 45 | MDX-L2M2H2 light chain | Protein | Artificial Sequence |
| 46 | MDX-L1M3H4 light chain | Protein | Artificial Sequence |
| 47 | MDX-L2M3H2 light chain | Protein | Artificial Sequence |
| 48 | MDX-L1M2H4 light chain variable region | Protein | Artificial Sequence |
| 49 | MDX-L1M3H4 light chain variable region | Protein | Artificial Sequence |
| 50 | MDX-L2M2H2 light chain variable region | Protein | Artificial Sequence |
| 51 | MDX-L2M3H2 light chain variable region | Protein | Artificial Sequence |
| 52 | MDX-L1H4/MDX-L2H2 light chain signal sequence | Protein | Artificial Sequence |
| 53 | MDX-L1H4/MDX-L2H2 heavy chain signal sequence | Protein | Artificial Sequence |
| 54 | MDX-L1M2H4 mature light chain | Protein | Artificial Sequence |
| 55 | MDX-L1H4 mature heavy chain | Protein | Artificial Sequence |
| 56 | LC1(mod1)HC4/LC2(mod1)HC2 VLCDR1 | Protein | Artificial Sequence |
| 57 | MDX-L1M2H4 light chain | DNA | Artificial Sequence |
| 58 | MDX-L1H4 Heavy Chain | DNA | Artificial Sequence |
| 59 | MDX-L1M2H4 light chain variable region | DNA | Artificial Sequence |
| 60 | MDX-L1H4 Heavy Chain variable region | DNA | Artificial Sequence |
| 61 | MDX-L2M2H2 light chain | DNA | Artificial Sequence |
| 62 | MDX-L2H2 Heavy Chain | DNA | Artificial Sequence |

-continued

| SEQ ID NO: | Description | Type | Source |
|---|---|---|---|
| 63 | MDX-L2M2H2 light chain variable region | DNA | Artificial Sequence |
| 64 | MDX-L2H2 Heavy Chain variable region | DNA | Artificial Sequence |
| 65 | MDX-L1M2H4 VLCDR1 | DNA | Artificial Sequence |
| 66 | MDX-L2M2H2 VLCDR1 | DNA | Artificial Sequence |
| 67 | MDX-L1H4/MDX-L2H2 VLCDR2 | DNA | Artificial Sequence |
| 68 | MDX-L1H4 VLCDR3 | DNA | Artificial Sequence |
| 69 | MDX-L2H2 VLCDR3 | DNA | Artificial Sequence |
| 70 | MDX-L1H4 VHCDR1 | DNA | Artificial Sequence |
| 71 | MDX-L2H2 VHCDR1 | DNA | Artificial Sequence |
| 72 | MDX-L1H4/MDX-L2H2 VHCDR2 | DNA | Artificial Sequence |
| 73 | MDX-L1H4 VHCDR3 | DNA | Artificial Sequence |
| 74 | MDX-L2H2 VHCDR3 | DNA | Artificial Sequence |
| 75 | MDX-L1H4 mature light chain | Protein | Artificial Sequence |
| 76 | MDX-L1M3H4 mature light chain | Protein | Artificial Sequence |
| 77 | MDX-L2H2 mature light chain | Protein | Artificial Sequence |
| 78 | MDX-L2M2H2 mature light chain | Protein | Artificial Sequence |
| 79 | MDX-L2M3H2 mature light chain | Protein | Artificial Sequence |
| 80 | MDX-L2H2 mature heavy chain | Protein | Artificial Sequence |
| 81 | MDX-L1H4 light chain | DNA | Artificial Sequence |
| 82 | MDX-L1H4 light chain variable region | DNA | Artificial Sequence |
| 83 | MDX-L2H2 light chain | DNA | Artificial Sequence |
| 84 | MDX-L2H2 light chain variable region | DNA | Artificial Sequence |
| 85 | MDX-L1H4 VLCDR1 | DNA | Artificial Sequence |
| 86 | MDX-L2H2 VLCDR1 | DNA | Artificial Sequence |
| 87 | MDX-L1M3H4 VLCDR1 | DNA | Artificial Sequence |
| 88 | MDX-L2M3H2 VLCDR1 | DNA | Artificial Sequence |
| 89 | MDX-L1M3H4 light chain | DNA | Artificial Sequence |
| 90 | MDX-L1M3H4 light chain variable region | DNA | Artificial Sequence |
| 91 | MDX-L2M3H2 light chain | DNA | Artificial Sequence |
| 92 | MDX-L2M3H2 light chain variable region | DNA | Artificial Sequence |

FIGURE LEGENDS

FIG. 1 shows the results of an ELISA assay, demonstrating the binding of Mdx001 to Anx-A1. A492 values are proportionate to OPD degradation by the HRP conjugated to the secondary antibody, and thus represent Mdx001 binding.

Figure 2:
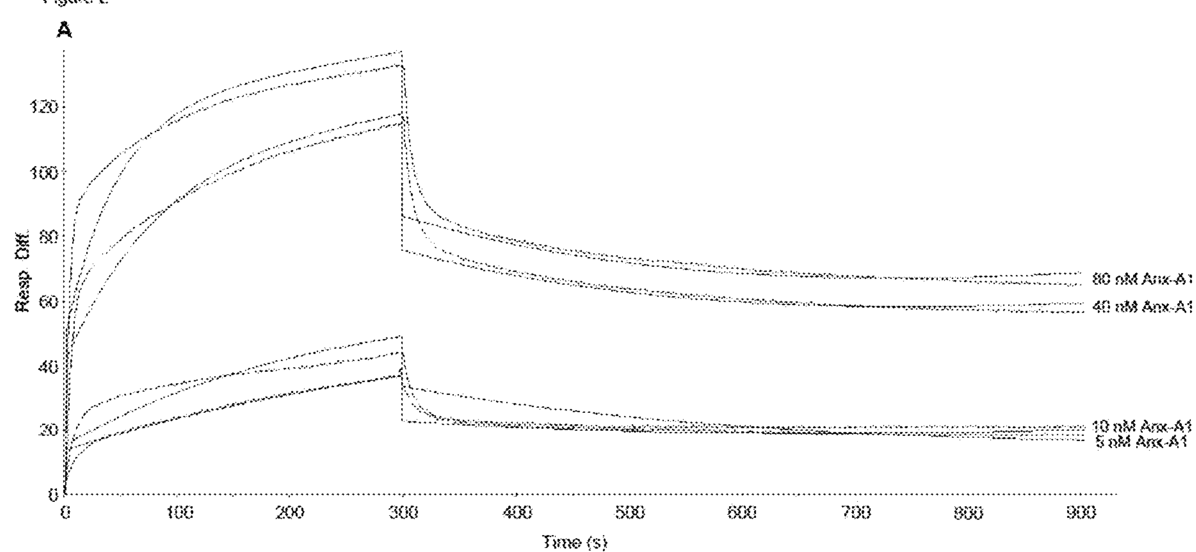
Figure 2:
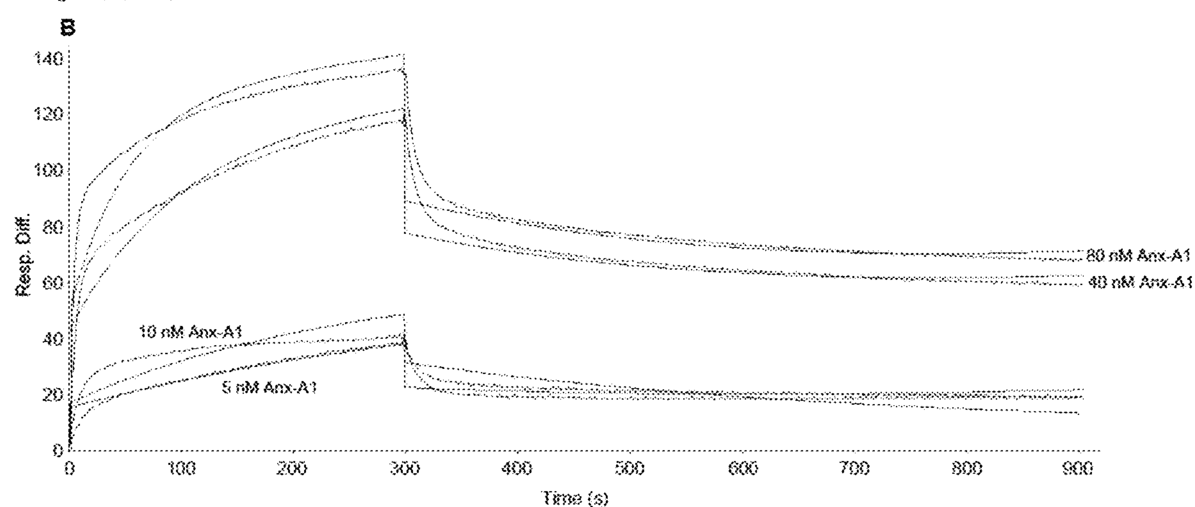
Figure 2:
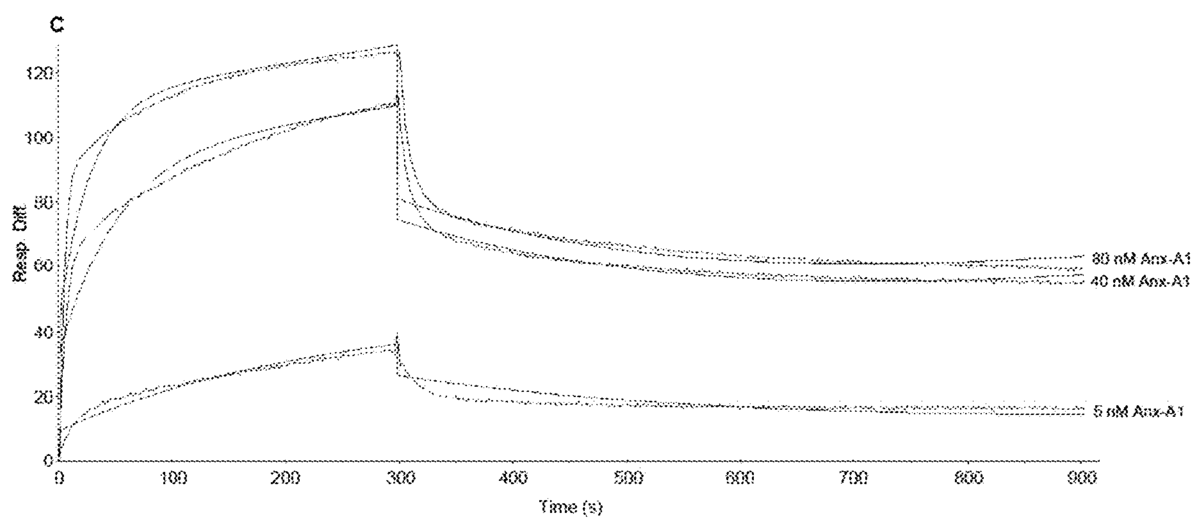

FIG. 2 shows the results of Biacore analysis of the binding of Mdx001 to Anx-A1. Parts A, B and C each present the results of a separate assay. Assay 1 (part A) shows a $K_D$ of 9.43 nM; Assay 2 (part B) shows a $K_D$ of 9.58 nM; Assay 3 (part C) shows a $K_D$ of 6.46 nM.

FIG. 3 shows the light and heavy chain variable regions of MDX-L1H4 and MDX-L2H2, and the variants that were generated from MDX-L1H4 and MDX-L2H2. Sequences are presented in single letter amino acid code. CDR sequences are in bold. Amino acid substitutions in the variant sequences (relative to MDX-L1H4 and MDX-L2H2) are highlighted.

Figure 4:
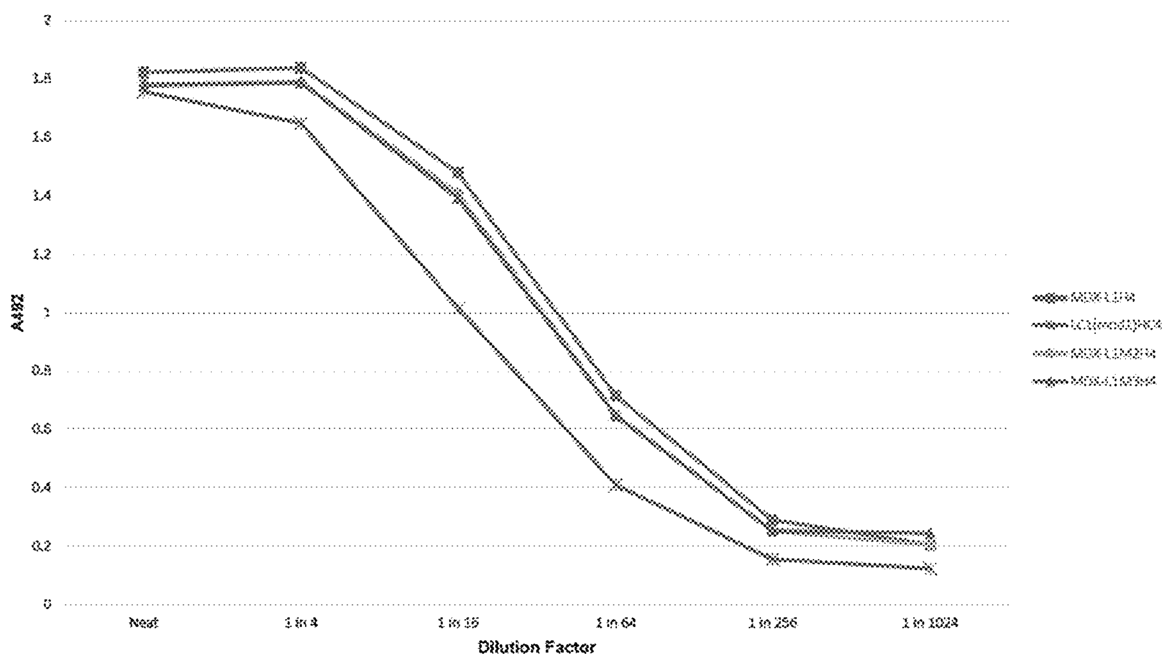
Figure 4:
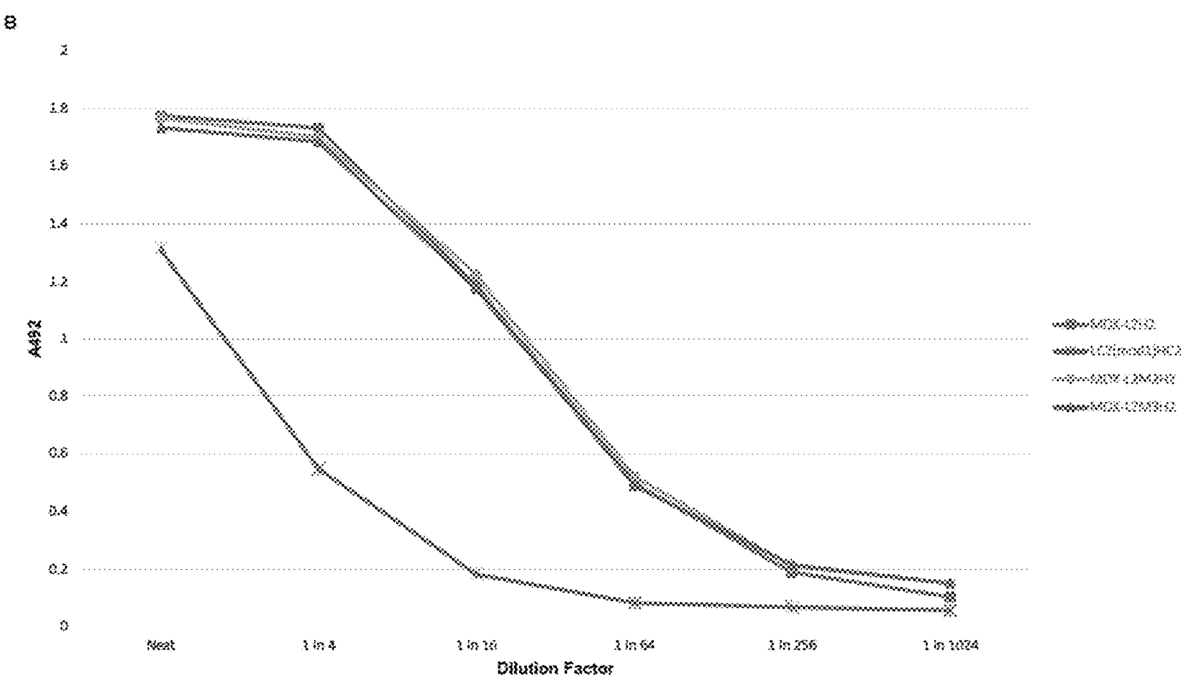

FIG. 4 shows the results of an ELISA assay, demonstrating the binding of antibodies MDX-L1H4 and its variants (A) and MDX-L2H2 and its variants (B) to Anx-A1. As in FIG. 1, the A492 values are proportionate to OPD degradation by the HRP conjugated to the secondary antibody, and thus represent antibody binding to Anx-A1.

Figure 5:
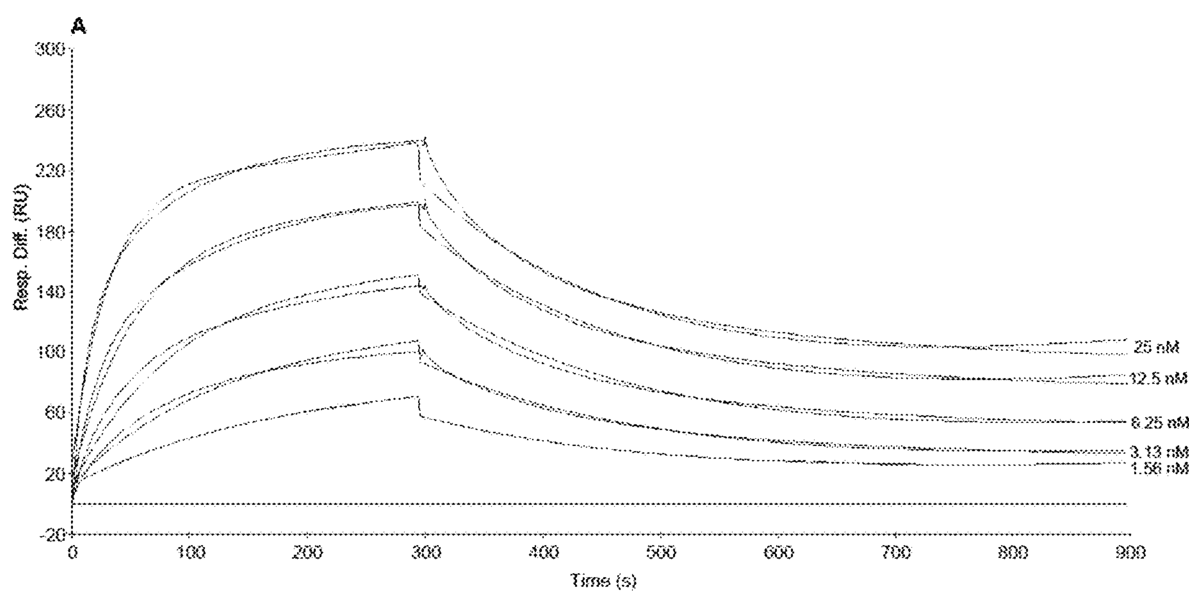
Figure 5:
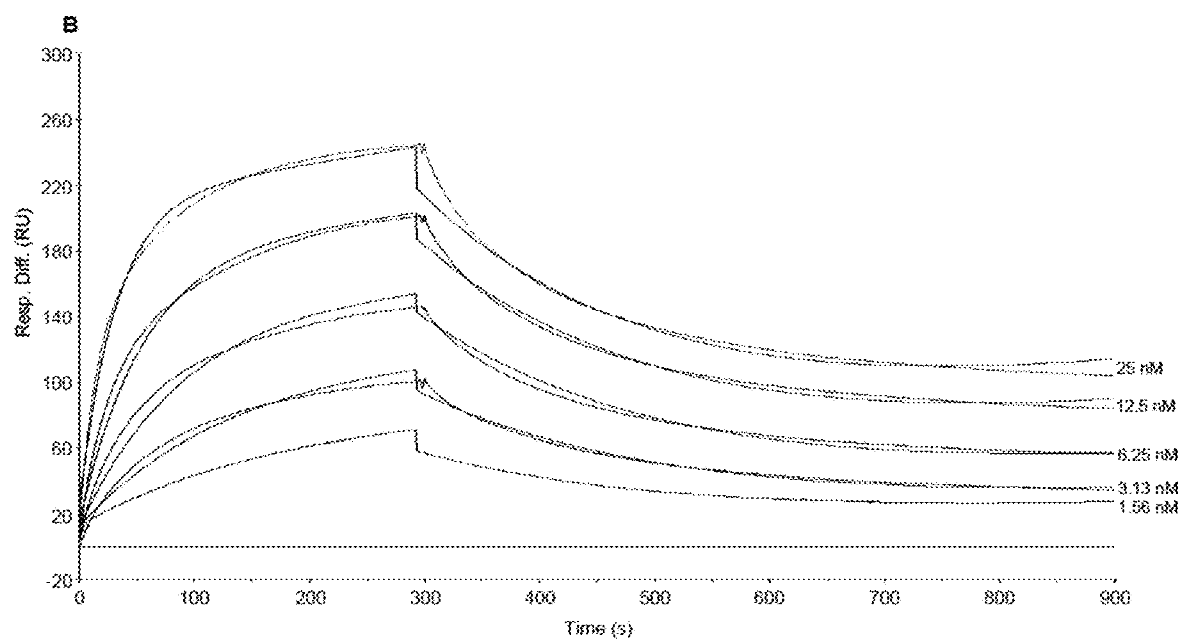
Figure 5:
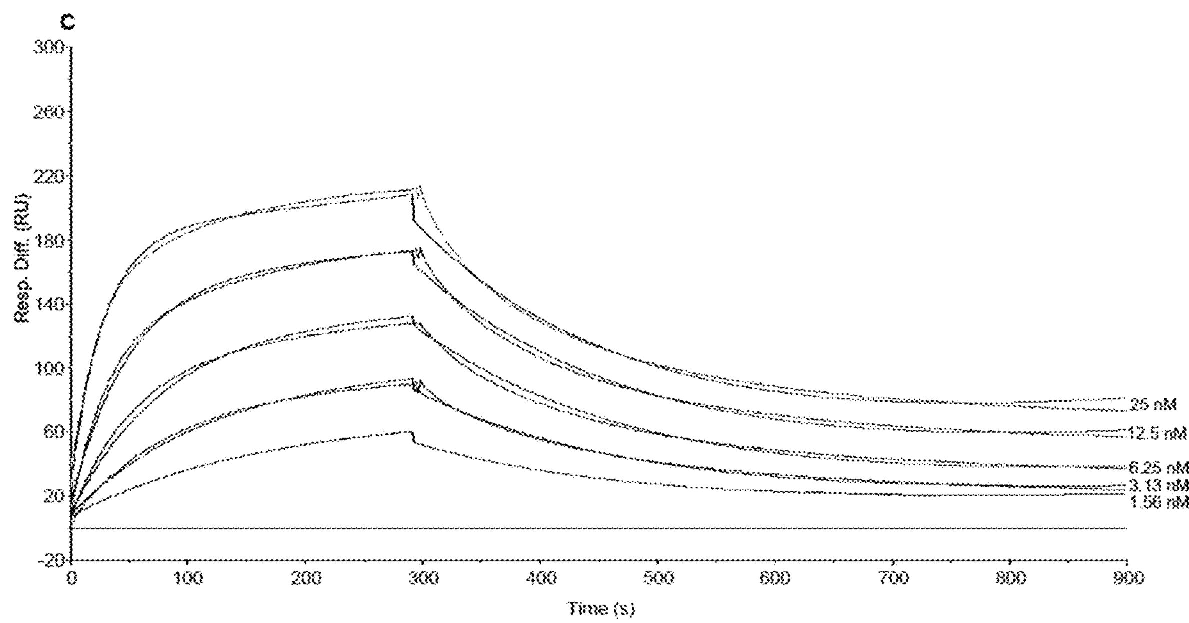
Figure 5:
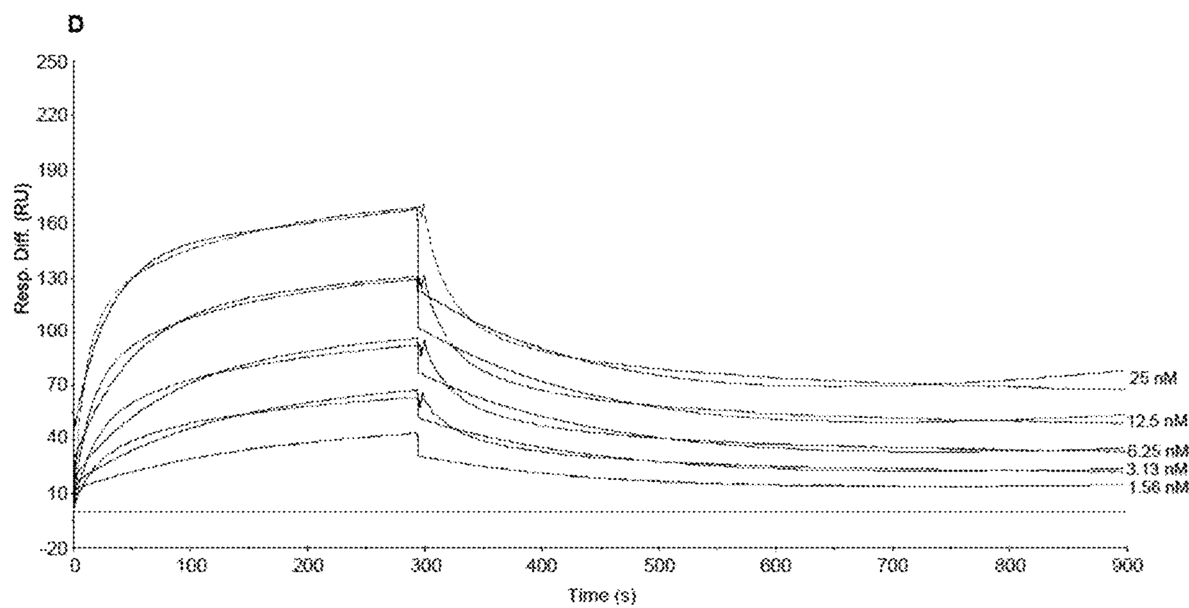
Figure 5:
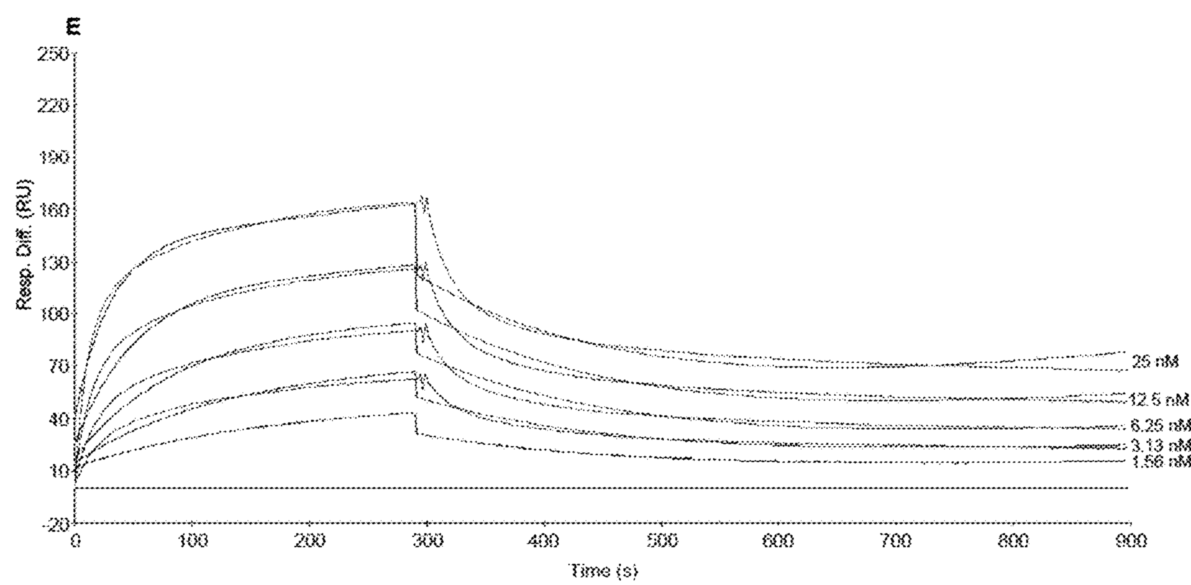
Figure 5:
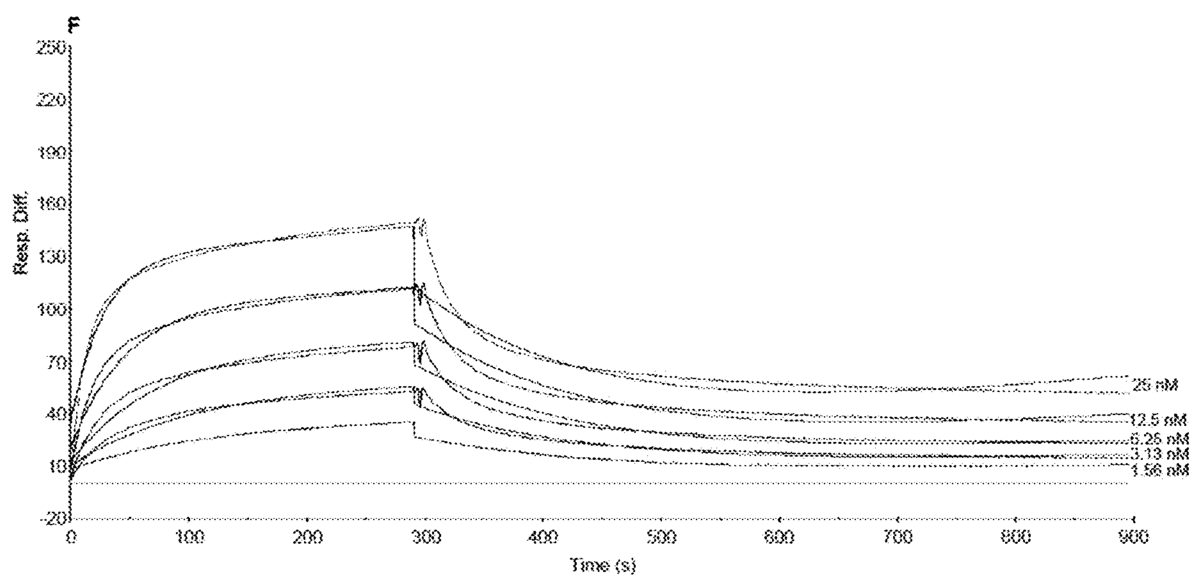

FIG. 5 shows the results of Biacore analysis of the binding of MDX-L1M2H4 and MDX-L2M2H2 to Anx-A1. Parts A-C each present the results of a separate assay for MDX-L1M2H4 binding to Anx-A1; Parts D-F each present the results of a separate assay for MDX-L2M2H2 binding to Anx-A1. For MDX-L1M2H4, Assay 1 (part A) shows a $K_D$ of 3.96 nM; Assay 2 (part B) shows a $K_D$ of 3.94 nM; Assay 3 (part C) shows a $K_d$ of 4.04 nM. For MDX-L2M2H2 Assay 1 (part D) shows a $K_D$ of 4.44 nM; Assay 2 (part E) shows a $K_D$ of 4.37 nM; Assay 3 (part F) shows a $K_d$ of 5.17 nM.

EXAMPLES

Example 1: Sequencing of Anx-A1-Binding Antibody Produced by Hybridoma ECACC 10060301 mRNA was extracted from hybridoma ECACC 10060301. The extracted mRNA was transcribed into cDNA using a reverse transcription protocol. The cDNA was sequenced by standard dye-terminator capillary sequencing by Aldevron (USA), using proprietary primers.

Cycle sequencing was performed using BigDye® Terminator v3.1 Cycle Sequencing kits under a standard protocol provided by Life Technologies®. All data was collected using a 3730xl DNA Analyser system and the Unified Data Collection software provided by Life Technologies® for operation of the 3730xl DNA Analyser and to collect data produced by the 3730xl DNA Analyser.

Sequence assembly was performed using CodonCode Aligner (CodonCode Corporation, USA). Mixed base calls are resolved by automatically assigning the most prevalent base call to the mixed base calls. Prevalence is determined by both frequency of a base call and the individual quality of the base calls.

The sequences of the light and heavy chain variable regions obtained by cDNA sequencing are presented in SEQ ID NOs: 26 and 27, respectively.

The sequences presented in SEQ ID NOs: 26 and 27 were run against a database of known germ lines and a germline for the antibody was identified. This showed that the sequence obtained for the light chain was truncated and missing 5 amino acids at its N-terminus. The complete sequences were reconstructed by Fusion Antibodies (UK) based upon the identified germline sequences and codon-optimised for expression in CHO cells. The codon-optimised variable domains have the sequences presented in SEQ ID NOs: 28 (light chain) and 29 (heavy chain).

Example 2: Production of the Anx-A1-Binding Mdx001 Antibody

The codon-optimised sequences were cloned into the vector pD2610-v13 (ATUM, USA) using standard recombinant techniques and transfected into ExpiCHO cells (Thermo Fisher Scientific, USA). 200 ml of culture was generated. Antibody (Mdx001) was recovered from the cell supernatant using a protein A affinity column and eluted into a phosphate buffer medium.

Example 3: Mdx001 Binds Anx-A1

Mdx001 binding to Anx-A1 was confirmed by ELISA, performed the The Antibody Company (UK) using standard ELISA techniques. ELISA plates were coated with 25 μg/ml Anx-A1 and coating buffer (45 mM $Na_2CO_3$, pH 9.6 supplemented with 1 mM $CaCl_2$) overnight at 4° C. ($Ca^{2+}$ was found to be required for Mdx001 binding to Anx-A1, and so all binding experiments were carried out in the presence of 1 mM $CaCl_2$.)

Plates were then blocked for 1 hr at room temperature with blocking buffer (1 mM $CaCl_2$, 10 mM HEPES, 2% w/v BSA). Primary antibody (Mdx001) was then applied to the plates. The antibody was applied in duplicate in four-fold dilutions made across the plate, starting at a concentration of 1 μg/ml and ending at a concentration of $2.38\times10^{-7}$ μg/ml. The antibody was diluted in wash buffer (10 mM HEPES, 150 mM NaCl, 0.05% (v/v) TWEEN-20 and 1 mM $CaCl_2$) supplemented with 0.1 BSA. The primary antibody was applied to the plate for 1 hr at room temperature, and the plate then washed with wash buffer.

The detection antibody was then applied. For detection a horseradish peroxidase (HRP)-conjugated goat anti-mouse antibody (Sigma-Aldrich, A2554) was used at a dilution of 1:1000. This was applied to the ELISA plate for 1 hour at room temperature. The ELISA plate was then washed again with wash buffer.

The colourimetric substrate OPD (o-phenylenediamine dihydrochloride, Sigma-Aldrich P4664) was then applied to the plate. OPD solution was made up according to the manufacturer's instructions to yield a 0.4 mg/ml OPD solution in phosphate-citrate buffer, pH 5. 40 μl of 30% $H_2O_2$ was added per 100 ml OPD solution immediately prior to use. 100 μl of the resultant OPD solution was then added to each well of the plate The plate was incubated for 20 mins in the dark at room temperature, after which 50 μl of 3M $H_2SO_4$ was added to stop the reaction. Immediately after addition of $H_2SO_4$ the absorbances of the plate were read at 492 nm (absorbance at 492 nm is abbreviated A492). Mdx001 was found to bind well to Anx-A1. The results are shown in Table 1 and FIG. 1. Mdx001 was found to bind across the plate except at the very highest dilutions. Even at the highest dilution of the anti-Anx-A1 antibody some binding is evident with a difference in absorbance seen between the blank values and the highest antibody dilution values. (Blank wells were coated with 25 μg/ml Anx-A1 in coating buffer and treated identically to experiment wells except no primary antibody was added.) The binding falls rapidly below 0.0625 μg/ml primary antibody (Mdx001). Binding appears to plateau at primary antibody concentrations below $3.9\times10^{-3}$ μg/ml.

| Mdx001 Concentration (μg/ml) | A492 |
|---|---|
| 1 | 1.772 |
| 0.25 | 1.66765 |
| 0.0625 | 1.59375 |
| 0.015625 | 0.8651 |
| 0.003906 | 0.31225 |
| 0.000977 | 0.20415 |
| 0.000244 | 0.17125 |
| $6.1\times10^{-5}$ | 0.14415 |
| $1.53\times10^{-5}$ | 0.16205 |
| $3.81\times10^{-6}$ | 0.1608 |
| $9.54\times10^{-7}$ | 0.1316 |
| $2.38\times10^{-7}$ | 0.1345 |

Example 4: Biacore Analysis of Mdx001 Binding to Annexin-A1

Biacore analysis was performed at the NMI, University of Tübingen, Germany. Standard Biacore procedures were used to analyse purified Mdx001 expressed in CHO cells as described above.

The running buffer used was follows: HEPES 10 mM, NaCl 150 mM, $CaCl_2$ 1 mM, Tween 20 0.05% v/v, pH 7.4. The buffer was filtered using a 0.22 μM filter and de-gassed by sonication for 15 mins.

The Mdx001 antibody was immobilised on a chip via a goat anti-mouse IgG. Ligand (Anx-A1) was passed over the immobilised antibody in running buffer. Anx-A1 was used at a concentration of 5, 10, 20, 40 or 80 nM. In each experiment, a total of 150 μl Anx-A1-containing running buffer was passed over the antibody, at a flow rate of 30 μl/min.

Regeneration was performed using a regeneration buffer, 10 mM glycine-HCl, pH 2. To regenerate the chip, 70 μl regeneration buffer was passed over the chip at a rate of 10 μl/min.

Experiments were performed in triplicate. Results of each of the 3 experiments are shown in FIG. 2. The three experiments gave $K_D$ values for the binding of Mdx001 to Anx-A1 of 9.43 nM, 9.58 nM and 6.46 nM, an average of 8.49 nM.

Example 5—Humanisation of Mdx001

Mdx001 was humanised using standard CDR grafting techniques coupled with antibody structure and database analysis of known human framework region sequences. All framework region sequences used were derived from mature IgG isolated from humans and so are expected to be non-immunogenic and retain the canonical structure of the CDR loops.

The humanisation process yielded two antibodies, MDX-L1H4 and MDX-L2H2, with sequences as set forth hereinbefore.

Example 6—Binding of Mdx002 to Anx-A1

The humanised antibodies were analysed to identify sites of possible post-translational modification, using standard bioinformatic tools. De-amidation is a major degradation pathway in antibodies so the humanised sequences were checked for the deamidation motifs Ser-Asn-Gly, Glu-Asn-Asn, Leu-Asn-Gly and Leu-Asn-Asn. A deamidation motif with the sequence Ser-Asn-Gly was identified in VLCDR1 of MDX-L1H4/MDX-L2H2. Modifications were made to MDX-L1H4 and MDX-L2H2 to remove this sequence motif. Humanised antibodies comprising a modified VLCDR1 sequence were generated in order to identify a functional modified VLCDR1 sequence.

Three variants were generated for each humanised antibody. FIG. 3 shows the light and heavy chain variable regions for the variants that were generated from MDX-L1H4 and MDX-L2H2.

The first of the modified antibodies, variant 1 (i.e. MDX-L1M2H4) comprised a VLCDR1 with the amino acid sequence set forth in SEQ ID NO: 36, i.e. a substitution of the glycine residue at position 11 for an alanine residue. The second of the modified antibodies, variant 2 (i.e. MDX-L1M3H4) comprised a VLCDR1 with the amino acid sequence set forth in SEQ ID NO: 37, i.e. a substitution of the serine residue at position 9 for a threonine residue. The third of the modified antibodies, variant 3 (annotated as LC1(mod 1)HC4) comprised a modified Mdx001 VLCDR1 sequence, in which the asparagine residue at position 10 was substituted for an aspartic acid residue. The LC1(mod 1)HC4 VLCDR1 sequence is set forth in SEQ ID NO: 56.

The variants from MDX-L2H2 are related to those from MDX-L1H4 insofar as they contain the same modifications in VLCDR1. They are referred to as variant 1 (MDX-L2M2H2), variant 2 (MDX-L2M3H2) and variant 3 (LC2 (mod 1)HC2).

Both antibodies contained humanised variable and constant domains as described in Example 5. The CDR sequences were otherwise unaltered relative to MDX-L1H4 and MDX-L2H2, and with the exception of the above-described VLCDR1 modifications were identical to their parent sequences.

Binding of the modified humanised antibodies to Anx-A1 was initially tested by ELISA, using the same method as described in Example 3. The results of this ELISA are presented in FIG. 4. As controls, MDX-L1H4 and MDX-L2H2 were used. As can be seen in FIG. 4A, MDX-L1M2H4 (LC1(mod 2)HC4) and MDX-L1M3H4 (LC1 (mod 3)HC4) (and MDX-L2M2H2 (LC2(mod 2)HC2) and MDX-L2M3H2 (LC2(mod 3)HC2), FIG. 4B) bound Anx-A1 comparably to MDX-L1H4 (or MDX-L2H2), but binding of LC1(mod 1)HC4 (and LC2(mod 1)HC2) to Anx-A1 was significantly weaker than for the control. This demonstrated that substitution of asparagine 10 in Mdx001 VLCDR1 for aspartic acid negatively impacted on binding of the antibody to Anx-A1. However, substitution of glycine 11 for alanine or threonine 9 for serine in the same CDR sequence did not negatively impact binding.

In light of the ELISA results, the LC1(mod 1)HC4 and LC2(mod 1)HC2 antibodies were discarded. The LC1(mod 2)HC4 and LC2(mod 2)HC2 antibodies, which demonstrated the best binding of the antibodies with modified VLCDR1 sequences, were taken forward for further analysis. Binding of LC1(mod 2)HC4 and LC2(mod 2)HC2 to Anx-A1 was quantified by Biacore, using the same method as described in Example 4. As in Example 4, the Biacore experiments were performed in triplicate. The results of each of the three experiments are presented in FIG. 5. As shown, for LC1(mod 2)HC4 the three experiments gave $K_D$ values of 3.96 nM, 3.94 nM and 4.04 nM, an average of 3.98 nM. This demonstrated that LC1(mod 2)HC4, which has a $K_D$ of 3.98 nM for Anx-A1 binding, binds Anx-A1 with significantly higher affinity than does Mdx001, which has a $K_D$ of 8.49 nM for Anx-A1 binding. LC1(mod 2)HC4 was given the name MDX-L1M2H4. For LC2(mod 2)HC2 the three experiments gave $K_D$ values of 4.44 nM, 4.37 nM and 5.17 nM, an average of 4.66 nM. This demonstrated that LC2 (mod 2)HC2, which has a $K_D$ of 4.66 nM for Anx-A1 binding, also binds Anx-A1 with significantly higher affinity than does Mdx001, which has a $K_D$ of 8.49 nM for Anx-A1 binding. LC2(mod 2)HC2 was given the name MDX-L2M2H2.

The invention claimed is:

1. An isolated specific binding molecule which binds human Anx-A1, said specific binding molecule comprising the complementarity-determining regions (CDRs) VLCDR1, VLCDR2, VLCDR3, VHCDR1, VHCDR2 and VHCDR3, wherein each of said CDRs has an amino acid sequence as follows:
 - VLCDR1 has the sequence set forth in SEQ ID NO: 36 or 37;
 - VLCDR2 has the sequence set forth in SEQ ID NO: 2;
 - VLCDR3 has the sequence set forth in SEQ ID NO: 3;
 - VHCDR1 has the sequence set forth in SEQ ID NO: 4;
 - VHCDR2 has the sequence set forth in SEQ ID NO: 5; and
 - VHCDR3 has the sequence set forth in SEQ ID NO: 6
 - and wherein the specific binding molecule is an antibody or antigen-binding fragment thereof.

2. The specific binding molecule of claim 1, wherein:
 - VLCDR1 has the sequence set forth in SEQ ID NO: 37;
 - VLCDR2 has the sequence set forth in SEQ ID NO: 2;
 - VLCDR3 has the sequence set forth in SEQ ID NO: 3;
 - VHCDR1 has the sequence set forth in SEQ ID NO: 4;
 - VHCDR2 has the sequence set forth in SEQ ID NO: 5; and
 - VHCDR3 has the sequence set forth in SEQ ID NO: 6.

3. The specific binding molecule of claim 1, wherein the antibody or fragment thereof is humanized.

4. The specific binding molecule of claim 1, wherein when said specific binding molecule is an antibody, the antibody is a monoclonal antibody, or when said specific binding molecule is a fragment of an antibody, said fragment is an Fab or $F(ab')_2$ antibody fragment, or an scFv molecule.

5. The specific binding molecule of claim 1, wherein said specific binding molecule binds human Anx-A1 with a $K_d$ of less than 20 nM.

6. The specific binding molecule of claim 4, wherein the antibody or fragment thereof comprises:
 - (i) a light chain variable region comprising the amino acid sequence set forth in any one of SEQ ID NOs: 48-51, or an amino acid sequence having at least 70% sequence identity thereto; and
 - (ii) a heavy chain variable region comprising the amino acid sequence set forth in SEQ ID NO: 33 or 35, or an amino acid sequence having at least 70% sequence identity thereto.

7. The specific binding molecule of claim 6, wherein the antibody or fragment thereof comprises:
 - (i) a light chain comprising the amino acid sequence set forth in any one of SEQ ID NOs: 44-47, 54, 76, 78 or 79 or an amino acid sequence having at least 70% sequence identity thereto; and
 - (ii) a heavy chain comprising the amino acid sequence set forth in SEQ ID NO: 41, 43, 55, or 80 or an amino acid sequence having at least 70% sequence identity thereto.

8. The specific binding molecule of claim 7, wherein the antibody comprises:
 - (i) a light chain comprising the amino acid sequence set forth in SEQ ID NO: 44; and a heavy chain comprising the amino acid sequence set forth in SEQ ID NO: 41; or
 - (ii) a light chain comprising the amino acid sequence set forth in SEQ ID NO: 54; and a heavy chain comprising the amino acid sequence set forth in SEQ ID NO: 55.

9. A preparation containing the specific binding molecule of claim 1, wherein at least 90% of the specific binding molecules in the preparation that bind to human Anx-A1 bind with a $K_d$ of less than 20 nM.

10. A pharmaceutical composition comprising a specific binding molecule as defined in claim 1 and one or more pharmaceutically acceptable diluents, carriers or excipients.

11. The pharmaceutical composition of claim 10, wherein the specific binding molecule is an antibody or fragment thereof comprising:
 - (i) a light chain variable region comprising the amino acid sequence set forth in any one of SEQ ID NOs: 48-51, or an amino acid sequence having at least 70% sequence identity thereto; and
 - (ii) a heavy chain variable region comprising the amino acid sequence set forth in SEQ ID NO: 33 or 35, or an amino acid sequence having at least 70% sequence identity thereto.

12. The pharmaceutical composition of claim 10, further comprising at least one second therapeutically active agent.

13. The specific binding molecule of claim 1, wherein:

VLCDR1 has the sequence set forth in SEQ ID NO: 36;

VLCDR2 has the sequence set forth in SEQ ID NO: 2;

VLCDR3 has the sequence set forth in SEQ ID NO: 3;

VHCDR1 has the sequence set forth in SEQ ID NO: 4;

VHCDR2 has the sequence set forth in SEQ ID NO: 5; and

VHCDR3 has the sequence set forth in SEQ ID NO: 6.

14. The specific binding molecule of claim 7, wherein the antibody comprises:

(i) a light chain comprising the amino acid sequence set forth in SEQ ID NO: 45; and a heavy chain comprising the amino acid sequence set forth in SEQ ID NO: 43; or (ii) a light chain comprising the amino acid sequence set forth in SEQ ID NO: 78; and a heavy chain comprising the amino acid sequence set forth in SEQ ID NO: 80.

15. An isolated specific binding molecule which binds human Anx-A1, wherein the specific binding molecule is an antibody or a fragment thereof and is humanized and comprises:

(i) a light chain variable region comprising the amino acid sequence set forth in SEQ ID NO: 32 or 34; and (ii) a heavy chain variable region comprising the amino acid sequence set forth in SEQ ID NO: 33 or 35.

16. The specific binding molecule of claim 15, wherein the specific binding molecule is an antibody comprising:

(i) a light chain comprising the amino acid sequence set forth in SEQ ID NO: 40, 42, 75 or 77, or an amino acid sequence with at least 80% sequence identity thereto; and (ii) a heavy chain comprising the amino acid sequence set forth in SEQ ID NO: 41, 43, 55 or 80, or an amino acid sequence with at least 80% sequence identity thereto.

17. A method of treatment for obsessive compulsive disorder (OCD) or an anxiety disorder, comprising administering to a subject in need thereof a specific binding molecule as defined in claim 1.

18. The method of claim 17, wherein the specific binding molecule is an antibody or fragment thereof comprising:

(i) a light chain variable region comprising the amino acid sequence set forth in any one of SEQ ID NOs: 48-51, or an amino acid sequence having at least 70% sequence identity thereto; and (ii) a heavy chain variable region comprising the amino acid sequence set forth in SEQ ID NO: 33 or 35, or an amino acid sequence having at least 70% sequence identity thereto.

* * * * *

SEQUENCE LISTING

```
<160> NUMBER OF SEQ ID NOS: 92

<210> SEQ ID NO 1
<211> LENGTH: 16
<212> TYPE: PRT
<213> ORGANISM: Mus musculus

<400> SEQUENCE: 1

Arg Ser Ser Gln Ser Leu Glu Asn Ser Asn Gly Lys Thr Tyr Leu Asn
1               5                   10                  15


<210> SEQ ID NO 2
<211> LENGTH: 7
<212> TYPE: PRT
<213> ORGANISM: Mus musculus

<400> SEQUENCE: 2

Gly Val Ser Asn Arg Phe Ser
1               5


<210> SEQ ID NO 3
<211> LENGTH: 9
<212> TYPE: PRT
<213> ORGANISM: Mus musculus

<400> SEQUENCE: 3

Leu Gln Val Thr His Val Pro Tyr Thr
1               5
```

<210> SEQ ID NO 4
<211> LENGTH: 10
<212> TYPE: PRT
<213> ORGANISM: Mus musculus

<400> SEQUENCE: 4

Gly Tyr Thr Phe Thr Asn Tyr Trp Ile Gly
1               5                   10

<210> SEQ ID NO 5
<211> LENGTH: 17
<212> TYPE: PRT
<213> ORGANISM: Mus musculus

<400> SEQUENCE: 5

Asp Ile Tyr Pro Gly Gly Asp Tyr Thr Asn Tyr Asn Glu Lys Phe Lys
1               5                   10                  15

Gly

<210> SEQ ID NO 6
<211> LENGTH: 11
<212> TYPE: PRT
<213> ORGANISM: Mus musculus

<400> SEQUENCE: 6

Ala Arg Trp Gly Leu Gly Tyr Tyr Phe Asp Tyr
1               5                   10

<210> SEQ ID NO 7
<211> LENGTH: 11
<212> TYPE: PRT
<213> ORGANISM: Mus musculus

<400> SEQUENCE: 7

Lys Ala Ser Glu Asn Val Val Thr Tyr Val Ser
1               5                   10

<210> SEQ ID NO 8
<211> LENGTH: 7
<212> TYPE: PRT
<213> ORGANISM: Mus musculus

<400> SEQUENCE: 8

Gly Ala Ser Asn Arg Tyr Thr
1               5

<210> SEQ ID NO 9
<211> LENGTH: 9
<212> TYPE: PRT
<213> ORGANISM: Mus musculus

<400> SEQUENCE: 9

Gly Gln Gly Tyr Ser Tyr Pro Tyr Thr
1               5

<210> SEQ ID NO 10
<211> LENGTH: 346
<212> TYPE: PRT
<213> ORGANISM: Homo sapiens

<400> SEQUENCE: 10

Met Ala Met Val Ser Glu Phe Leu Lys Gln Ala Trp Phe Ile Glu Asn
1               5                   10                  15

```
Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345
```

<210> SEQ ID NO 11
<211> LENGTH: 346
<212> TYPE: PRT
<213> ORGANISM: Homo sapiens

<400> SEQUENCE: 11

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
```

```
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345


<210> SEQ ID NO 12
<211> LENGTH: 204
<212> TYPE: PRT
<213> ORGANISM: Homo sapiens

<400> SEQUENCE: 12

Met Asn Leu Ile Leu Arg Tyr Thr Phe Ser Lys Met Ala Met Val Ser
1               5                   10                  15

Glu Phe Leu Lys Gln Ala Trp Phe Ile Glu Asn Glu Glu Gln Glu Tyr
            20                  25                  30

Val Gln Thr Val Lys Ser Ser Lys Gly Gly Pro Gly Ser Ala Val Ser
        35                  40                  45

Pro Tyr Pro Thr Phe Asn Pro Ser Ser Asp Val Ala Ala Leu His Lys
    50                  55                  60
```

```
Ala Ile Met Val Lys Gly Val Asp Glu Ala Thr Ile Ile Asp Ile Leu
65                  70                  75                  80

Thr Lys Arg Asn Asn Ala Gln Arg Gln Gln Ile Lys Ala Ala Tyr Leu
                85                  90                  95

Gln Glu Thr Gly Lys Pro Leu Asp Glu Thr Leu Lys Lys Ala Leu Thr
            100                 105                 110

Gly His Leu Glu Glu Val Val Leu Ala Leu Leu Lys Thr Pro Ala Gln
        115                 120                 125

Phe Asp Ala Asp Glu Leu Arg Ala Ala Met Lys Gly Leu Gly Thr Asp
    130                 135                 140

Glu Asp Thr Leu Ile Glu Ile Leu Ala Ser Arg Thr Asn Lys Glu Ile
145                 150                 155                 160

Arg Asp Ile Asn Arg Val Tyr Arg Glu Glu Leu Lys Arg Asp Leu Ala
                165                 170                 175

Lys Asp Ile Thr Ser Asp Thr Ser Gly Asp Phe Arg Asn Ala Leu Leu
            180                 185                 190

Ser Leu Ala Lys Gly Asp Arg Ser Glu Asp Phe Gly
        195                 200


<210> SEQ ID NO 13
<211> LENGTH: 115
<212> TYPE: PRT
<213> ORGANISM: Homo sapiens

<400> SEQUENCE: 13

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro
        115


<210> SEQ ID NO 14
<211> LENGTH: 9
<212> TYPE: PRT
<213> ORGANISM: Mus musculus

<400> SEQUENCE: 14

Trp Gly Leu Gly Tyr Tyr Phe Asp Tyr
1               5


<210> SEQ ID NO 15
<211> LENGTH: 239
<212> TYPE: PRT
<213> ORGANISM: Mus musculus

<400> SEQUENCE: 15

Met Val Ser Ser Ala Gln Phe Leu Gly Leu Leu Leu Leu Cys Phe Gln
```

```
1               5                   10                  15

Gly Thr Arg Cys Asp Ala Val Met Thr Gln Thr Pro Leu Ser Leu Pro
            20                  25                  30

Val Ser Leu Gly Asp Gln Val Ser Ile Ser Cys Arg Ser Ser Gln Ser
        35                  40                  45

Leu Glu Asn Ser Asn Gly Lys Thr Tyr Leu Asn Trp Tyr Leu Gln Lys
    50                  55                  60

Pro Gly Gln Ser Pro Gln Leu Leu Ile Tyr Gly Val Ser Asn Arg Phe
65                  70                  75                  80

Ser Gly Val Leu Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110

Cys Leu Gln Val Thr His Val Pro Tyr Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235


<210> SEQ ID NO 16
<211> LENGTH: 473
<212> TYPE: PRT
<213> ORGANISM: Mus musculus

<400> SEQUENCE: 16

Met Gly Trp Thr Leu Val Phe Leu Phe Leu Leu Ser Val Thr Ala Gly
1               5                   10                  15

Val His Ser Gln Val Gln Leu Gln Gln Ser Gly Pro Glu Leu Val Arg
            20                  25                  30

Pro Gly Thr Ser Val Lys Met Ser Cys Lys Ala Ser Gly Tyr Thr Phe
        35                  40                  45

Thr Asn Tyr Trp Ile Gly Trp Ala Lys Gln Arg Pro Gly His Gly Leu
    50                  55                  60

Glu Trp Ile Gly Asp Ile Tyr Pro Gly Gly Asp Tyr Thr Asn Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Phe Ser Ser Leu Thr Ser Glu Asp Ser Ala Ile
            100                 105                 110

Tyr Tyr Cys Ala Arg Trp Gly Leu Gly Tyr Tyr Phe Asp Tyr Trp Gly
        115                 120                 125

Gln Gly Ile Thr Leu Thr Val Ser Ser Ala Lys Thr Thr Pro Pro Ser
    130                 135                 140
```

```
Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
                165                 170                 175

Thr Trp Asn Ser Gly Ser Leu Ser Ser Ser Val His Thr Phe Pro Ala
            180                 185                 190

Leu Leu Gln Ser Gly Leu Tyr Thr Met Ser Ser Ser Val Thr Val Pro
        195                 200                 205

Ser Ser Thr Trp Pro Ser Gln Thr Val Thr Cys Ser Val Ala His Pro
    210                 215                 220

Ala Ser Ser Thr Thr Val Asp Lys Lys Leu Glu Pro Ser Gly Pro Ile
225                 230                 235                 240

Ser Thr Ile Asn Pro Cys Pro Pro Cys Lys Glu Cys His Lys Cys Pro
                245                 250                 255

Ala Pro Asn Leu Glu Gly Gly Pro Ser Val Phe Ile Phe Pro Pro Asn
            260                 265                 270

Ile Lys Asp Val Leu Met Ile Ser Leu Thr Pro Lys Val Thr Cys Val
        275                 280                 285

Val Val Asp Val Ser Glu Asp Asp Pro Asp Val Gln Ile Ser Trp Phe
    290                 295                 300

Val Asn Asn Val Glu Val His Thr Ala Gln Thr Gln Thr His Arg Glu
305                 310                 315                 320

Asp Tyr Asn Ser Thr Ile Arg Val Val Ser Thr Leu Pro Ile Gln His
                325                 330                 335

Gln Asp Trp Met Ser Gly Lys Glu Phe Lys Cys Lys Val Asn Asn Lys
            340                 345                 350

Asp Leu Pro Ser Pro Ile Glu Arg Thr Ile Ser Lys Ile Lys Gly Leu
        355                 360                 365

Val Arg Ala Pro Gln Val Tyr Ile Leu Pro Pro Pro Ala Glu Gln Leu
    370                 375                 380

Ser Arg Lys Asp Val Ser Leu Thr Cys Leu Val Val Gly Phe Asn Pro
385                 390                 395                 400

Gly Asp Ile Ser Val Glu Trp Thr Ser Asn Gly His Thr Glu Glu Asn
                405                 410                 415

Tyr Lys Asp Thr Ala Pro Val Leu Asp Ser Asp Gly Ser Tyr Phe Ile
            420                 425                 430

Tyr Ser Lys Leu Asn Met Lys Thr Ser Lys Trp Glu Lys Thr Asp Ser
        435                 440                 445

Phe Ser Cys Asn Val Arg His Glu Gly Leu Lys Asn Tyr Tyr Leu Lys
    450                 455                 460

Lys Thr Ile Ser Arg Ser Pro Gly Lys
465                 470
```

<210> SEQ ID NO 17
<211> LENGTH: 70
<212> TYPE: PRT
<213> ORGANISM: Artificial Sequence
<220> FEATURE:
<223> OTHER INFORMATION: Combined sequence of Mdx001 CDRs

<400> SEQUENCE: 17

```
Arg Ser Ser Gln Ser Leu Glu Asn Ser Asn Gly Lys Thr Tyr Leu Asn
1               5                   10                  15

Gly Val Ser Asn Arg Phe Ser Leu Gln Val Thr His Val Pro Tyr Thr
            20                  25                  30
```

```
Gly Tyr Thr Phe Thr Asn Tyr Trp Ile Gly Asp Ile Tyr Pro Gly Gly
        35                  40                  45

Asp Tyr Thr Asn Tyr Asn Glu Lys Phe Lys Gly Ala Arg Trp Gly Leu
    50                  55                  60

Gly Tyr Tyr Phe Asp Tyr
65                  70


<210> SEQ ID NO 18
<211> LENGTH: 112
<212> TYPE: PRT
<213> ORGANISM: Mus musculus

<400> SEQUENCE: 18

Asp Ala Val Met Thr Gln Thr Pro Leu Ser Leu Pro Val Ser Leu Gly
1               5                   10                  15

Asp Gln Val Ser Ile Ser Cys Arg Ser Ser Gln Ser Leu Glu Asn Ser
            20                  25                  30

Asn Gly Lys Thr Tyr Leu Asn Trp Tyr Leu Gln Lys Pro Gly Gln Ser
        35                  40                  45

Pro Gln Leu Leu Ile Tyr Gly Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Lys Leu Glu Ile Lys
            100                 105                 110


<210> SEQ ID NO 19
<211> LENGTH: 118
<212> TYPE: PRT
<213> ORGANISM: Mus musculus

<400> SEQUENCE: 19

Gln Val Gln Leu Gln Gln Ser Gly Pro Glu Leu Val Arg Pro Gly Thr
1               5                   10                  15

Ser Val Lys Met Ser Cys Lys Ala Ser Gly Tyr Thr Phe Thr Asn Tyr
            20                  25                  30

Trp Ile Gly Trp Ala Lys Gln Arg Pro Gly His Gly Leu Glu Trp Ile
        35                  40                  45

Gly Asp Ile Tyr Pro Gly Gly Asp Tyr Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Phe Ser Ser Leu Thr Ser Glu Asp Ser Ala Ile Tyr Tyr Cys
                85                  90                  95

Ala Arg Trp Gly Leu Gly Tyr Tyr Phe Asp Tyr Trp Gly Gln Gly Ile
            100                 105                 110

Thr Leu Thr Val Ser Ser
        115


<210> SEQ ID NO 20
<211> LENGTH: 48
<212> TYPE: DNA
<213> ORGANISM: Artificial Sequence
<220> FEATURE:
<223> OTHER INFORMATION: Mdx001 VLCDR1 Sequence Codon-Optimised for
      Expression in Hamster
```

<400> SEQUENCE: 20
cggtcaagcc agagcttgga gaactcgaat ggaaagacct acctcaat 48

<210> SEQ ID NO 21
<211> LENGTH: 21
<212> TYPE: DNA
<213> ORGANISM: Artificial Sequence
<220> FEATURE:
<223> OTHER INFORMATION: Mdx001 VLCDR2 Sequence Codon-Optimised for Expression in Hamster

<400> SEQUENCE: 21
ggggtgtcga acagattttc c 21

<210> SEQ ID NO 22
<211> LENGTH: 27
<212> TYPE: DNA
<213> ORGANISM: Artificial Sequence
<220> FEATURE:
<223> OTHER INFORMATION: Mdx001 VLCDR3 Sequence Codon-Optimised for Expression in Hamster

<400> SEQUENCE: 22
cttcaggtca cccatgtgcc gtacacc 27

<210> SEQ ID NO 23
<211> LENGTH: 30
<212> TYPE: DNA
<213> ORGANISM: Artificial Sequence
<220> FEATURE:
<223> OTHER INFORMATION: Mdx001 VHCDR1 Sequence Codon-Optimised for Expression in Hamster

<400> SEQUENCE: 23
ggctacacct tcaccaacta ctggatcggc 30

<210> SEQ ID NO 24
<211> LENGTH: 51
<212> TYPE: DNA
<213> ORGANISM: Artificial Sequence
<220> FEATURE:
<223> OTHER INFORMATION: Mdx001 VLCDR2 Sequence Codon-Optimised for Expression in Hamster

<400> SEQUENCE: 24
gacatctatc cgggtggaga ctacaccaac tacaacgaaa agttcaaggg a 51

<210> SEQ ID NO 25
<211> LENGTH: 33
<212> TYPE: DNA
<213> ORGANISM: Artificial Sequence
<220> FEATURE:
<223> OTHER INFORMATION: Mdx001 VHCDR3 Sequence Codon-Optimised for Expression in Hamster

<400> SEQUENCE: 25
gcccggtggg gacttggtta ctacttcgac tac 33

<210> SEQ ID NO 26
<211> LENGTH: 321
<212> TYPE: DNA
<213> ORGANISM: Mus musculus

<400> SEQUENCE: 26
cagactccac tctccctgcc tgtcagtctt ggagatcaag tctccatctc ttgcaggtct 60
agtcagagcc ttgaaaacag taatggaaaa acctatttga actggtacct ccagaaacca 120
ggccagtctc cacagctcct gatctacggg gtttccaacc gattttctgg ggtcctagac 180
aggttcagtg gtagtggatc agggacagat ttcacactga aaatcagcag agtggaggct 240
gaggatttgg gagtttattt ctgcctccaa gttacacatg tcccgtacac gttcggaggg 300
gggaccaagc tggaaataaa a 321

<210> SEQ ID NO 27
<211> LENGTH: 357
<212> TYPE: DNA
<213> ORGANISM: Mus musculus

<400> SEQUENCE: 27
ccaggtccag ctgcagcagt ctggacctga actggtcagg cctgggactt cagtgaagat 60
gtcctgcaag gcttctggat acaccttcac taactactgg ataggttggg caaagcagag 120
gcctggacat ggccttgagt ggattggaga tatttaccct ggaggtgatt atactaacta 180
caatgagaag ttcaagggca aggccacact gactgcagac aaatcctcca gcacagccta 240
catgcagttc agcagcctga catctgagga ctctgccatc tattattgtg caagatgggg 300
gttaggatac tactttgact actggggcca aggcatcact ctcacagtct cctcagc 357

<210> SEQ ID NO 28
<211> LENGTH: 336
<212> TYPE: DNA
<213> ORGANISM: Artificial Sequence
<220> FEATURE:
<223> OTHER INFORMATION: Mdx001 Light Chain Variable Region
Codon-Optimised for Expression in Hamster

<400> SEQUENCE: 28
gacgctgtga tgacccagac tcctctgtcc ctgcccgtgt ccctgggggga ccaagtctcc 60 atctcctgcc ggtcaagcca gagcttggag aactcgaatg gaaagaccta cctcaattgg 120
tacctccaga agccggggca gtccccccaa ctcctgatct acggggtgtc gaacagattt 180
tccggagtgc tggatcggtt ctcgggctcc ggaagcggca ccgacttcac tctgaaaatt 240
agccgcgtgg aagccgagga cttgggcgtg tatttctgcc ttcaggtcac ccatgtgccg 300
tacaccttcg gtggcggcac aaagctggaa atcaag 336

<210> SEQ ID NO 29
<211> LENGTH: 354
<212> TYPE: DNA
<213> ORGANISM: Artificial Sequence
<220> FEATURE:
<223> OTHER INFORMATION: Mdx001 Heavy Chain Variable Region
Codon-Optimised for Expression in Hamster

<400> SEQUENCE: 29
caagtgcagc tgcagcagtc cggccccgaa ctcgtgcggc caggcacctc cgtgaagatg 60
tcctgcaaag cgtccggcta caccttcacc aactactgga tcggctgggc aaagcagagg 120
cccggacatg gcctcgaatg gattggcgac atctatccgg gtggagacta caccaactac 180
aacgaaaagt tcaagggaaa ggccaccctg accgctgata agtccagctc caccgcatac 240
atgcagttct cgtcactgac tagcgaagat tccgcgatct actactgcgc ccggtgggga 300
cttggttact acttcgacta ctggggacag ggaattaccc tgaccgtgtc cagc 354

<210> SEQ ID NO 30
<211> LENGTH: 717

<212> TYPE: DNA
<213> ORGANISM: Artificial Sequence
<220> FEATURE:
<223> OTHER INFORMATION: Mdx001 Light Chain Codon-Optimised for Expression in Hamster

<400> SEQUENCE: 30
atggtgtcat ctgcacaatt tctgggactt cttctgctgt gtttccaagg aacccgctgt 60
gacgctgtga tgacccagac tcctctgtcc ctgcccgtgt ccctggggga ccaagtctcc 120
atctcctgcc ggtcaagcca gagcttggag aactcgaatg gaaagaccta cctcaattgg 180
tacctccaga agccggggca gtccccccaa ctcctgatct acggggtgtc gaacagattt 240
tccggagtgc tggatcggtt ctcgggctcc ggaagcggca ccgacttcac tctgaaaatt 300
agccgcgtgg aagccgagga cttgggcgtg tatttctgcc ttcaggtcac ccatgtgccg 360
tacaccttcg gtggcggcac aaagctggaa atcaagaggg cggacgcggc ccctaccgtg 420
tcaattttcc caccgagctc cgaacagctc accagcggcg gtgcctcggt cgtgtgcttc 480
ctcaacaact tctatccaaa agacattaac gtcaagtgga agatcgatgg atcggagaga 540
cagaacggag tgctgaacag ctggactgat caggactcca aggattcgac ctactccatg 600
agctccactc tgaccctgac caaggacgaa tacgagcggc acaattccta cacttgcgaa 660
gccacccaca agacctcaac gtcccccatc gtgaagtcct tcaaccgcaa cgagtgc 717

<210> SEQ ID NO 31
<211> LENGTH: 1422
<212> TYPE: DNA
<213> ORGANISM: Artificial Sequence
<220> FEATURE:
<223> OTHER INFORMATION: Mdx001 Heavy Chain Codon-Optimised for Expression in Hamster

<400> SEQUENCE: 31
atgggatgga ctctcgtgtt cctttttctc ctctctgtca ctgccggggt gcattcgcaa 60
gtgcagctgc agcagtccgg ccccgaactc gtgcggccag gcacctccgt gaagatgtcc 120
tgcaaagcgt ccggctacac cttcaccaac tactggatcg gctgggcaaa gcagaggccc 180
ggacatggcc tcgaatggat tggcgacatc tatccgggtg gagactacac caactacaac 240
gaaaagttca agggaaaggc caccctgacc gctgataagt ccagctccac cgcatacatg 300
cagttctcgt cactgactag cgaagattcc gcgatctact actgcgcccg gtggggactt 360
ggttactact tcgactactg gggacaggga attaccctga ccgtgtccag cgccaagact 420
acgccgccgt ccgtctaccc tttggccccc ggttgcggcg acaccaccgg ctcgtcagtg 480
actctgggct gcctcgtgaa ggggtacttc cccgagtccg tcaccgtcac ttggaacagc 540
ggcagccttt cgtcctcggt ccacaccttc cccgctctgc tgcaaagcgg tctgtacacc 600
atgtcctcat ccgtgaccgt gccctcctcc acttggccga gccagaccgt gacttgctcc 660
gtggcccacc cggcgtcctc gaccaccgtg gacaagaagc tggagccgtc aggtccaatc 720
tccaccatca atccctgccc gccttgtaaa gagtgccaca agtgccctgc ccccaatctg 780
gagggaggac cttcggtgtt cattttccct ccgaatatca aggacgtgtt gatgatctcc 840
ctgaccccga aggtcacatg cgtggtcgtc gacgtgtccg aggacgatcc ggacgtgcag 900
attagctggt tcgtgaacaa cgtggaagtg cacactgcgc agacccaaac ccatcgggag 960
gactataact ccactatccg cgtcgtgtca acactgccga tccagcacca ggactggatg 1020
agcggaaagg aattcaagtg taaagtcaac aacaaggatc tgccaagccc tatcgagcgc 1080

```
accattagca agatcaaggg actcgtgcgc gccccacaag tgtacattct cccccctccg   1140

gcggaacagc tgagcagaaa ggatgtgtcg ctgacgtgtt tggtcgtggg attcaacccc   1200

ggggatattt ccgtggaatg gacttcgaac gggcacaccg aagagaacta caaggacacc   1260

gcccctgtgc tggacagcga cggatcatac ttcatctatt cgaagctgaa catgaaaact   1320

tccaaatggg aaaagaccga ctcgttttcc tgtaacgtgc gccacgaagg actcaagaac   1380

tactacctga agaaaactat ctctcggtcc ccggggaagt ga                      1422
```

```
<210> SEQ ID NO 32
<211> LENGTH: 112
<212> TYPE: PRT
<213> ORGANISM: Artificial Sequence
<220> FEATURE:
<223> OTHER INFORMATION: Humanised Light Chain Variable Region L1

<400> SEQUENCE: 32

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Gly Lys Thr Tyr Leu Asn Trp Phe Gln Gln Arg Pro Gly Gln Ser
        35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Lys Leu Glu Ile Lys
            100                 105                 110


<210> SEQ ID NO 33
<211> LENGTH: 118
<212> TYPE: PRT
<213> ORGANISM: Artificial Sequence
<220> FEATURE:
<223> OTHER INFORMATION: Humanised Heavy Chain Variable Region H4

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Val
        35                  40                  45

Gly Asp Ile Tyr Pro Gly Gly Asp Tyr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gly Tyr Tyr Phe Asp Tyr Trp Gly Gln Gly Thr
            100                 105                 110

Met Val Thr Val Ser Ser
        115


<210> SEQ ID NO 34
```

<211> LENGTH: 112
<212> TYPE: PRT
<213> ORGANISM: Artificial Sequence
<220> FEATURE:
<223> OTHER INFORMATION: Humanised Light Chain Variable Region L2

<400> SEQUENCE: 34

Asp Ile Val Met Thr Gln Thr Pro Leu Ser Leu Ser Val Thr Pro Gly
1 5 10 15

Gln Pro Ala Ser Ile Ser Cys Arg Ser Ser Gln Ser Leu Glu Asn Ser
20 25 30

Asn Gly Lys Thr Tyr Leu Asn Trp Tyr Leu Gln Lys Pro Gly Gln Ser
35 40 45

Pro Gln Leu Leu Ile Tyr Gly Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln Val
85 90 95

Thr His Val Pro Tyr Thr Phe Gly Gln Gly Thr Lys Val Glu Ile Lys
100 105 110

<210> SEQ ID NO 35
<211> LENGTH: 118
<212> TYPE: PRT
<213> ORGANISM: Artificial Sequence
<220> FEATURE:
<223> OTHER INFORMATION: Humanised Heavy Chain Variable Region H2

<400> SEQUENCE: 35

Gln Val Gln Leu Val Gln Ser Gly Pro Glu Val Lys Lys Pro Gly Glu
1 5 10 15

Ser Leu Lys Ile Ser Cys Lys Gly Ser Gly Tyr Thr Phe Thr Asn Tyr
20 25 30

Trp Ile Gly Trp Val Arg Gln Ala Pro Gly Lys Gly Leu Glu Trp Met
35 40 45

Gly Asp Ile Tyr Pro Gly Gly Asp Tyr Thr Asn Tyr Asn Glu Lys Phe
50 55 60

Lys Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Ile Tyr Tyr Cys
85 90 95

Ala Arg Trp Gly Leu Gly Tyr Tyr Phe Asp Tyr Trp Gly Arg Gly Thr
100 105 110

Leu Val Thr Val Ser Ser
115

<210> SEQ ID NO 36
<211> LENGTH: 16
<212> TYPE: PRT
<213> ORGANISM: Artificial Sequence
<220> FEATURE:
<223> OTHER INFORMATION: VLCDR1 Variant 1

<400> SEQUENCE: 36

Arg Ser Ser Gln Ser Leu Glu Asn Ser Asn Ala Lys Thr Tyr Leu Asn
1 5 10 15

<210> SEQ ID NO 37
<211> LENGTH: 16

```
<212> TYPE: PRT
<213> ORGANISM: Artificial Sequence
<220> FEATURE:
<223> OTHER INFORMATION: VLCDR1 Variant 2

<400> SEQUENCE: 37

Arg Ser Ser Gln Ser Leu Glu Asn Thr Asn Gly Lys Thr Tyr Leu Asn
1               5                   10                  15


<210> SEQ ID NO 38
<211> LENGTH: 70
<212> TYPE: PRT
<213> ORGANISM: Artificial Sequence
<220> FEATURE:
<223> OTHER INFORMATION: Combined Sequence of CDRs of MDX-L1M2H4 &
      MDX-L2M2H2

<400> SEQUENCE: 38

Arg Ser Ser Gln Ser Leu Glu Asn Ser Asn Ala Lys Thr Tyr Leu Asn
1               5                   10                  15

Gly Val Ser Asn Arg Phe Ser Leu Gln Val Thr His Val Pro Tyr Thr
            20                  25                  30

Gly Tyr Thr Phe Thr Asn Tyr Trp Ile Gly Asp Ile Tyr Pro Gly Gly
        35                  40                  45

Asp Tyr Thr Asn Tyr Asn Glu Lys Phe Lys Gly Ala Arg Trp Gly Leu
    50                  55                  60

Gly Tyr Tyr Phe Asp Tyr
65                  70


<210> SEQ ID NO 39
<211> LENGTH: 70
<212> TYPE: PRT
<213> ORGANISM: Artificial Sequence
<220> FEATURE:
<223> OTHER INFORMATION: Combined Sequence of CDRs of MDX-L1M3H4 &
      MDX-L2M3H2

<400> SEQUENCE: 39

Arg Ser Ser Gln Ser Leu Glu Asn Thr Asn Gly Lys Thr Tyr Leu Asn
1               5                   10                  15

Gly Val Ser Asn Arg Phe Ser Leu Gln Val Thr His Val Pro Tyr Thr
            20                  25                  30

Gly Tyr Thr Phe Thr Asn Tyr Trp Ile Gly Asp Ile Tyr Pro Gly Gly
        35                  40                  45

Asp Tyr Thr Asn Tyr Asn Glu Lys Phe Lys Gly Ala Arg Trp Gly Leu
    50                  55                  60

Gly Tyr Tyr Phe Asp Tyr
65                  70


<210> SEQ ID NO 40
<211> LENGTH: 239
<212> TYPE: PRT
<213> ORGANISM: Artificial Sequence
<220> FEATURE:
<223> OTHER INFORMATION: MDX-L1H4 Light Chain

<400> SEQUENCE: 40

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
```

```
        35                  40                  45

Leu Glu Asn Ser Asn Gly Lys Thr Tyr Leu Asn Trp Phe Gln Gln Arg
    50                  55                  60

Pro Gly Gln Ser Pro Arg Arg Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Leu Gln Val Thr His Val Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 41
<211> LENGTH: 467
<212> TYPE: PRT
<213> ORGANISM: Artificial Sequence
<220> FEATURE:
<223> OTHER INFORMATION: MDX-L1H4 Heavy Chain

<400> SEQUENCE: 41

Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Trp Ile Gly Trp Val Arg Gln Ala Pro Gly Gln Gly Leu
    50                  55                  60

Glu Trp Val Gly Asp Ile Tyr Pro Gly Gly Asp Tyr Thr Asn Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Leu Gly Tyr Tyr Phe Asp Tyr Trp Gly
        115                 120                 125

Gln Gly Thr Met Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
```

```
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 42
<211> LENGTH: 239
<212> TYPE: PRT
<213> ORGANISM: Artificial Sequence
<220> FEATURE:
<223> OTHER INFORMATION: MDX-L2H2 Light Chain

<400> SEQUENCE: 42

```
Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Leu Ser Leu Ser
            20                  25                  30

Val Thr Pro Gly Gln Pro Ala Ser Ile Ser Cys Arg Ser Ser Gln Ser
        35                  40                  45

Leu Glu Asn Ser Asn Gly Lys Thr Tyr Leu Asn Trp Tyr Leu Gln Lys
```

```
    50                  55                  60

Pro Gly Gln Ser Pro Gln Leu Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Leu Gln Val Thr His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 43
<211> LENGTH: 467
<212> TYPE: PRT
<213> ORGANISM: Artificial Sequence
<220> FEATURE:
<223> OTHER INFORMATION: MDX-L2H2 Heavy Chain

<400> SEQUENCE: 43

Met Gly Trp Thr Leu Val Phe Leu Phe Leu Leu Ser Val Thr Ala Gly
1               5                   10                  15

Val His Ser Gln Val Gln Leu Val Gln Ser Gly Pro Glu Val Lys Lys
            20                  25                  30

Pro Gly Glu Ser Leu Lys Ile Ser Cys Lys Gly Ser Gly Tyr Thr Phe
        35                  40                  45

Thr Asn Tyr Trp Ile Gly Trp Val Arg Gln Ala Pro Gly Lys Gly Leu
    50                  55                  60

Glu Trp Met Gly Asp Ile Tyr Pro Gly Gly Asp Tyr Thr Asn Tyr Asn
65                  70                  75                  80

Glu Lys Phe Lys Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Ile
            100                 105                 110

Tyr Tyr Cys Ala Arg Trp Gly Leu Gly Tyr Tyr Phe Asp Tyr Trp Gly
        115                 120                 125

Arg Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
```

```
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 44
<211> LENGTH: 239
<212> TYPE: PRT
<213> ORGANISM: Artificial Sequence
<220> FEATURE:
<223> OTHER INFORMATION: MDX-L1M2H4 Light Chain

<400> SEQUENCE: 44

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Glu Asn Ser Asn Ala Lys Thr Tyr Leu Asn Trp Phe Gln Gln Arg
    50                  55                  60

Pro Gly Gln Ser Pro Arg Arg Leu Ile Tyr Gly Val Ser Asn Arg Phe
```

```
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Leu Gln Val Thr His Val Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 45
<211> LENGTH: 239
<212> TYPE: PRT
<213> ORGANISM: Artificial Sequence
<220> FEATURE:
<223> OTHER INFORMATION: MDX-L2M2H2 Light Chain

<400> SEQUENCE: 45

Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Leu Ser Leu Ser
            20                  25                  30

Val Thr Pro Gly Gln Pro Ala Ser Ile Ser Cys Arg Ser Ser Gln Ser
        35                  40                  45

Leu Glu Asn Ser Asn Ala Lys Thr Tyr Leu Asn Trp Tyr Leu Gln Lys
    50                  55                  60

Pro Gly Gln Ser Pro Gln Leu Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Leu Gln Val Thr His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
```

```
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 46
<211> LENGTH: 239
<212> TYPE: PRT
<213> ORGANISM: Artificial Sequence
<220> FEATURE:
<223> OTHER INFORMATION: MDX-L1M3H4 Light Chain

<400> SEQUENCE: 46

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Glu Asn Thr Asn Gly Lys Thr Tyr Leu Asn Trp Phe Gln Gln Arg
    50                  55                  60

Pro Gly Gln Ser Pro Arg Arg Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Leu Gln Val Thr His Val Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 47
<211> LENGTH: 239
<212> TYPE: PRT
<213> ORGANISM: Artificial Sequence
<220> FEATURE:
<223> OTHER INFORMATION: MDX-L2M3H2 Light Chain

<400> SEQUENCE: 47

Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Leu Ser Leu Ser
            20                  25                  30
```

```
Val Thr Pro Gly Gln Pro Ala Ser Ile Ser Cys Arg Ser Ser Gln Ser
        35                  40                  45

Leu Glu Asn Thr Asn Gly Lys Thr Tyr Leu Asn Trp Tyr Leu Gln Lys
    50                  55                  60

Pro Gly Gln Ser Pro Gln Leu Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Leu Gln Val Thr His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 48
<211> LENGTH: 112
<212> TYPE: PRT
<213> ORGANISM: Artificial Sequence
<220> FEATURE:
<223> OTHER INFORMATION: MDX-L1M2H4 Light Chain Variable Region

<400> SEQUENCE: 48

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Ala Lys Thr Tyr Leu Asn Trp Phe Gln Gln Arg Pro Gly Gln Ser
        35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Lys Leu Glu Ile Lys
            100                 105                 110


<210> SEQ ID NO 49
<211> LENGTH: 112
<212> TYPE: PRT
<213> ORGANISM: Artificial Sequence
<220> FEATURE:
<223> OTHER INFORMATION: MDX-L1M3H4 Light Chain Variable Region

<400> SEQUENCE: 49
```

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Glu Asn Thr
20 25 30

Asn Gly Lys Thr Tyr Leu Asn Trp Phe Gln Gln Arg Pro Gly Gln Ser
35 40 45

Pro Arg Arg Leu Ile Tyr Gly Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Leu Gln Val
85 90 95

Thr His Val Pro Tyr Thr Phe Gly Gln Gly Thr Lys Leu Glu Ile Lys
100 105 110

<210> SEQ ID NO 50
<211> LENGTH: 112
<212> TYPE: PRT
<213> ORGANISM: Artificial Sequence
<220> FEATURE:
<223> OTHER INFORMATION: MDX-L2M2H2 Light Chain Variable Region

<400> SEQUENCE: 50

Asp Ile Val Met Thr Gln Thr Pro Leu Ser Leu Ser Val Thr Pro Gly
1 5 10 15

Gln Pro Ala Ser Ile Ser Cys Arg Ser Ser Gln Ser Leu Glu Asn Ser
20 25 30

Asn Ala Lys Thr Tyr Leu Asn Trp Tyr Leu Gln Lys Pro Gly Gln Ser
35 40 45

Pro Gln Leu Leu Ile Tyr Gly Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln Val
85 90 95

Thr His Val Pro Tyr Thr Phe Gly Gln Gly Thr Lys Val Glu Ile Lys
100 105 110

<210> SEQ ID NO 51
<211> LENGTH: 112
<212> TYPE: PRT
<213> ORGANISM: Artificial Sequence
<220> FEATURE:
<223> OTHER INFORMATION: MDX-L2M3H2 Light Chain Variable Region

<400> SEQUENCE: 51

Asp Ile Val Met Thr Gln Thr Pro Leu Ser Leu Ser Val Thr Pro Gly
1 5 10 15

Gln Pro Ala Ser Ile Ser Cys Arg Ser Ser Gln Ser Leu Glu Asn Thr
20 25 30

Asn Gly Lys Thr Tyr Leu Asn Trp Tyr Leu Gln Lys Pro Gly Gln Ser
35 40 45

Pro Gln Leu Leu Ile Tyr Gly Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln Val

```
                85                  90                  95

Thr His Val Pro Tyr Thr Phe Gly Gln Gly Thr Lys Val Glu Ile Lys
            100                 105                 110


<210> SEQ ID NO 52
<211> LENGTH: 20
<212> TYPE: PRT
<213> ORGANISM: Artificial Sequence
<220> FEATURE:
<223> OTHER INFORMATION: Signal Sequence of Humanised Light Chains

<400> SEQUENCE: 52

Met Val Ser Ser Ala Gln Phe Leu Gly Leu Leu Leu Leu Cys Phe Gln
1               5                   10                  15

Gly Thr Arg Cys
            20


<210> SEQ ID NO 53
<211> LENGTH: 19
<212> TYPE: PRT
<213> ORGANISM: Artificial Sequence
<220> FEATURE:
<223> OTHER INFORMATION: Signal Sequence of Humanised Heavy Chains

<400> SEQUENCE: 53

Met Gly Trp Thr Leu Val Phe Leu Phe Leu Leu Ser Val Thr Ala Gly
1               5                   10                  15

Val His Ser


<210> SEQ ID NO 54
<211> LENGTH: 219
<212> TYPE: PRT
<213> ORGANISM: Artificial Sequence
<220> FEATURE:
<223> OTHER INFORMATION: MDX-L1M2H4 Mature Light Chain

<400> SEQUENCE: 54

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Ala Lys Thr Tyr Leu Asn Trp Phe Gln Gln Arg Pro Gly Gln Ser
        35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 55
<211> LENGTH: 448
<212> TYPE: PRT
<213> ORGANISM: Artificial Sequence
<220> FEATURE:
<223> OTHER INFORMATION: MDX-L1H4 Mature Heavy Chain

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Val
        35                  40                  45

Gly Asp Ile Tyr Pro Gly Gly Asp Tyr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gly Tyr Tyr Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 56
<211> LENGTH: 16
<212> TYPE: PRT
<213> ORGANISM: Artificial Sequence
<220> FEATURE:
<223> OTHER INFORMATION: VLCDR1 "mod1"

<400> SEQUENCE: 56

```
Arg Ser Ser Gln Ser Leu Glu Asn Ser Asp Gly Lys Thr Tyr Leu Asn
1               5                   10                  15
```

<210> SEQ ID NO 57
<211> LENGTH: 720
<212> TYPE: DNA
<213> ORGANISM: Artificial Sequence
<220> FEATURE:
<223> OTHER INFORMATION: MDX-L1M2H4 Light Chain

<400> SEQUENCE: 57

```
atggtgtcat ccgctcaatt tctcggtttg cttctcctgt gtttccaagg cacccgctgc     60

gacgtggtca tgacccagag cccactgagc cttccggtca ccttgggaca gcccgcctca    120

atttcatgcc ggtccagcca gtccctggag aactccaacg ccaagaccta tctgaactgg    180

ttccagcagc gccctggaca gtccccgagg cgcctgatct acggcgtcag caacaggttc    240

tcgggcgtgc cggacagatt ctccggctcc ggaagcggaa ctgacttcac cctgaaaatc    300

tcaagagtgg aagccgagga cgtgggcgtg tacttctgcc tccaagtcac gcacgtgccg    360

tacactttcg gacaagggac taagctggag atcaagcgga ccgtggcggc cccctctgtg    420

ttcattttcc ctccctcgga cgaacagctg aagtcgggaa cagcctccgt cgtgtgcctg    480

ctcaacaact tctacccccg ggaagcgaag gtccagtgga aagtggataa cgcactccaa    540

tcggggaact cccaggaatc cgtgactgag caggactcga aggattccac ttactccctg    600

tcgtccaccc tgactctgag caaggccgac tacgagaagc ataaggtcta cgcctgcgaa    660

gtgacccacc agggtctgag ctcccctgtg accaagagct ttaatcgggg cgaatgttga    720
```

<210> SEQ ID NO 58
<211> LENGTH: 1404
<212> TYPE: DNA
<213> ORGANISM: Artificial Sequence
<220> FEATURE:
<223> OTHER INFORMATION: MDX-L1H4 Heavy Chain

<400> SEQUENCE: 58

```
atgggatgga ctctcgtgtt cctttttctc ctctctgtca ctgccggggt gcattcgcaa     60
gtccagctgg tgcagtcggg agcagaggtg aaaaagcccg gatcgtcagt gaaggtcagc    120
tgcaaagcct cgggatacac tttcaccaac tactggattg gatgggtcag acaggccccc    180
ggccaaggac tggagtgggt cggcgacatc taccctgggg gcgactatac caactacaac    240
gaaaagttca agggacgcgt gacaattacc gccgataaga gcaccagcac tgcctacatg    300
gagcttagct cattgcggtc cgaggatacc gctgtgtact actgtgcgcg gtggggcctt    360
ggttactact tcgactactg gggacagggt accatggtca cggtgtcctc cgcgtccacc    420
aagggtccct ccgtgttccc tctcgcgccg tcctcaaagt ctacctccgg tggaactgcc    480
gcgctcggtt gtctcgtgaa ggactacttc ccggagcctg tgactgtctc ctggaactcc    540
ggggccctca ccagcggagt gcacactttc cccgccgtgc tgcaatcctc cggcctgtac    600
agcctgtcct ccgtcgtgac tgtgcctagc tcctccctgg gaacccagac ctacatctgc    660
aacgtgaacc acaagccctc caacaccaag gtcgacaaga aggtcgaacc gaagtcgtgc    720
gacaagactc atacgtgccc tccttgcccg gccccggaac tgctgggagg cccatccgtg    780
ttcctgttcc cacccaagcc taaggatacc ctgatgatca gcagaacacc ggaagtgacc    840
tgtgtggtgg tggacgtcag ccacgaagat cccgaggtca agttcaattg gtacgtggac    900
ggggtggagg tgcacaacgc aaagaccaag ccccgggagg aacagtacaa ctccacctat    960
cgcgtggtgt cggtgctgac ggtgctgcac caggactggt tgaacggaaa ggagtataag   1020
tgcaaagtgt cgaacaaggc cctgcccgct cctatcgaaa agaccatctc caaggccaag   1080
ggccagccgc gggaacccca ggtctacact ctcccaccga gccgcgacga actgactaag   1140
aatcaagtgt cgctgacttg cctcgtcaag ggcttctacc cgtccgacat cgccgtggaa   1200
tgggagagca acggccagcc ggaaaacaac tacaagacca cccctcccgt gctggattcc   1260
gacgggtcct tcttcctgta ctcaaaactg accgtggata agtccagatg gcagcagggc   1320
aatgtctttt catgctccgt gatgcacgag gctctgcata accactacac ccagaagtcg   1380
ctgtccctgt ccccggggaa gtga                                          1404
```

<210> SEQ ID NO 59
<211> LENGTH: 336
<212> TYPE: DNA
<213> ORGANISM: Artificial Sequence
<220> FEATURE:
<223> OTHER INFORMATION: MDX-L1M2H4 Light Chain Variable Region

<400> SEQUENCE: 59

```
gacgtggtca tgacccagag cccactgagc cttccggtca ccttgggaca gcccgcctca     60
atttcatgcc ggtccagcca gtccctggag aactccaacg ccaagaccta tctgaactgg    120
ttccagcagc gccctggaca gtccccgagg cgcctgatct acggcgtcag caacaggttc    180
tcgggcgtgc cggacagatt ctccggctcc ggaagcggaa ctgacttcac cctgaaaatc    240
tcaagagtgg aagccgagga cgtgggcgtg tacttctgcc tccaagtcac gcacgtgccg    300
tacactttcg gacaagggac taagctggag atcaag                              336
```

<210> SEQ ID NO 60
<211> LENGTH: 354
<212> TYPE: DNA
<213> ORGANISM: Artificial Sequence
<220> FEATURE:
<223> OTHER INFORMATION: MDX-L1H4 Heavy Chain Variable Region

<400> SEQUENCE: 60
caagtccagc tggtgcagtc gggagcagag gtgaaaaagc ccggatcgtc agtgaaggtc 60
agctgcaaag cctcgggata cactttcacc aactactgga ttggatgggt cagacaggcc 120
cccggccaag gactggagtg ggtcggcgac atctaccctg gggcgacta taccaactac 180 aacgaaaagt tcaagggacg cgtgacaatt accgccgata agagcaccag cactgcctac 240
atggagctta gctcattgcg gtccgaggat accgctgtgt actactgtgc gcggtggggc 300
cttggttact acttcgacta ctggggacag ggtaccatgg tcacggtgtc ctcc 354

<210> SEQ ID NO 61
<211> LENGTH: 720
<212> TYPE: DNA
<213> ORGANISM: Artificial Sequence
<220> FEATURE:
<223> OTHER INFORMATION: MDX-L2M2H2 Ligh Chain

<400> SEQUENCE: 61
atggtgtcat ccgctcaatt tctcggtttg cttctcctgt gtttccaagg cacccgctgc 60
gacatcgtca tgacccagac cccattgagc ctttccgtca cgccgggaca gcccgcctcc 120
atttcctgcc gctcaagcca gtccctggag aactcaaacg ccaagaccta cctgaattgg 180
tatctgcaga agcctggaca gagcccgcag ctgctgatct acggcgtcag caacaggttc 240
tcgggcgtgc cggacagatt ctccggctcc ggaagcggaa ctgacttcac cctgaaaatc 300
tcacgcgtgg aagccgagga cgtgggcgtg tactactgcc tccaagtcac ccacgtgccg 360
tacactttcg gacaagggac taaggtcgag atcaagcgga ccgtggcggc cccctctgtg 420
ttcattttcc ctccctcgga cgaacagctg aagtcgggaa cagcctccgt cgtgtgcctg 480
ctcaacaact tctacccccg ggaagcgaag gtccagtgga aagtggataa cgcactccaa 540
tcggggaact cccaggaatc cgtgactgag caggactcga aggattccac ttactccctg 600
tcgtccaccc tgactctgag caaggccgac tacgagaagc ataaggtcta cgcctgcgaa 660
gtgacccacc agggtctgag ctcccctgtg accaagagct ttaatcgggg cgaatgttga 720

<210> SEQ ID NO 62
<211> LENGTH: 1404
<212> TYPE: DNA
<213> ORGANISM: Artificial Sequence
<220> FEATURE:
<223> OTHER INFORMATION: MDX-L2H2 Heavy Chain

<400> SEQUENCE: 62
atgggatgga ctctcgtgtt cctttttctc ctctctgtca ctgccggggt gcattcgcaa 60
gtccagctgg tgcagtcggg accagaggtg aaaaagcccg gagagtcact taagatcagc 120
tgcaaaggct cgggatacac tttcaccaac tactggattg gttgggtcag acaggccccc 180
ggcaaaggac tggagtggat gggcgacatc taccctgggg gcgactatac caactacaac 240
gaaaagttca agggacaagt gacaatttcg gccgataaga gcattagcac tgcatacctt 300
cagtggagct cattgaaggc ctccgatacc gctatctact actgtgcgcg gtggggcctg 360
ggatactact tcgactactg gggaaggggt accttggtca cggtgtcctc cgcgtccacc 420
aagggtccct ccgtgttccc tctcgcgccg tcctcaaagt ctacctccgg tggaactgcc 480
gcgctcggtt gtctcgtgaa ggactacttc ccggagcctg tgactgtctc ctggaactcc 540
ggggccctca ccagcggagt gcacactttc cccgccgtgc tgcaatcctc cggcctgtac 600

```
agcctgtcct ccgtcgtgac tgtgcctagc tcctccctgg gaacccagac ctacatctgc    660

aacgtgaacc acaagccctc caacaccaag gtcgacaaga aggtcgaacc gaagtcgtgc    720

gacaagactc atacgtgccc tccttgcccg gccccggaac tgctgggagg cccatccgtg    780

ttcctgttcc cacccaagcc taaggatacc ctgatgatca gcagaacacc ggaagtgacc    840

tgtgtggtgg tggacgtcag ccacgaagat cccgaggtca agttcaattg gtacgtggac    900

ggggtggagg tgcacaacgc aaagaccaag ccccgggagg aacagtacaa ctccacctat    960

cgcgtggtgt cggtgctgac ggtgctgcac caggactggt tgaacggaaa ggagtataag   1020

tgcaaagtgt cgaacaaggc cctgcccgct cctatcgaaa agaccatctc caaggccaag   1080

ggccagccgc gggaacccca ggtctacact ctcccaccga gccgcgacga actgactaag   1140

aatcaagtgt cgctgacttg cctcgtcaag ggcttctacc cgtccgacat cgccgtggaa   1200

tgggagagca acggccagcc ggaaaacaac tacaagacca cccctcccgt gctggattcc   1260

gacgggtcct tcttcctgta ctcaaaactg accgtggata agtccagatg gcagcagggc   1320

aatgtctttt catgctccgt gatgcacgag gctctgcata accactacac ccagaagtcg   1380

ctgtccctgt ccccggggaa gtga                                          1404
```

<210> SEQ ID NO 63
<211> LENGTH: 336
<212> TYPE: DNA
<213> ORGANISM: Artificial Sequence
<220> FEATURE:
<223> OTHER INFORMATION: MDX-L2M2H2 Light Chain Variable Region

<400> SEQUENCE: 63

```
gacatcgtca tgacccagac cccattgagc ctttccgtca cgccgggaca gcccgcctcc     60

atttcctgcc gctcaagcca gtccctggag aactcaaacg ccaagaccta cctgaattgg    120

tatctgcaga agcctggaca gagcccgcag ctgctgatct acggcgtcag caacaggttc    180

tcgggcgtgc cggacagatt ctccggctcc ggaagcggaa ctgacttcac cctgaaaatc    240

tcacgcgtgg aagccgagga cgtgggcgtg tactactgcc tccaagtcac ccacgtgccg    300

tacactttcg gacaagggac taaggtcgag atcaag                             336
```

<210> SEQ ID NO 64
<211> LENGTH: 354
<212> TYPE: DNA
<213> ORGANISM: Artificial Sequence
<220> FEATURE:
<223> OTHER INFORMATION: MDX-L2H2 Heavy Chain Variable Region

<400> SEQUENCE: 64

```
caagtccagc tggtgcagtc gggaccagag gtgaaaaagc ccggagagtc acttaagatc     60

agctgcaaag gctcgggata cactttcacc aactactgga ttggttgggt cagacaggcc    120

cccggcaaag gactggagtg gatgggcgac atctaccctg gggcgacta taccaactac    180

aacgaaaagt tcaagggaca agtgacaatt tcggccgata agagcattag cactgcatac    240

cttcagtgga gctcattgaa ggcctccgat accgctatct actactgtgc gcggtggggc    300

ctgggatact acttcgacta ctggggaagg ggtaccttgg tcacggtgtc ctcc         354
```

<210> SEQ ID NO 65
<211> LENGTH: 48
<212> TYPE: DNA
<213> ORGANISM: Artificial Sequence
<220> FEATURE:
<223> OTHER INFORMATION: MDX-L1M2H4 VLCDR1

<400> SEQUENCE: 65
cggtccagcc agtccctgga gaactccaac gccaagacct atctgaac 48

<210> SEQ ID NO 66
<211> LENGTH: 48
<212> TYPE: DNA
<213> ORGANISM: Artificial Sequence
<220> FEATURE:
<223> OTHER INFORMATION: MDX-L2M2H2 VLCDR1

<400> SEQUENCE: 66
cgctcaagcc agtccctgga gaactcaaac gccaagacct acctgaat 48

<210> SEQ ID NO 67
<211> LENGTH: 21
<212> TYPE: DNA
<213> ORGANISM: Artificial Sequence
<220> FEATURE:
<223> OTHER INFORMATION: MDX-L1H4 & MDX-L2H2 VLCDR2

<400> SEQUENCE: 67
ggcgtcagca acaggttctc g 21

<210> SEQ ID NO 68
<211> LENGTH: 27
<212> TYPE: DNA
<213> ORGANISM: Artificial Sequence
<220> FEATURE:
<223> OTHER INFORMATION: MDX-L1H4 VLCDR3

<400> SEQUENCE: 68
ctccaagtca cgcacgtgcc gtacact 27

<210> SEQ ID NO 69
<211> LENGTH: 27
<212> TYPE: DNA
<213> ORGANISM: Artificial Sequence
<220> FEATURE:
<223> OTHER INFORMATION: MDX-L2H2 VLCDR3

<400> SEQUENCE: 69
ctccaagtca cccacgtgcc gtacact 27

<210> SEQ ID NO 70
<211> LENGTH: 30
<212> TYPE: DNA
<213> ORGANISM: Artificial Sequence
<220> FEATURE:
<223> OTHER INFORMATION: MDX-L1H4 VHCDR1

<400> SEQUENCE: 70
ggatacactt tcaccaacta ctggattgga 30

<210> SEQ ID NO 71
<211> LENGTH: 30
<212> TYPE: DNA
<213> ORGANISM: Artificial Sequence
<220> FEATURE:
<223> OTHER INFORMATION: MDX-L2H2 VHCDR1

<400> SEQUENCE: 71
ggatacactt tcaccaacta ctggattggt 30

<210> SEQ ID NO 72

<211> LENGTH: 51
<212> TYPE: DNA
<213> ORGANISM: Artificial Sequence
<220> FEATURE:
<223> OTHER INFORMATION: MDX-L1H4 & MDX-L2H2 VHCDR2

<400> SEQUENCE: 72
gacatctacc ctgggggcga ctataccaac tacaacgaaa agttcaaggg a 51

<210> SEQ ID NO 73
<211> LENGTH: 33
<212> TYPE: DNA
<213> ORGANISM: Artificial Sequence
<220> FEATURE:
<223> OTHER INFORMATION: MDX-L1H4 VHCDR3

<400> SEQUENCE: 73
gcgcggtggg gccttggtta ctacttcgac tac 33

<210> SEQ ID NO 74
<211> LENGTH: 33
<212> TYPE: DNA
<213> ORGANISM: Artificial Sequence
<220> FEATURE:
<223> OTHER INFORMATION: MDX-L2H2 VHCDR3

<400> SEQUENCE: 74
gcgcggtggg gcctgggata ctacttcgac tac 33

<210> SEQ ID NO 75
<211> LENGTH: 219
<212> TYPE: PRT
<213> ORGANISM: Artificial Sequence
<220> FEATURE:
<223> OTHER INFORMATION: MDX-L1H4 Mature Light Chain

<400> SEQUENCE: 75

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Gly Lys Thr Tyr Leu Asn Trp Phe Gln Gln Arg Pro Gly Gln Ser
        35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 76
<211> LENGTH: 219
<212> TYPE: PRT
<213> ORGANISM: Artificial Sequence
<220> FEATURE:
<223> OTHER INFORMATION: MDX-L1M3H4 Mature Light Chain

<400> SEQUENCE: 76

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Thr
            20                  25                  30

Asn Gly Lys Thr Tyr Leu Asn Trp Phe Gln Gln Arg Pro Gly Gln Ser
        35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 77
<211> LENGTH: 219
<212> TYPE: PRT
<213> ORGANISM: Artificial Sequence
<220> FEATURE:
<223> OTHER INFORMATION: MDX-L2H2 Mature Light Chain

<400> SEQUENCE: 77

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Ser
            20                  25                  30

Asn Gly Lys Thr Tyr Leu Asn Trp Tyr Leu Gln Lys Pro Gly Gln Ser
        35                  40                  45

Pro Gln Leu Leu Ile Tyr Gly Val Ser Asn Arg Phe Ser Gly Val Pro
```

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 78
<211> LENGTH: 219
<212> TYPE: PRT
<213> ORGANISM: Artificial Sequence
<220> FEATURE:
<223> OTHER INFORMATION: MDX-L2M2H2 Mature Light Chain

<400> SEQUENCE: 78

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Ser
            20                  25                  30

Asn Ala Lys Thr Tyr Leu Asn Trp Tyr Leu Gln Lys Pro Gly Gln Ser
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
        195                 200                 205

Pro Val Thr Lys Ser Phe Asn Arg Gly Glu Cys
    210                 215


<210> SEQ ID NO 79
<211> LENGTH: 219
<212> TYPE: PRT
<213> ORGANISM: Artificial Sequence
<220> FEATURE:
<223> OTHER INFORMATION: MDX-L2M3H2 Mature Light Chain

<400> SEQUENCE: 79

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Lys Thr Tyr Leu Asn Trp Tyr Leu Gln Lys Pro Gly Gln Ser
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 80
<211> LENGTH: 448
<212> TYPE: PRT
<213> ORGANISM: Artificial Sequence
<220> FEATURE:
<223> OTHER INFORMATION: MDX-L2H2 Mature Heavy Chain

<400> SEQUENCE: 80

Gln Val Gln Leu Val Gln Ser Gly Pro Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile Gly Trp Val Arg Gln Ala Pro Gly Lys Gly Leu Glu Trp Met
        35                  40                  45

Gly Asp Ile Tyr Pro Gly Gly Asp Tyr Thr Asn Tyr Asn Glu Lys Phe
    50                  55                  60
```

```
Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Trp Gly Leu Gly Tyr Tyr Phe Asp Tyr Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 81
<211> LENGTH: 720
<212> TYPE: DNA
<213> ORGANISM: Artificial Sequence
<220> FEATURE:
<223> OTHER INFORMATION: MDX-L1H4 Light Chain

<400> SEQUENCE: 81

```
atggtgtcat ccgctcaatt tctcggtttg cttctcctgt gtttccaagg cacccgctgc     60
gacgtggtca tgacccagag cccactgagc cttccggtca ccttgggaca gcccgcctca    120
atttcatgcc ggtccagcca gtccctggag aactccaacg gaaagaccta tctgaactgg    180
ttccagcagc gccctggaca gtccccgagg cgcctgatct acggcgtcag caacaggttc    240
tcgggcgtgc cggacagatt ctccggctcc ggaagcggaa ctgacttcac cctgaaaatc    300
tcaagagtgg aagccgagga cgtgggcgtg tactactgcc tccaagtcac gcacgtgccg    360
tacactttcg gacaagggac taagctggag atcaagcgga ccgtggcggc cccctctgtg    420
ttcatttcc ctccctcgga cgaacagctg aagtcgggaa cagcctccgt cgtgtgcctg    480
ctcaacaact tctacccccg ggaagcgaag gtccagtgga aagtggataa cgcactccaa    540
tcggggaact cccaggaatc cgtgactgag caggactcga aggattccac ttactccctg    600
tcgtccaccc tgactctgag caaggccgac tacgagaagc ataaggtcta cgcctgcgaa    660
gtgacccacc agggtctgag ctcccctgtg accaagagct ttaatcgggg cgaatgttga    720
```

<210> SEQ ID NO 82
<211> LENGTH: 336
<212> TYPE: DNA
<213> ORGANISM: Artificial Sequence
<220> FEATURE:
<223> OTHER INFORMATION: MDX-L1H4 Light Chain Variable Region

<400> SEQUENCE: 82

```
gacgtggtca tgacccagag cccactgagc cttccggtca ccttgggaca gcccgcctca     60
atttcatgcc ggtccagcca gtccctggag aactccaacg gaaagaccta tctgaactgg    120
ttccagcagc gccctggaca gtccccgagg cgcctgatct acggcgtcag caacaggttc    180
tcgggcgtgc cggacagatt ctccggctcc ggaagcggaa ctgacttcac cctgaaaatc    240
tcaagagtgg aagccgagga cgtgggcgtg tactactgcc tccaagtcac gcacgtgccg    300
tacactttcg gacaagggac taagctggag atcaag                              336
```

<210> SEQ ID NO 83
<211> LENGTH: 720
<212> TYPE: DNA
<213> ORGANISM: Artificial Sequence
<220> FEATURE:
<223> OTHER INFORMATION: MDX-L2H2 Light Chain

<400> SEQUENCE: 83

```
atggtgtcat ccgctcaatt tctcggtttg cttctcctgt gtttccaagg cacccgctgc     60
gacatcgtca tgacccagac cccattgagc ctttccgtca cgccgggaca gcccgcctcc    120
atttcctgcc gctcaagcca gtccctggag aactcaaacg gaaagaccta cctgaattgg    180
tatctgcaga agcctggaca gagcccgcag ctgctgatct acggcgtcag caacaggttc    240
tcgggcgtgc cggacagatt ctccggctcc ggaagcggaa ctgacttcac cctgaaaatc    300
tcacgcgtgg aagccgagga cgtgggcgtg tactactgcc tccaagtcac ccacgtgccg    360
tacactttcg gacaagggac taaggtcgag atcaagcgga ccgtggcggc cccctctgtg    420
ttcatttcc ctccctcgga cgaacagctg aagtcgggaa cagcctccgt cgtgtgcctg    480
ctcaacaact tctacccccg ggaagcgaag gtccagtgga aagtggataa cgcactccaa    540
tcggggaact cccaggaatc cgtgactgag caggactcga aggattccac ttactccctg    600
```

```
tcgtccaccc tgactctgag caaggccgac tacgagaagc ataaggtcta cgcctgcgaa    660

gtgacccacc agggtctgag ctcccctgtg accaagagct ttaatcgggg cgaatgttga    720


<210> SEQ ID NO 84
<211> LENGTH: 336
<212> TYPE: DNA
<213> ORGANISM: Artificial Sequence
<220> FEATURE:
<223> OTHER INFORMATION: MDX-L2H2 Ligh Chain Variable Region

<400> SEQUENCE: 84

gacatcgtca tgacccagac cccattgagc ctttccgtca cgccgggaca gcccgcctcc     60

atttcctgcc gctcaagcca gtccctggag aactcaaacg gaaagaccta cctgaattgg    120

tatctgcaga agcctggaca gagcccgcag ctgctgatct acggcgtcag caacaggttc    180

tcgggcgtgc cggacagatt ctccggctcc ggaagcggaa ctgacttcac cctgaaaatc    240

tcacgcgtgg aagccgagga cgtgggcgtg tactactgcc tccaagtcac ccacgtgccg    300

tacactttcg gacaagggac taaggtcgag atcaag                              336


<210> SEQ ID NO 85
<211> LENGTH: 48
<212> TYPE: DNA
<213> ORGANISM: Artificial Sequence
<220> FEATURE:
<223> OTHER INFORMATION: MDX-L1H4 VLCDR1

<400> SEQUENCE: 85

cggtccagcc agtccctgga gaactccaac ggaaagacct atctgaac                  48


<210> SEQ ID NO 86
<211> LENGTH: 48
<212> TYPE: DNA
<213> ORGANISM: Artificial Sequence
<220> FEATURE:
<223> OTHER INFORMATION: MDX-L2H2 VLCDR1

<400> SEQUENCE: 86

cgctcaagcc agtccctgga gaactcaaac ggaaagacct acctgaat                  48


<210> SEQ ID NO 87
<211> LENGTH: 48
<212> TYPE: DNA
<213> ORGANISM: Artificial Sequence
<220> FEATURE:
<223> OTHER INFORMATION: MDX-L1M3H4 VLCDR1

<400> SEQUENCE: 87

cggtccagcc agtccctgga gaacaccaac ggaaagacct atctgaac                  48


<210> SEQ ID NO 88
<211> LENGTH: 48
<212> TYPE: DNA
<213> ORGANISM: Artificial Sequence
<220> FEATURE:
<223> OTHER INFORMATION: MDX-L2M3H2 VLCDR1

<400> SEQUENCE: 88

cgctcaagcc agtccctgga gaacaccaac ggaaagacct acctgaat                  48


<210> SEQ ID NO 89
<211> LENGTH: 720
<212> TYPE: DNA
<213> ORGANISM: Artificial Sequence
```

```
<220> FEATURE:
<223> OTHER INFORMATION: MDX-L1M3H4 Light Chain

<400> SEQUENCE: 89

atggtgtcat ccgctcaatt tctcggtttg cttctcctgt gtttccaagg cacccgctgc     60

gacgtggtca tgacccagag cccactgagc cttccggtca ccttgggaca gcccgcctca    120

atttcatgcc ggtccagcca gtccctggag aacaccaacg gaaagaccta tctgaactgg    180

ttccagcagc gccctggaca gtccccgagg cgcctgatct acggcgtcag caacaggttc    240

tcgggcgtgc cggacagatt ctccggctcc ggaagcggaa ctgacttcac cctgaaaatc    300

tcaagagtgg aagccgagga cgtgggcgtg tacttctgcc tccaagtcac gcacgtgccg    360

tacactttcg gacaagggac taagctggag atcaagcgga ccgtggcggc cccctctgtg    420

ttcattttcc ctccctcgga cgaacagctg aagtcgggaa cagcctccgt cgtgtgcctg    480

ctcaacaact tctacccccg ggaagcgaag gtccagtgga aagtggataa cgcactccaa    540

tcggggaact cccaggaatc cgtgactgag caggactcga aggattccac ttactccctg    600

tcgtccaccc tgactctgag caaggccgac tacgagaagc ataaggtcta cgcctgcgaa    660

gtgacccacc agggtctgag ctcccctgtg accaagagct ttaatcgggg cgaatgttga    720


<210> SEQ ID NO 90
<211> LENGTH: 336
<212> TYPE: DNA
<213> ORGANISM: Artificial Sequence
<220> FEATURE:
<223> OTHER INFORMATION: MDX-L1M3H4 Light Chain Variable Region

<400> SEQUENCE: 90

gacgtggtca tgacccagag cccactgagc cttccggtca ccttgggaca gcccgcctca     60

atttcatgcc ggtccagcca gtccctggag aacaccaacg gaaagaccta tctgaactgg    120

ttccagcagc gccctggaca gtccccgagg cgcctgatct acggcgtcag caacaggttc    180

tcgggcgtgc cggacagatt ctccggctcc ggaagcggaa ctgacttcac cctgaaaatc    240

tcaagagtgg aagccgagga cgtgggcgtg tacttctgcc tccaagtcac gcacgtgccg    300

tacactttcg gacaagggac taagctggag atcaag                              336


<210> SEQ ID NO 91
<211> LENGTH: 720
<212> TYPE: DNA
<213> ORGANISM: Artificial Sequence
<220> FEATURE:
<223> OTHER INFORMATION: MDX-L2M3H2 Light Chain

<400> SEQUENCE: 91

atggtgtcat ccgctcaatt tctcggtttg cttctcctgt gtttccaagg cacccgctgc     60

gacatcgtca tgacccagac cccattgagc ctttccgtca cgccgggaca gcccgcctcc    120

atttcctgcc gctcaagcca gtccctggag aacaccaacg gaaagaccta cctgaattgg    180

tatctgcaga agcctggaca gagcccgcag ctgctgatct acggcgtcag caacaggttc    240

tcgggcgtgc cggacagatt ctccggctcc ggaagcggaa ctgacttcac cctgaaaatc    300

tcacgcgtgg aagccgagga cgtgggcgtg tactactgcc tccaagtcac ccacgtgccg    360

tacactttcg gacaagggac taaggtcgag atcaagcgga ccgtggcggc cccctctgtg    420

ttcattttcc ctccctcgga cgaacagctg aagtcgggaa cagcctccgt cgtgtgcctg    480

ctcaacaact tctacccccg ggaagcgaag gtccagtgga aagtggataa cgcactccaa    540
```

-continued

```
tcggggaact cccaggaatc cgtgactgag caggactcga aggattccac ttactccctg    600

tcgtccaccc tgactctgag caaggccgac tacgagaagc ataaggtcta cgcctgcgaa    660

gtgacccacc agggtctgag ctcccctgtg accaagagct ttaatcgggg cgaatgttga    720


<210> SEQ ID NO 92
<211> LENGTH: 336
<212> TYPE: DNA
<213> ORGANISM: Artificial Sequence
<220> FEATURE:
<223> OTHER INFORMATION: MDX-L2M3H2 Light Chain Variable Region

<400> SEQUENCE: 92

gacatcgtca tgacccagac cccattgagc ctttccgtca cgccgggaca gcccgcctcc     60

atttcctgcc gctcaagcca gtccctggag aacaccaacg gaaagaccta cctgaattgg    120

tatctgcaga agcctggaca gagcccgcag ctgctgatct acggcgtcag caacaggttc    180

tcgggcgtgc cggacagatt ctccggctcc ggaagcggaa ctgacttcac cctgaaaatc    240

tcacgcgtgg aagccgagga cgtgggcgtg tactactgcc tccaagtcac ccacgtgccg    300

tacactttcg gacaagggac taaggtcgag atcaag                              336
```